United States Patent
Glorioso et al.

(10) Patent No.: US 7,037,492 B2
(45) Date of Patent: *May 2, 2006

(54) GENE TRANSFER FOR STUDYING AND TREATING A CONNECTIVE TISSUE OF A MAMMALIAN HOST

(75) Inventors: Joseph C. Glorioso, Cheswick, PA (US); Christopher H. Evans, Pittsburgh, PA (US); Paul D. Robbins, Pittsburgh, PA (US)

(73) Assignee: University of Pittsburgh of the Commonwealth System of Higher Education, Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 371 days.

(21) Appl. No.: 09/731,175

(22) Filed: Dec. 5, 2000

(65) Prior Publication Data

US 2002/0098168 A1 Jul. 25, 2002

Related U.S. Application Data

(63) Continuation of application No. 08/924,777, filed on Sep. 5, 1997, now Pat. No. 6,156,304, which is a continuation-in-part of application No. 08/381,603, filed on Jan. 27, 1995, now Pat. No. 5,858,355, and a continuation-in-part of application No. 08/685,212, filed on Jul. 23, 1996, now Pat. No. 6,228,356, which is a continuation of application No. 08/027,750, filed on Mar. 8, 1993, now abandoned, and a continuation-in-part of application No. 08/567,710, filed on Dec. 5, 1995, now abandoned, which is a continuation of application No. 08/183,563, filed on Jan. 18, 1994, now abandoned, which is a continuation of application No. 07/963,928, filed on Oct. 20, 1992, now abandoned, which is a continuation of application No. 07/630,981, filed on Dec. 20, 1990, now abandoned.

(51) Int. Cl.
*A61K 35/00* (2006.01)
*C12N 5/00* (2006.01)
*C12N 15/63* (2006.01)
*C12N 15/09* (2006.01)

(52) U.S. Cl. .................. 424/93.2; 435/320.1; 435/325; 435/455; 435/456

(58) Field of Classification Search ............... 424/93.1, 424/93.2; 435/320.1, 325, 455, 456
See application file for complete search history.

(56) References Cited

U.S. PATENT DOCUMENTS 5,492,888 A * 2/1996 Dower et al. .................. 514/2

OTHER PUBLICATIONS

Bandara et al. Proc. Natl. Acad. Sci. USA. vol. 90:10764–10768, 1993.*
Bandara et al. DNA and Cell Biology 11:227–231, 1993.*
Hammer C. Blood Purification 19:322–328, 2001.*

* cited by examiner

*Primary Examiner*—Ram R. Shukla
(74) *Attorney, Agent, or Firm*—JHK Law; Joseph Hyasuk Kim

(57) ABSTRACT

Methods for introducing at least one gene encoding a product into at least one target cell of a mammalian host for use in treating the mammalian host are disclosed. These methods include employing recombinant techniques to produce a vector molecule that contains the gene encoding for the product, and infecting the target cells of the mammalian host using the DNA vector molecule. A method to produce an animal model for the study of connective tissue pathology is also disclosed.

12 Claims, 26 Drawing Sheets

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 1770 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 55..1764
      (D) OTHER INFORMATION: /product= "human interleukin-1
         receptor"

(xi) SEQUENCE DESCRIPTION: SEQ ID NO: 1:

```
CCTCCTGAGA AGCTGGACCC CTTGGTAAAA GACAAGGCCT TCTCCAAGAA GAAT ATG           57
                                                            Met
                                                              1

AAA GTG TTA CTC AGA CTT ATT TGT TTC ATA GCT CTA CTG ATT TCT TCT          105
Lys Val Leu Leu Arg Leu Ile Cys Phe Ile Ala Leu Leu Ile Ser Ser
              5                  10                  15

CTG GAG GCT GAT AAA TGC AAG GAA CGT GAA GAA AAA ATA ATT TTA GTG          153
Leu Glu Ala Asp Lys Cys Lys Glu Arg Glu Glu Lys Ile Ile Leu Val
         20                  25                  30

TCA TCT GCA AAT GAA ATT GAT GTT CGT CCC TGT CCT CTT AAC CCA AAT          201
Ser Ser Ala Asn Glu Ile Asp Val Arg Pro Cys Pro Leu Asn Pro Asn
     35                  40                  45

GAA CAC AAA GGC ACT ATA ACT TGG TAT AAA GAT GAC AGC AAG ACA CCT          249
Glu His Lys Gly Thr Ile Thr Trp Tyr Lys Asp Asp Ser Lys Thr Pro
 50                  55                  60                  65

GTA TCT ACA GAA CAA GCC TCC AGG ATT CAT CAA CAC AAA GAG AAA CTT          297
Val Ser Thr Glu Gln Ala Ser Arg Ile His Gln His Lys Glu Lys Leu
                 70                  75                  80

TGG TTT GTT CCT GCT AAG GTG GAG GAT TCA GGA CAT TAC TAT TGC GTG          345
Trp Phe Val Pro Ala Lys Val Glu Asp Ser Gly His Tyr Tyr Cys Val
             85                  90                  95

GTA AGA AAT TCA TCT TAC TGC CTC AGA ATT AAA ATA AGT GCA AAA TTT          393
Val Arg Asn Ser Ser Tyr Cys Leu Arg Ile Lys Ile Ser Ala Lys Phe
        100                 105                 110

GTG GAG AAT GAG CCT AAC TTA TGT TAT AAT GCA CAA GCC ATA TTT AAG          441
Val Glu Asn Glu Pro Asn Leu Cys Tyr Asn Ala Gln Ala Ile Phe Lys
    115                 120                 125

CAG AAA CTA CCC GTT GCA GGA GAC GGA GGA CTT GTG TGC CCT TAT ATG          489
Gln Lys Leu Pro Val Ala Gly Asp Gly Gly Leu Val Cys Pro Tyr Met
130                 135                 140                 145

GAG TTT TTT AAA AAT GAA AAT AAT GAG TTA CCT AAA TTA CAG TGG TAT          537
Glu Phe Phe Lys Asn Glu Asn Asn Glu Leu Pro Lys Leu Gln Trp Tyr
                150                 155                 160

AAG GAT TGC AAA CCT CTA CTT CTT GAC AAT ATA CAC TTT AGT GGA GTC          585
Lys Asp Cys Lys Pro Leu Leu Leu Asp Asn Ile His Phe Ser Gly Val
            165                 170                 175

AAA GAT AGG CTC ATC GTG ATG AAT GTG GCT GAA AAG CAT AGA GGG AAC          633
Lys Asp Arg Leu Ile Val Met Asn Val Ala Glu Lys His Arg Gly Asn
        180                 185                 190
```

```
TAT ACT TGT CAT GCA TCC TAC ACA TAC TTG GGC AAG CAA TAT CCT ATT      681
Tyr Thr Cys His Ala Ser Tyr Thr Tyr Leu Gly Lys Gln Tyr Pro Ile
    195                 200                 205

ACC CGG GTA ATA GAA TTT ATT ACT CTA GAG GAA AAC AAA CCC ACA AGG      729
Thr Arg Val Ile Glu Phe Ile Thr Leu Glu Glu Asn Lys Pro Thr Arg
210                 215                 220                 225

CCT GTG ATT GTG AGC CCA GCT AAT GAG ACA ATG GAA GTA GAC TTG GGA      777
Pro Val Ile Val Ser Pro Ala Asn Glu Thr Met Glu Val Asp Leu Gly
                230                 235                 240

TCC CAG ATA CAA TTG ATC TGT AAT GTC ACC GGC CAG TTG AGT GAC ATT      825
Ser Gln Ile Gln Leu Ile Cys Asn Val Thr Gly Gln Leu Ser Asp Ile
                245                 250                 255

GCT TAC TGG AAG TGG AAT GGG TCA GTA ATT GAT GAA GAT GAC CCA GTG      873
Ala Tyr Trp Lys Trp Asn Gly Ser Val Ile Asp Glu Asp Asp Pro Val
        260                 265                 270

CTA GGG GAA GAC TAT TAC AGT GTG GAA AAT CCT GCA AAC AAA AGA AGG      921
Leu Gly Glu Asp Tyr Tyr Ser Val Glu Asn Pro Ala Asn Lys Arg Arg
        275                 280                 285

AGT ACC CTC ATC ACA GTG CTT AAT ATA TCG GAA ATT GAA AGT AGA TTT      969
Ser Thr Leu Ile Thr Val Leu Asn Ile Ser Glu Ile Glu Ser Arg Phe
290                 295                 300                 305

TAT AAA CAT CCA TTT ACC TGT TTT GCC AAG AAT ACA CAT GGT ATA GAT     1017
Tyr Lys His Pro Phe Thr Cys Phe Ala Lys Asn Thr His Gly Ile Asp
                310                 315                 320

GCA GCA TAT ATC CAG TTA ATA TAT CCA GTC ACT AAT TTC CAG AAG CAC     1065
Ala Ala Tyr Ile Gln Leu Ile Tyr Pro Val Thr Asn Phe Gln Lys His
            325                 330                 335

ATG ATT GGT ATA TGT GTC ACG TTG ACA GTC ATA ATT GTG TGT TCT GTT     1113
Met Ile Gly Ile Cys Val Thr Leu Thr Val Ile Ile Val Cys Ser Val
            340                 345                 350

TTC ATC TAT AAA ATC TTC AAG ATT GAC ATT GTG CTT TGG TAC AGG GAT     1161
Phe Ile Tyr Lys Ile Phe Lys Ile Asp Ile Val Leu Trp Tyr Arg Asp
355                 360                 365

TCC TGC TAT GAT TTT CTC CCA ATA AAA GCT TCA GAT GGA AAG ACC TAT     1209
Ser Cys Tyr Asp Phe Leu Pro Ile Lys Ala Ser Asp Gly Lys Thr Tyr
370                 375                 380                 385

GAC GCA TAT ATA CTG TAT CCA AAG ACT GTT GGG GAA GGG TCT ACC TCT     1257
Asp Ala Tyr Ile Leu Tyr Pro Lys Thr Val Gly Glu Gly Ser Thr Ser
                390                 395                 400

GAC TGT GAT ATT TTT GTG TTT AAA GTC TTG CCT GAG GTC TTG GAA AAA     1305
Asp Cys Asp Ile Phe Val Phe Lys Val Leu Pro Glu Val Leu Glu Lys
            405                 410                 415

CAG TGT GGA TAT AAG CTG TTC ATT TAT GGA AGG GAT GAC TAC GTT GGG     1353
Gln Cys Gly Tyr Lys Leu Phe Ile Tyr Gly Arg Asp Asp Tyr Val Gly
            420                 425                 430

GAA GAC ATT GTT GAG GTC ATT AAT GAA AAC GTA AAG AAA AGC AGA AGA     1401
Glu Asp Ile Val Glu Val Ile Asn Glu Asn Val Lys Lys Ser Arg Arg
435                 440                 445

CTG ATT ATC ATT TTA GTC AGA GAA ACA TCA GGC TTC AGC TGG CTG GGT     1449
Leu Ile Ile Ile Leu Val Arg Glu Thr Ser Gly Phe Ser Trp Leu Gly
450                 455                 460                 465

GGT TCA TCT GAA GAG CAA ATA GCC ATG TAT AAT GCT CTT GTT CAG GAT     1497
Gly Ser Ser Glu Glu Gln Ile Ala Met Tyr Asn Ala Leu Val Gln Asp
                470                 475                 480

GGA ATT AAA GTT GTC CTG CTT GAG CTG GAG AAA ATC CAA GAC TAT GAG     1545
Gly Ile Lys Val Val Leu Leu Glu Leu Glu Lys Ile Gln Asp Tyr Glu
            485                 490                 495

AAA ATG CCA GAA TCG ATT AAA TTC ATT AAG CAG AAA CAT GGG GCT ATC     1593
Lys Met Pro Glu Ser Ile Lys Phe Ile Lys Gln Lys His Gly Ala Ile
            500                 505                 510
```

-continued

```
CGC TGG TCA GGG GAC TTT ACA CAG GGA CCA CAG TCT GCA AAG ACA AGG         1641
Arg Trp Ser Gly Asp Phe Thr Gln Gly Pro Gln Ser Ala Lys Thr Arg
515                 520                 525

TTC TGG AAG AAT GTC AGG TAC CAC ATG CCA GTC CAG CGA CGG TCA CCT         1689
Phe Trp Lys Asn Val Arg Tyr His Met Pro Val Gln Arg Arg Ser Pro
530                 535                 540                 545

TCA TCT AAA CAC CAG TTA CTG TCA CCA GCC ACT AAG GAG AAA CTG CAA         1737
Ser Ser Lys His Gln Leu Leu Ser Pro Ala Thr Lys Glu Lys Leu Gln
                550                 555                 560

AGA GAG GCT CAC GTG CCT CTC GGG TAGCATGGA                               1770
Arg Glu Ala His Val Pro Leu Gly
565
```

(2) INFORMATION FOR SEQ ID NO: 2:

(i) SEQUENCE CHARACTERISTICS:
        (A) LENGTH: 569 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270
```

-continued

```
Val Leu Gly Glu Asp Tyr Tyr Ser Val Glu Asn Pro Ala Asn Lys Arg
        275                 280                 285
Arg Ser Thr Leu Ile Thr Val Leu Asn Ile Ser Glu Ile Glu Ser Arg
    290                 295                 300
Phe Tyr Lys His Pro Phe Thr Cys Phe Ala Lys Asn Thr His Gly Ile
305                 310                 315                 320
Asp Ala Ala Tyr Ile Gln Leu Ile Tyr Pro Val Thr Asn Phe Gln Lys
                325                 330                 335
His Met Ile Gly Ile Cys Val Thr Leu Thr Val Ile Ile Val Cys Ser
                340                 345                 350
Val Phe Ile Tyr Lys Ile Phe Lys Ile Asp Ile Val Leu Trp Tyr Arg
            355                 360                 365
Asp Ser Cys Tyr Asp Phe Leu Pro Ile Lys Ala Ser Asp Gly Lys Thr
370                 375                 380
Tyr Asp Ala Tyr Ile Leu Tyr Pro Lys Thr Val Gly Glu Gly Ser Thr
385                 390                 395                 400
Ser Asp Cys Asp Ile Phe Val Phe Lys Val Leu Pro Glu Val Leu Glu
                405                 410                 415
Lys Gln Cys Gly Tyr Lys Leu Phe Ile Tyr Gly Arg Asp Asp Tyr Val
                420                 425                 430
Gly Glu Asp Ile Val Glu Val Ile Asn Glu Asn Val Lys Lys Ser Arg
            435                 440                 445
Arg Leu Ile Ile Ile Leu Val Arg Glu Thr Ser Gly Phe Ser Trp Leu
    450                 455                 460
Gly Gly Ser Ser Glu Glu Gln Ile Ala Met Tyr Asn Ala Leu Val Gln
465                 470                 475                 480
Asp Gly Ile Lys Val Val Leu Leu Glu Leu Glu Lys Ile Gln Asp Tyr
                485                 490                 495
Glu Lys Met Pro Glu Ser Ile Lys Phe Ile Lys Gln Lys His Gly Ala
                500                 505                 510
Ile Arg Trp Ser Gly Asp Phe Thr Gln Gly Pro Gln Ser Ala Lys Thr
            515                 520                 525
Arg Phe Trp Lys Asn Val Arg Tyr His Met Pro Val Gln Arg Arg Ser
    530                 535                 540
Pro Ser Ser Lys His Gln Leu Leu Ser Pro Ala Thr Lys Glu Lys Leu
545                 550                 555                 560
Gln Arg Glu Ala His Val Pro Leu Gly
                565
```

(2) INFORMATION FOR SEQ ID NO: 3:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 46..1776
        (D) OTHER INFORMATION: /product= "mouse interleukin-1 receptor"

(xi) SEQUENCE DESCRIPTION: SEQ ID NO: 3:

```
GGATGTCATC AGAGTTCCCA GTGCCCCGAA CCGTGAACAA CACAA ATG GAG AAT    54
                                                 Met Glu Asn
                                                   1
```

```
ATG AAA GTG CTA CTG GGG CTC ATT TGT CTC ATG GTG CCT CTG CTG TCG        102
Met Lys Val Leu Leu Gly Leu Ile Cys Leu Met Val Pro Leu Leu Ser
     5                  10                  15

CTG GAG ATT GAC GTA TGT ACA GAA TAT CCA AAT CAG ATC GTT TTG TTT        150
Leu Glu Ile Asp Val Cys Thr Glu Tyr Pro Asn Gln Ile Val Leu Phe
 20                  25                  30                  35

TTA TCT GTA AAT GAA ATT GAT ATT CGC AAG TGT CCT CTT ACT CCA AAT        198
Leu Ser Val Asn Glu Ile Asp Ile Arg Lys Cys Pro Leu Thr Pro Asn
                 40                  45                  50

AAA ATG CAC GGC GAC ACC ATA ATT TGG TAC AAG AAT GAC AGC AAG ACC        246
Lys Met His Gly Asp Thr Ile Ile Trp Tyr Lys Asn Asp Ser Lys Thr
             55                  60                  65

CCC ATA TCA GCG GAC CGG GAC TCC AGG ATT CAT CAG CAG AAT GAA CAT        294
Pro Ile Ser Ala Asp Arg Asp Ser Arg Ile His Gln Gln Asn Glu His
         70                  75                  80

CTT TGG TTT GTA CCT GCC AAG GTG GAG GAC TCA GGA TAT TAC TAT TGT        342
Leu Trp Phe Val Pro Ala Lys Val Glu Asp Ser Gly Tyr Tyr Tyr Cys
 85                  90                  95

ATA GTA AGA AAC TCA ACT TAC TGC CTC AAA ACT AAA GTA ACC GTA ACT        390
Ile Val Arg Asn Ser Thr Tyr Cys Leu Lys Thr Lys Val Thr Val Thr
100                 105                 110                 115

GTG TTA GAG AAT GAC CCT GGC TTG TGT TAC AGC ACA CAG GCC ACC TTC        438
Val Leu Glu Asn Asp Pro Gly Leu Cys Tyr Ser Thr Gln Ala Thr Phe
                120                 125                 130

CCA CAG CGG CTC CAC ATT GCC GGG GAT GGA AGT CTT GTG TGC CCT TAT        486
Pro Gln Arg Leu His Ile Ala Gly Asp Gly Ser Leu Val Cys Pro Tyr
            135                 140                 145

GTG AGT TAT TTT AAA GAT GAA AAT AAT GAG TTA CCC GAG GTC CAG TGG        534
Val Ser Tyr Phe Lys Asp Glu Asn Asn Glu Leu Pro Glu Val Gln Trp
        150                 155                 160

TAT AAG AAC TGT AAA CCT CTG CTT CTT GAC AAC GTG AGC TTC TTC GGA        582
Tyr Lys Asn Cys Lys Pro Leu Leu Leu Asp Asn Val Ser Phe Phe Gly
    165                 170                 175

GTA AAA GAT AAA CTG TTG GTG AGG AAT GTG GCT GAA GAG CAC AGA GGG        630
Val Lys Asp Lys Leu Leu Val Arg Asn Val Ala Glu Glu His Arg Gly
180                 185                 190                 195

GAC TAT ATA TGC CGT ATG TCC TAT ACG TTC CGG GGG AAG CAA TAT CCG        678
Asp Tyr Ile Cys Arg Met Ser Tyr Thr Phe Arg Gly Lys Gln Tyr Pro
                200                 205                 210

GTC ACA CGA GTA ATA CAA TTT ATC ACA ATA GAT GAA AAC AAG AGG GAC        726
Val Thr Arg Val Ile Gln Phe Ile Thr Ile Asp Glu Asn Lys Arg Asp
            215                 220                 225

AGA CCT GTT ATC CTG AGC CCT CGG AAT GAG ACG ATC GAA GCT GAC CCA        774
Arg Pro Val Ile Leu Ser Pro Arg Asn Glu Thr Ile Glu Ala Asp Pro
        230                 235                 240

GGA TCA ATG ATA CAA CTG ATC TGC AAC GTC ACG GGC CAG TTC TCA GAC        822
Gly Ser Met Ile Gln Leu Ile Cys Asn Val Thr Gly Gln Phe Ser Asp
    245                 250                 255

CTT GTC TAC TGG AAG TGG AAT GGA TCA GAA ATT GAA TGG AAT GAT CCA        870
Leu Val Tyr Trp Lys Trp Asn Gly Ser Glu Ile Glu Trp Asn Asp Pro
260                 265                 270                 275

TTT CTA GCT GAA GAC TAT CAA TTT GTG GAA CAT CCT TCA ACC AAA AGA        918
Phe Leu Ala Glu Asp Tyr Gln Phe Val Glu His Pro Ser Thr Lys Arg
                280                 285                 290

AAA TAC ACA CTC ATT ACA ACA CTT AAC ATT TCA GAA GTT AAA AGC CAG        966
Lys Tyr Thr Leu Ile Thr Thr Leu Asn Ile Ser Glu Val Lys Ser Gln
            295                 300                 305

TTT TAT CGC TAT CCG TTT ATC TGT GTT GTT AAG AAC ACA AAT ATT TTT       1014
Phe Tyr Arg Tyr Pro Phe Ile Cys Val Val Lys Asn Thr Asn Ile Phe
        310                 315                 320
```

```
GAG TCG GCG CAT GTG CAG TTA ATA TAC CCA GTC CCT GAC TTC AAG AAT    1062
Glu Ser Ala His Val Gln Leu Ile Tyr Pro Val Pro Asp Phe Lys Asn
325                 330                 335

TAC CTC ATC GGG GGC TTT ATC ATC CTC ACG GCT ACA ATT GTA TGC TGT    1110
Tyr Leu Ile Gly Gly Phe Ile Ile Leu Thr Ala Thr Ile Val Cys Cys
340                 345                 350                 355

GTG TGC ATC TAT AAA GTC TTC AAG GTT GAC ATA GTG CTT TGG TAC AGG    1158
Val Cys Ile Tyr Lys Val Phe Lys Val Asp Ile Val Leu Trp Tyr Arg
                360                 365                 370

GAC TCC TGC TCT GGT TTT CTT CCT TCA AAA GCT TCA GAT GGA AAG ACA    1206
Asp Ser Cys Ser Gly Phe Leu Pro Ser Lys Ala Ser Asp Gly Lys Thr
            375                 380                 385

TAC GAT GCA TAT ATT CTT TAT CCC AAG ACC CTG GGA GAG GGG TCC TTC    1254
Tyr Asp Ala Tyr Ile Leu Tyr Pro Lys Thr Leu Gly Glu Gly Ser Phe
        390                 395                 400

TCA GAC TTA GAT ACT TTT GTT TTT AAA CTG TTG CCT GAG GTC TTG GAG    1302
Ser Asp Leu Asp Thr Phe Val Phe Lys Leu Leu Pro Glu Val Leu Glu
405                 410                 415

GGA CAG TTT GGA TAC AAG CTG TTC ATT TAT GGA AGG GAT GAC TAT GTT    1350
Gly Gln Phe Gly Tyr Lys Leu Phe Ile Tyr Gly Arg Asp Asp Tyr Val
420                 425                 430                 435

GGA GAA GAT ACC ATC GAG GTT ACT AAT GAA AAT GTA AAG AAA AGC AGG    1398
Gly Glu Asp Thr Ile Glu Val Thr Asn Glu Asn Val Lys Lys Ser Arg
                440                 445                 450

AGG CTG ATT ATC ATT CTA GTG AGA GAT ATG GGA GGC TTC AGC TGG CTG    1446
Arg Leu Ile Ile Ile Leu Val Arg Asp Met Gly Gly Phe Ser Trp Leu
            455                 460                 465

GGC CAG TCA TCT GAA GAG CAA ATA GCC ATA TAC AAT GCT CTC ATC CAG    1494
Gly Gln Ser Ser Glu Glu Gln Ile Ala Ile Tyr Asn Ala Leu Ile Gln
        470                 475                 480

GAA GGA ATT AAA ATC GTC CTG CTT GAG TTG GAG AAA ATC CAA GAC TAT    1542
Glu Gly Ile Lys Ile Val Leu Leu Glu Leu Glu Lys Ile Gln Asp Tyr
485                 490                 495

GAG AAA ATG CCA GAT TCT ATT CAG TTC ATT AAG CAG AAA CAC GGA GTC    1590
Glu Lys Met Pro Asp Ser Ile Gln Phe Ile Lys Gln Lys His Gly Val
500                 505                 510                 515

ATT TGC TGG TCA GGA GAC TTT CAA GAA AGA CCA CAG TCT GCA AAG ACC    1638
Ile Cys Trp Ser Gly Asp Phe Gln Glu Arg Pro Gln Ser Ala Lys Thr
                520                 525                 530

AGG TTC TGG AAA AAC TTA AGA TAC CAG ATG CCA GCC CAA CGG AGA TCA    1686
Arg Phe Trp Lys Asn Leu Arg Tyr Gln Met Pro Ala Gln Arg Arg Ser
            535                 540                 545

CCA TTG TCT AAA CAC CGC TTA CTA ACC CTG GAT CCT GTG CGG GAC ACT    1734
Pro Leu Ser Lys His Arg Leu Leu Thr Leu Asp Pro Val Arg Asp Thr
        550                 555                 560

AAG GAG AAA CTG CCG GCA GCA ACA CAC TTA CCA CTC GGC TAGCATGGC     1782
Lys Glu Lys Leu Pro Ala Ala Thr His Leu Pro Leu Gly
565                 570                 575
```

(2) INFORMATION FOR SEQ ID NO: 4:

(i) SEQUENCE CHARACTERISTICS:
        (A) LENGTH: 576 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Glu Asn Met Lys Val Leu Leu Gly Leu Ile Cys Leu Met Val Pro
1               5                   10                  15
```

```
Leu Leu Ser Leu Glu Ile Asp Val Cys Thr Glu Tyr Pro Asn Gln Ile
             20                  25                  30

Val Leu Phe Leu Ser Val Asn Glu Ile Asp Ile Arg Lys Cys Pro Leu
         35                  40                  45

Thr Pro Asn Lys Met His Gly Asp Thr Ile Ile Trp Tyr Lys Asn Asp
     50                  55                  60

Ser Lys Thr Pro Ile Ser Ala Asp Arg Asp Ser Arg Ile His Gln Gln
 65                  70                  75                  80

Asn Glu His Leu Trp Phe Val Pro Ala Lys Val Glu Asp Ser Gly Tyr
                 85                  90                  95

Tyr Tyr Cys Ile Val Arg Asn Ser Thr Tyr Cys Leu Lys Thr Lys Val
             100                 105                 110

Thr Val Thr Val Leu Glu Asn Asp Pro Gly Leu Cys Tyr Ser Thr Gln
         115                 120                 125

Ala Thr Phe Pro Gln Arg Leu His Ile Ala Gly Asp Gly Ser Leu Val
130                 135                 140

Cys Pro Tyr Val Ser Tyr Phe Lys Asp Glu Asn Asn Glu Leu Pro Glu
145                 150                 155                 160

Val Gln Trp Tyr Lys Asn Cys Lys Pro Leu Leu Leu Asp Asn Val Ser
                165                 170                 175

Phe Phe Gly Val Lys Asp Lys Leu Leu Val Arg Asn Val Ala Glu Glu
            180                 185                 190

His Arg Gly Asp Tyr Ile Cys Arg Met Ser Tyr Thr Phe Arg Gly Lys
        195                 200                 205

Gln Tyr Pro Val Thr Arg Val Ile Gln Phe Ile Thr Ile Asp Glu Asn
    210                 215                 220

Lys Arg Asp Arg Pro Val Ile Leu Ser Pro Arg Asn Glu Thr Ile Glu
225                 230                 235                 240

Ala Asp Pro Gly Ser Met Ile Gln Leu Ile Cys Asn Val Thr Gly Gln
                245                 250                 255

Phe Ser Asp Leu Val Tyr Trp Lys Trp Asn Gly Ser Glu Ile Glu Trp
            260                 265                 270

Asn Asp Pro Phe Leu Ala Glu Asp Tyr Gln Phe Val Glu His Pro Ser
        275                 280                 285

Thr Lys Arg Lys Tyr Thr Leu Ile Thr Thr Leu Asn Ile Ser Glu Val
    290                 295                 300

Lys Ser Gln Phe Tyr Arg Tyr Pro Phe Ile Cys Val Val Lys Asn Thr
305                 310                 315                 320

Asn Ile Phe Glu Ser Ala His Val Gln Leu Ile Tyr Pro Val Pro Asp
                325                 330                 335

Phe Lys Asn Tyr Leu Ile Gly Gly Phe Ile Ile Leu Thr Ala Thr Ile
            340                 345                 350

Val Cys Cys Val Cys Ile Tyr Lys Val Phe Lys Val Asp Ile Val Leu
        355                 360                 365

Trp Tyr Arg Asp Ser Cys Ser Gly Phe Leu Pro Ser Lys Ala Ser Asp
    370                 375                 380

Gly Lys Thr Tyr Asp Ala Tyr Ile Leu Tyr Pro Lys Thr Leu Gly Glu
385                 390                 395                 400

Gly Ser Phe Ser Asp Leu Asp Thr Phe Val Phe Lys Leu Leu Pro Glu
                405                 410                 415

Val Leu Glu Gly Gln Phe Gly Tyr Lys Leu Phe Ile Tyr Gly Arg Asp
            420                 425                 430
```

```
Asp Tyr Val Gly Glu Asp Thr Ile Glu Val Thr Asn Glu Asn Val Lys
        435                 440                 445
Lys Ser Arg Arg Leu Ile Ile Ile Leu Val Arg Asp Met Gly Gly Phe
    450                 455                 460
Ser Trp Leu Gly Gln Ser Ser Glu Glu Gln Ile Ala Ile Tyr Asn Ala
465                 470                 475                 480
Leu Ile Gln Glu Gly Ile Lys Ile Val Leu Glu Leu Glu Lys Ile
                485                 490                 495
Gln Asp Tyr Glu Lys Met Pro Asp Ser Ile Gln Phe Ile Lys Gln Lys
        500                 505                 510
His Gly Val Ile Cys Trp Ser Gly Asp Phe Gln Glu Arg Pro Gln Ser
        515                 520                 525
Ala Lys Thr Arg Phe Trp Lys Asn Leu Arg Tyr Gln Met Pro Ala Gln
    530                 535                 540
Arg Arg Ser Pro Leu Ser Lys His Arg Leu Leu Thr Leu Asp Pro Val
545                 550                 555                 560
Arg Asp Thr Lys Glu Lys Leu Pro Ala Ala Thr His Leu Pro Leu Gly
                565                 570                 575
```

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GCGGATCCCC TCCTGAGAAG CT                                        22

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

GCGGATCCCA TGTGCTACTG G                                         21

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

GGCACCATGG TACCTGCA                                             18

(2) INFORMATION FOR SEQ ID NO: 8:

(i) SEQUENCE CHARACTERISTICS:
        (A) LENGTH: 21 base pairs
        (B) TYPE: nucleic acid

```
       (C) STRANDEDNESS: single
       (D) TOPOLOGY: linear (ii) MOLECULE TYPE: DNA (xi) SEQUENCE DESCRIPTION: SEQ ID NO: 8:

AGCACAGGAT CCTCTGGGTA C                                                    21
```

GENE TRANSFER FOR STUDYING AND TREATING A CONNECTIVE TISSUE OF A MAMMALIAN HOST

CROSS-REFERENCE TO RELATED APPLICATION

This application is a continuation of and claims the benefit of U.S. application Ser. No. 08/924,777, filed Sep. 5, 1997, now U.S. Pat. No. 6,156,304 the disclosure of which is incorporated by reference. This is a continuation-in-part application of U.S. application Ser. No. 08/381,603, filed Jan. 27, 1995, now U.S. Pat. No. 5,858,355 a continuation-in-part of U.S. application Ser. No. 08/685,212, filed Jul. 23, 1996, now U.S. Pat. No. 6,228,356 which is a continuation of U.S. Ser. No. 08/027,750, filed Mar. 8, 1993, now abandoned, and a continuation-in-part application of U.S. application Ser. No. 08/567,710, filed Dec. 5, 1995, now abandoned which was a continuation of U.S. application Ser. No. 08/183,563, filed Jan. 18, 1994, now abandoned, which was a continuation application of U.S. application Ser. No. 07/963,928, filed Oct. 20, 1992, now abandoned, which was a continuation application of U.S. application Ser. No. 07/630,981, filed Dec. 20, 1990, now abandoned.

BACKGROUND OF THE INVENTION

1. Field of the Invention

The present invention relates to a method of introducing at least one gene encoding a product into at least one cell of a mammalian host for use in treating the mammalian host. This method discloses employing vector molecules containing a gene encoding the product and infecting, for example, connective tissue cell of the mammalian host using the vector molecule. This invention provides both viral and non-viral methods of introducing at least one gene encoding a product into at least one cell of the mammalian host to treat the mammalian host.

More specifically, the present invention discloses ex vivo and in vivo techniques for delivery of a DNA sequence of interest to the connective tissue cells of the mammalian host. The ex vivo technique involves prior removal and culture of target connective tissue cells, in vitro infection of the DNA sequence by vector or other delivery vehicle into the connective tissue cells, and transplantation of the modified connective tissue cells to the mammalian host such as of a target joint, so as to effect in vivo expression of the gene product of interest. As an alternative, non-connective tissue cells, such as hematopoietic progenitor cells, stromal cells, bone marrow cells, myoblasts, leukocytes or mature lymphoid or myeloid cells may be transfected in vitro, recovered and injected into the bone marrow or blood stream of the patient using techniques known to the skilled artisan. These cells can also be injected locally into the connective tissue.

The in vivo technique bypasses the requirement for in vitro culture of target cells, instead relying on direct transplantation of the DNA sequence by vector or other delivery vehicle to the target cells in vivo, thus effecting expression of the gene product of interest. For example, the gene encoding the product of interest can be introduced into liposomes and injected directly into the area of the joint, where the liposomes fuse with synovial cells, resulting in an in vivo gene transfer to synovial tissue. Alternatively, the gene encoding the product of interest can be introduced into the area of the joint as naked DNA. The naked DNA enters the synovial cell, resulting in an in vivo gene transfer to synovial tissue.

The present invention also relates to a method for producing an animal model for the study of connective tissue pathologies and systemic indices of inflammation.

2. Brief Description of the Related Art

Arthritis involves inflammation of a joint that is usually accompanied by pain and frequent changes in the structure of the joint. Arthritis may result from or be associated with a number of conditions including infection, immunological disturbances, trauma and degenerative joint diseases, such as osteoarthritis. The biochemistry of cartilage degradation in joints and cellular changes have received considerable investigation.

In a healthy joint, cells in cartilage (chondrocytes) and the surrounding synovium (synoviocytes) are in a resting state. In this resting state, these cells secrete basal levels of prostaglandins, cytokines and various proteinases, such as collagenase, gelatinase and stromelysin, with the ability to degrade cartilage. During the development of an arthritic condition, these cells become activated. In the activated state, synoviocytes and chondrocytes synthesize and secrete large amounts of prostaglandins, cytokines and proteinases.

In efforts to identify pathophysiologically relevant cell activators, it has been known that the cytokine interleukin-1 activates chondrocytes and synoviocytes and induces cartilage breakdown in vitro and in vivo. Additionally, interleukin-1 is a growth factor for synoviocytes and promotes their synthesis of matrix, two properties suggesting the involvement of interleukin-1 in the synovial hypertrophy that accompanies arthritis. In contrast, interleukin-1 inhibits cartilaginous matrix synthesis by chondrocytes, thereby suppressing repair of cartilage. Interleukin-1 also induces bone resorption and thus may account for the loss of bone density seen in rheumatoid arthritis. Interleukin-1 is inflammatory, serves as a growth factor for lymphocytes, is a chemotactic factor and a possible activator of polymorphonuclear leukocytes (PMNs). When present in a sufficient concentration, interleukin-1 may cause fever, muscle wasting and sleepiness.

The major source of interleukin-1 in the joint is the synovium. Interleukin-1 is secreted by the resident synoviocytes, which are joined under inflammatory conditions by macrophages and other white blood cells.

Much attention has been devoted to the development of a class of agents identified as the "Non-Steroidal Anti-Inflammatory Drugs" (hereinafter "NSAIDs"). The NSAIDs inhibit cartilage synthesis and repair and control inflammation. The mechanism of action of the NSAIDs appears to be associated principally with the inhibition of prostaglandin synthesis in body tissues. Most of this development has involved the synthesis of better inhibitors of cyclo-oxygenase, a key enzyme that catalyzes the formation of prostaglandin precursors (endoperoxides) from arachidonic acid. The anti-inflammatory effect of the NSAIDs is thought to be due in part to inhibition of prostaglandin synthesis and release during inflammation. Prostaglandins are also believed to play a role in modulating the rate and extent of leukocyte infiltration during inflammation. The NSAIDs include drugs such as acetylsalicylic acid (aspirin), fenoprofen calcium (Nalfon® Pulvules®, Dista Products Company), ibuprofen (Motrin®, The Upjohn Company), and indomethacin (Indocin®, Merck and Company, Inc.).

Therapeutic intervention in arthritis is hindered by the inability to target drugs, such as the NSAIDs, to specific areas within a mammalian host, such as a joint. Traditional routes of drug delivery, such as oral, intravenous or intramuscular administration, depend upon vascular perfusion of the synovium to carry the drug to the joint. This is inefficient because transynovial transfer of small molecules from the synovial capillaries to the joint space occurs generally by passive diffusion. This diffusion is less efficient with increased size of the target molecule. Thus, the access of large drug molecules, for example, proteins, to the joint space is substantially restricted. Intra-articular injection of drugs circumvents those limitations; however, the half-life of drugs administered intraarticularly is generally short. Another disadvantage of intra-articular injection of drugs is that frequent repeated injections are necessary to obtain acceptable drug levels at the joint spaces for treating a chronic condition, such as arthritis. Because therapeutic agents heretofore could not be selectively targeted to joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side effects, such as gastrointestinal upset and changes in the hematological, cardiovascular, hepatic and renal systems of the mammalian host.

It has been shown that genetic material can be introduced into mammalian cells by chemical or biological means. Moreover, the introduced genetic material can be expressed so that high levels of a specific protein can be synthesized by the host cell. Cells retaining the introduced genetic material may include an antibiotic resistance gene thus providing a selectable marker for preferential growth of the transduced cell in the presence of the corresponding antibiotic. Chemical compounds for inhibiting the production of interleukin-1 are also known.

U.S. Pat. No. 4,778,806 discloses a method of inhibiting the production of interleukin-1 by monocytes and/or macrophages in a human by administering through the parenteral route a 2-2'-[1,3-propan-2-onediyl-bis (thio)] bis-1 H-imidazole or a pharmaceutically acceptable salt thereof. This patent discloses a chemical compound for inhibiting the production of interleukin-1. By contrast, in one embodiment of the present invention, gene therapy is employed that is capable of binding to and neutralizing interleukin-1.

U.S. Pat. No. 4,780,470 discloses a method of inhibiting the production of interleukin-1 by monocytes in a human by administering a 4,5-diaryl-2 (substituted) imidazole. This patent also discloses a chemical compound for inhibiting the production of interleukin-1.

U.S. Pat. No. 4,794,114 discloses a method of inhibiting the 5-lipoxygenase pathway in a human by administering a diaryl-substituted imidazole fused to a thiazole, pyrrolidine or piperidine ring or a pharmaceutically acceptable salt thereof. This patent also discloses a chemical compound for inhibiting the production of interleukin-1.

U.S. Pat. No. 4,870,101 discloses a method for inhibiting the release of interleukin-1 and for alleviating interleukin-1 mediated conditions by administering an effective amount of a pharmaceutically acceptable anti-oxidant compound such as disulfiram, tetrakis [3-(2,6-di-tert-butyl-4-hydroxyphenyl) propionyloxy methyl] methane or 2,4-di-isobutyl-6-(N,N-dimethylamino methyl)-phenol. This patent discloses a chemical compound for inhibiting the release of interleukin-1.

U.S. Pat. No. 4,816,436 discloses a process for the use of interleukin-1 as an anti-arthritic agent. This patent states that interleukin-1, in association with a pharmaceutical carrier, may be administered by intra-articular injection for the treatment of arthritis or inflammation. In contrast, the present invention discloses a method of using and preparing a gene that is capable of binding to and neutralizing interleukin-1 as a method of resisting arthritis.

U.S. Pat. No. 4,935,343 discloses an immunoassay method for the detection of interleukin-1 beta that employs a monoclonal antibody that binds to interleukin-1 beta but does not bind to interleukin-1 alpha. This patent discloses that the monoclonal antibody binds to interleukin-1 beta and blocks the binding of interleukin-1 beta to interleukin-1 receptors, and thus blocking the biological activity of interleukin-1 beta. The monoclonal antibody disclosed in this patent may be obtained by production of an immunogen through genetic engineering using recombinant DNA technology. The immunogen is injected into a mouse and thereafter spleen cells of the mouse are immortalized by fusing the spleen cells with myeloma cells. The resulting cells include the hybrid continuous cell lines (hybridomas) that may be later screened for monoclonal antibodies. This patent states that the monoclonal antibodies of the invention may be used therapeutically, such as for example, in the immunization of a patient, or the monoclonal antibodies may be bound to a toxin to form an immunotoxin or to a radioactive material or drug to form a radio pharmaceutical or pharmaceutical.

U.S. Pat. No. 4,766,069 discloses a recombinant DNA cloning vehicle having a DNA sequence comprising the human interleukin-1 gene DNA sequence. This patent provides a process for preparing human interleukin-1 beta, and recovering the human interleukin-1 beta. This patent discloses use of interleukin-1 as an immunological reagent in humans because of its ability to stimulate T-cells and B-cells and increase immunoglobulin synthesis.

U.S. Pat. No. 4,396,601 discloses a method for providing mammalian hosts with additional genetic capability. This patent provides that host cells capable of regeneration are removed from the host and treated with genetic material including at least one marker which allows for selective advantage for the host cells in which the genetic material is capable of expression and replication. This patent states that the modified host cells are then returned to the host under regenerative conditions.

U.S. Pat. No. 4,968,607 discloses a DNA sequence encoding a mammalian interleukin-1 receptor protein which exhibits interleukin-1 binding activity.

U.S. Pat. No. 5,081,228 discloses a DNA sequence encoding both the murine and human interleukin-1 receptor. This patent also provides a process for the in vitro expression of said DNA sequences.

U.S. Pat. No. 5,180,812 discloses a substantially pure preparation of the human interleukin-1 receptor protein.

Patent Application WO9634955 discloses a method of treating an arthritic condition using recombinantly modified articular chondrocytes.

U.S. Pat. No. 5,643,752 discloses a host cell transformed with an expression vector containing nucleic acid amino acids 30–224 of the TIMP-4 polypeptide.

Patent Application WO9723639 discloses expression vectors containing DNA encoding a protein having the formula A-X-B, where A and B are subunits of a dimeric protein or are each a biologically active protein; X is a linker polypeptide. Transformed hosts containing the vectors are also disclosed. The method reportedly can be used for the production of interleukin-12 using, DNA coding for the 40 Kd and 35 Kd subunits of IL-12, joined by a suitable linker.

Patent Application WO9700958 discloses an isolated nucleic acid encoding pCL13, a member of TGF-β family member, having immunosuppressant, cell differentiation promoting and anti-proliferative activities.

In spite of these disclosures, there remains a very real and substantial need for a method for introducing at least one gene encoding a product of interest into at least one cell of a mammalian host in vitro, or alternatively in vivo, for use in treating the mammalian host. Further, there is a need for a process wherein a gene encoding a soluble interleukin-1 receptor is used to resist the deleterious pathological changes associated with arthritis. There is also a need to utilize one or more DNA sequences for delivery to and expression of a protein or protein fragment within a target host connective tissue cell, such as a synovial cell, or non-connective tissue cell so as to effect a treatment of various joint pathologies and concomitant systemic indices of inflammation. A further need exists to provide an animal model for the study of joint pathologies.

SUMMARY OF THE INVENTION

The present invention has met the above needs. A method of introducing at least one gene encoding a product of interest into at least one cell of a mammalian host for use in treating the mammalian host is provided by the present invention. This method includes employing recombinant techniques to produce a vector molecule containing the gene encoding for the product and infecting the target cell of the mammalian host using the vector molecule containing the gene. The vector molecule can be any molecule capable of being delivered and maintained within the target cell or tissue such that the gene encoding the product of interest can be stably expressed. The vector molecule preferably utilized in the present invention is either a viral or retroviral vector molecule or a plasmid DNA non-viral molecule. This method preferably includes introducing the gene encoding the product into the cell of the mammalian connective tissue for a therapeutic or prophylactic use. Unlike previous pharmacological efforts, the methods of the present invention employ gene therapy to address the chronic debilitating effects of joint pathologies.

One ex vivo method of treating a connective tissue disorder disclosed throughout this specification comprises generating a recombinant viral vector which contains at least one DNA sequence encoding a protein or biologically active fragment thereof. This recombinant viral vector is then used to infect a population of in vitro cultured connective tissue cells or non-connective tissue cells, resulting in a population of transduced cells. These transduced cells are then transplanted to the host, for example in a target joint space, bone marrow, or blood stream of a mammalian host, effecting subsequent expression of the protein or protein fragment within the joint space of the host. Expression of the DNA sequence of interest is useful in substantially reducing at least one deleterious joint pathology or indicia of inflammation normally associated with a connective tissue disorder.

The methods of the present invention include employing a gene that encodes one or more of the materials selected from the group consisting of (a) a human interleukin-1 receptor antagonist protein (IRAP); (b) a Lac Z marker gene capable of encoding a beta-galactosidase protein; (c) a soluble interleukin-1 receptor protein (sIL-1R); (d) a soluble TNF-α receptor protein (sTNF-αR); (e) a proteinase inhibitor; (f) a cytokine; (g) CTLA4;(h) FasL; (i) BMP; (j) an anti-adhesion molecule; (k) a free radical antagonist; and (l) iNOS. Biologically active derivatives and fragments of these proteins are also within the scope of the present invention.

The genes used in the present methods can be introduced to the host in various ways. One embodiment of the invention employs a viral vector. Preferably the viral vector is a vector selected from the group which includes (a) a retroviral vector such as MFG or pLJ, (b) an adeno-associated virus, (c) an adenovirus, and (d) a herpes virus, including but not limited to herpes simplex 1 or herpes simplex 2.

Another ex vivo embodiment if the invention employs a DNA plasmid vector. The DNA plasmid vector can be any DNA plasmid vector known to one of ordinary skill in the art capable of stable maintenance within the targeted cell or tissue upon delivery, regardless of the method of delivery utilized. One such method is the direct delivery of the DNA vector molecule, whether it be a viral or plasmid DNA vector molecule, to the target cell or tissue.

Another ex vivo embodiment of this invention employs non-viral means for introducing the gene encoding for the product into the target cell of the host. More specifically, this method includes employing non-viral means selected from the group which includes (a) at least one liposome, (b) $Ca_3(PO_4)_2$, (c) electroporation, (d) DEAE-dextran, and (e) injection of naked DNA. Transfected cells are then introduced to the host.

A further ex vivo embodiment of this invention includes employing the biological means of utilizing a virus to deliver the DNA vector molecule to the target cell or tissue. Preferably, the virus is a pseudo-type retrovirus, the genome having been altered such that the pseudo-type retrovirus is capable only of delivery and stable maintenance within the target cell, but not retaining an ability to replicate within the target cell or tissue. The altered viral genome is further manipulated by recombinant DNA techniques such that the viral genome acts as a DNA vector molecule containing the gene of interest to be expressed within the target cell or tissue.

In vivo methods can also be used to introduce the gene of interest to the host cell. Viral or non-viral vectors can all be used for in vivo transduction or transfection of host cells, as can non-viral and biological means as described above. The step of in vitro transduction or transfection by these vehicles is eliminated in the in vivo methods, as the vehicle containing the DNA sequence is introduced directly to the host. Infection with the gene(s) of interest occurs in vivo.

A further embodiment of this invention provides for an animal model and method of producing an animal model to study connective tissue pathologies and indices of systemic inflammation. This model utilizes either ex vivo or in vivo delivery of at least one gene or DNA sequence of interest into at least one cell of a mammalian host. Examples of joint pathologies which can be studied in the present invention include, but are not limited to, joint pathologies such as leukocytosis, synovitis, cartilage breakdown and suppression of cartilage matrix synchesis. Examples of indices of systemic inflammation include, but are not limited to, elevated erythrocyte sedimentation rate, fever and weight loss.

More specifically, the animal model embodiments for the study of joint pathologies generally comprise generating a recombinant viral or plasmid vector which contains a DNA sequence encoding a protein, or biologically active derivative or fragment thereof, known to cause or contribute to one or more of the joint pathologies or symptoms associated with a connective tissue disorder; infecting a population of in vitro cultured target cells with said recombinant viral vector, resulting in a population of transfected target cells; and transplanting said transfected connective cells to a joint space of a mammalian host. The DNA sequence used in the animal model embodiments encode a compound known to be associated with the deleterious effects of a connective tissue disorder. DNA sequences particularly suited for animal model studies are DNA sequences encoding interleukin-1α (IL-1α), IL-1β, IL-2, IL-8, IL-12, IL-15, IL-17, tumor necrosis factor α (TNF-α), TNF-β and proteinases such as gelatinase, stromelysin, collagenase and aggrecanase or biologically active derivatives or fragments thereof. Subsequent expression of these proteins within the joint space of the host therefore causes at least one deleterious joint pathology or indicia of inflammation normally associated with a connective tissue disorder in the afflicted joint. The animal in which arthritis is induced can then be used to test the efficacy of various methods devised to reduce the symptoms associated with a connective tissue disorder.

Means for delivering genes of interest include, for example, the recombinant viral vectors, plasmid vectors, non-viral means or biological means described above in connection with the therapeutic methods of the present invention. In vivo methods as described above can also be used to introduce the DNA sequence of interest directly to the animal host joint.

In a specific method disclosed as an example, and not as a limitation to the present invention, a DNA plasmid vector containing the interleukin-1 beta (IL-1β) coding sequence was ligated downstream of the cytomegalovirus (CMV) promoter. This DNA plasmid construction was encapsulated within liposomes and injected intra-articularly into the knee joints of recipient rabbits. IL-1β was expressed and significant amounts of IL-1β were recovered from the synovial tissue. An alternative is injection of the naked plasmid DNA into the knee joint, allowing direct transfection of the DNA into the synovial tissue. Injection of IL-1β into the joint of a mammalian host allows for prolonged study of various joint pathologies and systemic indices of inflammation, as described within this specification.

Another example demonstrates the introduction and subsequent expression of human interleukin-1β (hIL-1β) into rabbit knee joints using the retroviral vector DFG-hIL-1-neo. Again, this resulted in a severe inflammatory arthritis, having pathophysiological changes consistent with those seen in human arthritic conditions. Thus the present invention provides a reliable animal model for the study of connective tissue disorders, which is predictive of human studies. An animal model as described and exemplified in this specification measures the ability of various gene therapy applications disclosed throughout this specification to withstand challenges from known causative agents (such as IL-1β) of joint pathologies and inflammatory side effects.

A preferred method of the present invention for the therapeutic treatment of a host involves delivering the IRAP gene to the synovial lining of a mammalian host through use of a retroviral vector with the ex vivo technique disclosed within this specification. A DNA sequence of interest encoding a functional IRAP protein or protein fragment is subcloned into a retroviral vector of choice, the recombinant viral vector is then grown to adequate titers and used to infect in vitro cultured synovial cells, and the transduced synovial cells, preferably autografted cells, are transplanted into the joint of interest, preferably by intra-articular injection. Other preferred methods of the present invention involve delivery of vIL-10, IL-10, sTNF-αR, and sIL-1R instead of IRAP.

Another preferred method of the present invention involves direct in vivo delivery of the IRAP gene to the synovial lining of a mammalian host through use of either an adenovirus vector, an adeno-associated virus (AAV) vector or a herpes-simplex virus (HSV) vector. A DNA sequence of interest encoding a functional IRAP protein or protein fragment is subcloned into the respective viral vector, the IRAP-containing viral vector is then grown to adequate titers, and directed into the joint space, preferably by intra-articular injection. A retroviral-IRAP construct, such as MFG-IRAP may also be utilized to directly target cells within the joint space. Preferred variations of this method for in vivo delivery can be performed using DNA sequences encoding sTNF-αR, sIL-1R, one or more of the cytokines that possess anti-inflammatory and/or immunomodulatory characteristics such as IL-4, IL-10 or IL-13, anti-adhesion molecules that inhibit cell-cell and cell-matrix interactions including but not limited to soluble ICAM-1 and soluble CD44, cartilage growth factors including but not limited to IGF-1 and TGF-β, free radical antagonists that reduce the deleterious effects of free radical formation within the joint including, but not limited to, superoxide dismutase and proteins or protein fragments that inhibit NO and NO synthase. Biologically active derivatives and fragments of the proteins encoded by these DNA sequences are also within the scope of the present invention.

Direct intraarticular injection of a DNA molecule containing the gene of interest into the joint results in transfection of the recipient target cells and hence bypasses the requirement of removal, in vitro culturing, transfection, selection, and transplantation of the DNA vector containing cells to promote stable expression of the heterologous gene of interest. Methods of presenting the DNA molecule to the target cells of the joint include, but are not limited to, association of the DNA molecule with cationic liposomes, subcloning the DNA sequence of interest in a retroviral vector as described throughout this specification, or the direct injection of the DNA molecule itself into the joint. The DNA molecule, regardless of the form of presentation to the knee joint, is preferably presented as a vector molecule, either as a recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the target cell or tissue. In vivo delivery of various viral and non-viral vectors to the rabbit knee joint are described in the Examples.

A preferred method of using the gene coding for the soluble interleukin-1 receptor (sIL-1R) of this invention involves employing recombinant techniques to generate a cell line which produces infectious viral particles containing the gene coding for sIL-1R. The producer cell line is generated by inserting the gene into a viral vector under the regulation of a suitable eukaryotic promoter, transfecting the viral vector containing the gene into the viral packaging cell line for the production of a viral particle capable of expressing the gene coding for sIL-1R, and infecting synovial or other cells of a mammalian host using the viral particle. The cells can be infected in culture (ex vivo) with viral particles and subsequently transplanted back into the joint, or can be infected in vivo by direct administration of the viral particles to the host joint. This method may be employed in both prophylactic and therapeutic treatment of joint pathologies in any joint area.

More specifically, a preferred method of using the gene coding for the sIL-1R involves introducing the viral particles obtained from the retroviral packaging cell line directly by intra-articular injection into a joint space of a mammalian host that is lined with synovial cells. In a preferred embodiment, synoviocytes recovered from the knee joint are cultured in vitro for subsequent utilization as a delivery system for gene therapy. It will be apparent that tissue other than synovial can be used. It would be possible to utilize other connective tissue sources, such as skin cells, or non-connective tissue cells, for in vitro culture techniques. The method of using the gene of this invention may be employed both prophylactically and in the therapeutic treatment of arthritis in any susceptible joint.

Another embodiment of this invention provides a method for preparing a gene encoding a product of interest including synthesizing the gene by a polymerase chain reaction, introducing the amplified coding sequence into a retroviral vector, transfecting the retroviral vector into a retrovirus packaging cell line and collecting viral particles from the retrovirus packaging cell line. A compound for parenteral administration to a patient in a therapeutically or prophylactically effective amount containing a gene encoding sIL-1R in a suitable pharmaceutical carrier is also provided for in the present invention. Such compounds can also be prepared using one or more of the other genes of interest disclosed herein.

The methods of the present invention involve transfection or transduction of numerous types of cells including connective tissue cells such as ligaments, cartilage, tendon, synovium, skin, bone, meniscus and intervertebral disc tissue, and non-connective tissue cells such as hematopoietic progenitor cells, stromal cells, bone marrow cells, myoblasts, leukocytes or mature lymphoid or myeloid cells, with a vector molecule containing any of the gene or genes disclosed throughout the specification. The transfected cells are recovered and injected into the host, such as in the joint space, bone marrow or blood stream, using techniques known and available to one of ordinary skill in the art. It will be possible, within the scope of this method, to use cells derived from autologous bone marrow instead of cells derived from donor bone marrow so as to modify rejection.

It is an object of the present invention to provide a method of introducing at least one gene encoding a product into at least one target cell of a mammalian host for use in treating the mammalian host.

It is an object of the invention to provide a method of introducing a gene encoding a product into at least one target cell of a mammalian host for a therapeutic use.

It is an object of the present invention to provide a method of introducing into the synovial lining cells of a mammalian arthritic joint at least one gene that encodes a protein having therapeutic properties.

It is an object of the present invention to provide an animal model for the study of connective tissue pathology.

It is an object of the present invention to provide a method of introducing by ex vivo or in vivo methods a gene coding for the sIL-1R that is capable of binding to and neutralizing substantially all isoforms of interleukin-1, including interleukin-1 alpha and interleukin-1 beta.

It is an object of the present invention to provide a method of introducing by ex vivo or in vivo methods a gene coding for IRAP or a biologically active derivative thereof, which is a competitive inhibitor of and therefore substantially neutralizes all isoforms of interleukin-1, including interleukin-1 alpha and interleukin-1 beta.

It is an object of the present invention to provide a method of introducing by ex vivo or in vivo methods a gene in a mammalian host that is capable of binding to and neutralizing substantially all isoforms of interleukin-1 and thus, substantially resist the degradation of cartilage and protect surrounding soft tissues of the joint space.

It is an object of the present invention to provide a method of introducing by ex vivo or in vivo methods a gene coding for the sIL-1R that is capable of binding to and neutralizing substantially all isoforms of interleukin-1 for the prevention of arthritis in patients that demonstrate a high susceptibility for developing the disease.

It is an object of the present invention to provide a method of introducing by ex vivo or in vivo methods a gene coding for IRAP that is capable of acting as c Competitive inhibitor of and therefore substantially neutralizes all isoforms of interleukin-1 for the prevention of arthritis in patients that demonstrate a high susceptibility for developing the disease.

It is an object of the present invention to provide a method of introducing by ex vivo or in vivo methods a gene coding for an sIL-1R that is capable of binding to and neutralizing substantially all isoforms of interleukin-1 for the treatment of patients with arthritis.

It is an object of the present invention to provide a method of introducing by ex vivo or in vivo methods a gene coding for IRAP or a biologically active derivative thereof, which is a competitive inhibitor of and therefore substantially neutralizes all isoforms of interleukin-1 for the treatment of patients with arthritis.

It is an object of the present invention to provide a method of introducing by ex vivo or in vivo methods a gene or genes that address the chronic debilitating pathophysiology of arthritis.

It is a further object of the present invention to provide a compound for parenteral administration to a patient which comprises a gene encoding sIL-1R in a suitable pharmaceutical carrier.

It is a further object of the present invention to provide a compound for parenteral administration to a patient which comprises a gene encoding IRAP in a suitable pharmaceutical carrier.

These and other objects of the invention will be more fully understood from the following description of the invention, the referenced drawings and the claims.

BRIEF DESCRIPTION OF THE DRAWINGS

FIGS. 8A–8C show the amino acid and nucleotide sequence of the human (SEQ ID NOS 1 and 2) and mouse (SEQ ID NOS 3 and 4) interleukin-1 receptors.

On day 4, knees were lavaged with 1 ml saline. On day 7, rabbits were killed and the knees again lavaged. The concentrations of human IRAP in the lavage fluids were determined by ELISA using a commercial kit (R&D Systems, Minneapolis, Minn.). Values given are means±S.E. Numbers of knees are shown above each column. Asterisks denote values which differ at p<0.05 (t-test).

Figure 15:
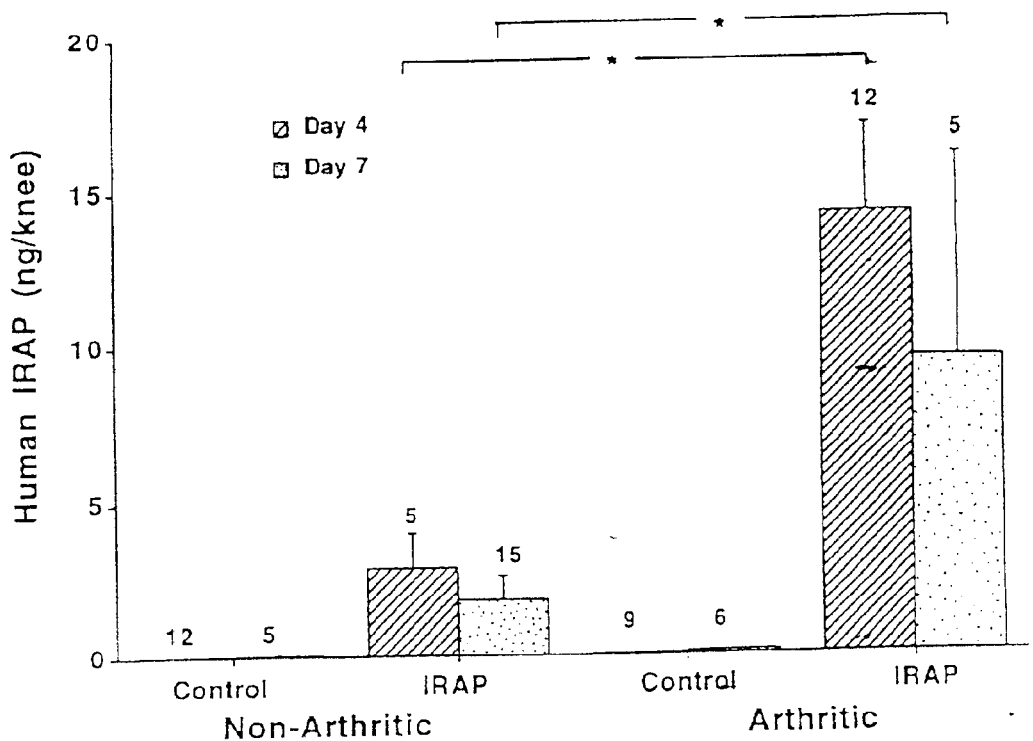
FIG. 15 shows expression of human IRAP in normal and arthritic knees of rabbits. Antigen-induced arthritis was initiated by injecting 5 mg ovalbumin into one knee joint (arthritic knee) of pre-sensitized rabbits on day 1. The contralateral knee (non-arthritic knee) received carrier solution only. On day 2, autologous synoviocytes ($10^7$/knee in 1 ml saline) were transferred to selected knee joints by intraarticular injection. Certain non-arthritic knees and arthritic knees received cells transduced with the human IRAP gene. Other non-arthritic and arthritic knees received untransduced cells or cells transduced with lac Z and $neo^r$ genes (controls). As the results obtained with these two types of control cells were indistinguishable, they have been pooled in the figures. Detailed methods for synoviocyte culture, transduction and intraarticular implantation are disclosed throughout this specification.
Figure 16:
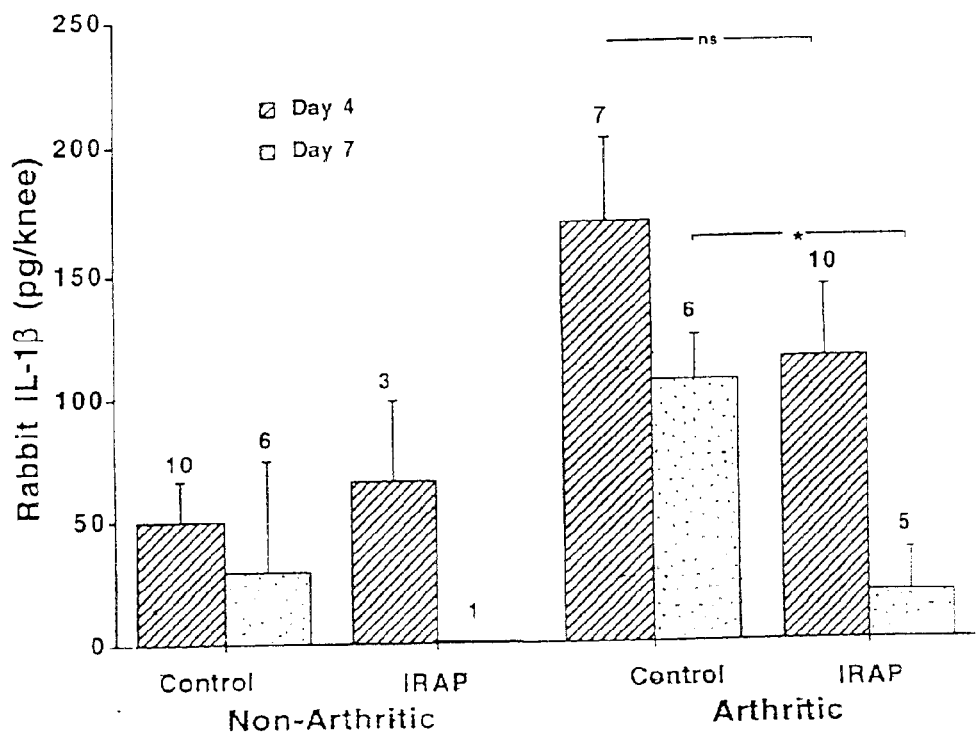

FIG. 16 shows concentrations of rabbit IL-1β in the normal and arthritic knee joints of rabbits. Experimental conditions were identical to those described in FIG. 15. However, lavage fluids were assayed for rabbit IL-1α and rabbit IL-1β by RIA using a commercial kit (Cytokine Sciences, Boston, Mass.). Low levels of IL-1β are present in non-arthritic knees as a reflection of the slight inflammatory effects provoked by intraarticular injection. No IL-1α was detectable in any of the samples. Values given are means±S.E. Numbers of knees are shown above each column. Asterisks denote values which differ at p<0.05 (t-test).

Figure 17A:
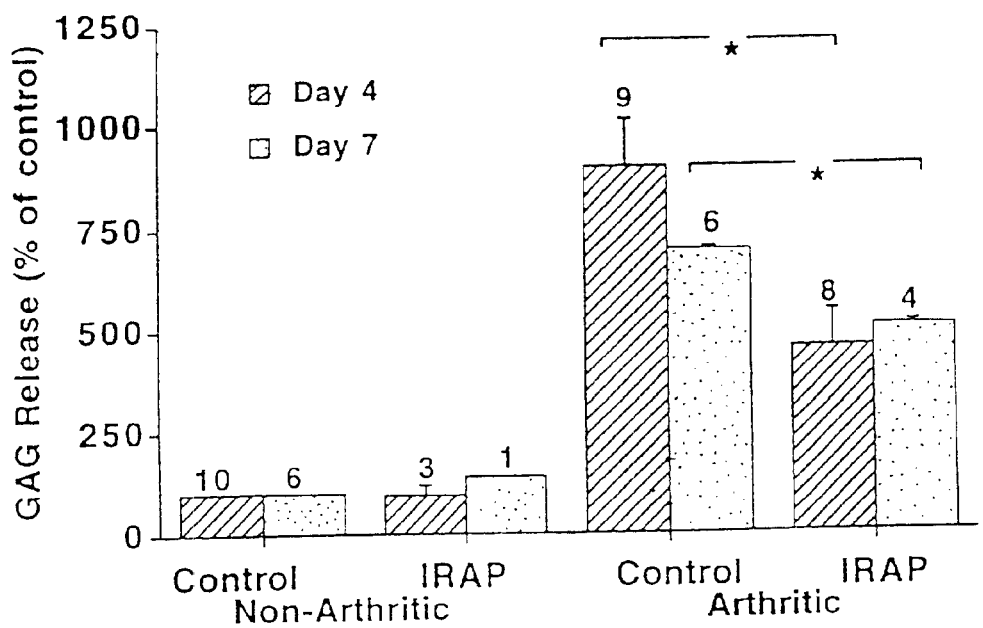
Figure 17B:
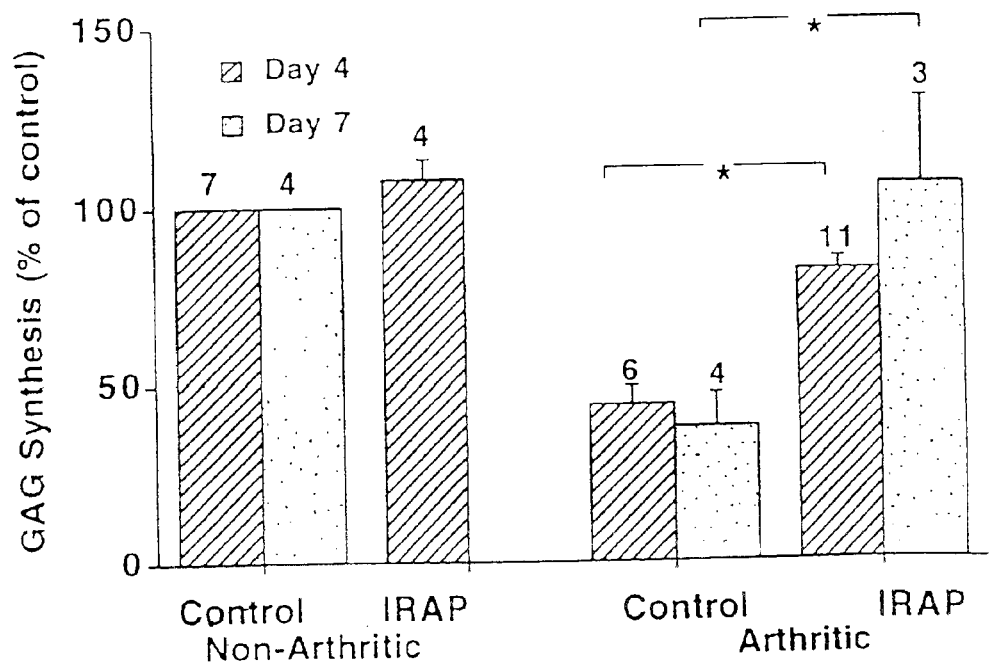

FIGS. 17A–B shows the effect of IRAP gene transfer on cartilage matrix metabolism. Experimental conditions were as described for FIG. 15, except that rabbits were killed both at days 4 and 7. GAG concentrations in the lavage fluids (FIG. 17A) were measured spectrophotometrically by the dimethymethylene blue assay (Farndale, et al., Biochim. Biophys. Acta. 883: 173–177 (1986)). Fragments of articular cartilage were shaved from the femoral condyles of the knees and GAG synthesis (FIG. 17B) was measured as the uptake of $^{35}SO_4^{2-}$ into macromolecular material as described (Taskiran, et al., Biochem. Biophys. Res. Commun. 200:142–148 (1994)). Results are shown in each case as percent of control values given are means±S.E. Numbers of knees are shown above each column.

Figure 18:
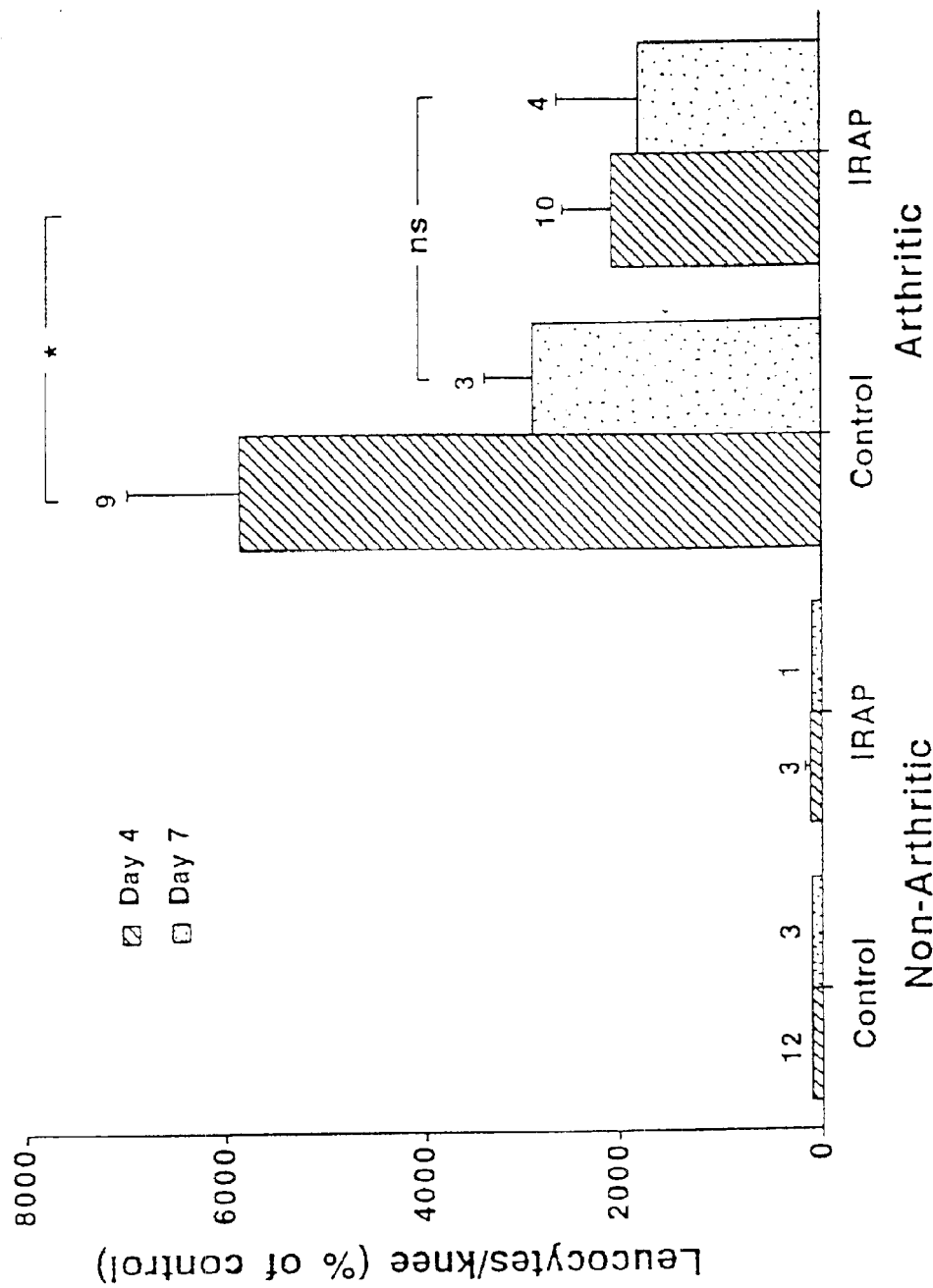

FIG. 18 shows effects of IRAP gene transfer on leukocytosis. Experimental conditions were identical to those described in FIG. 15. Numbers of leukocytes in the lavage fluids were determined with a hemocytometer. Values shown are means±S.E. Numbers of knees are shown above each column. Asterisks denote values which differ at p<0.05 (t-test).

FIGS. 19A–D shows intraarticular expression of hIL-1β and its pathogenic effects determined according to the methods of Example XVI.

Figure 20:
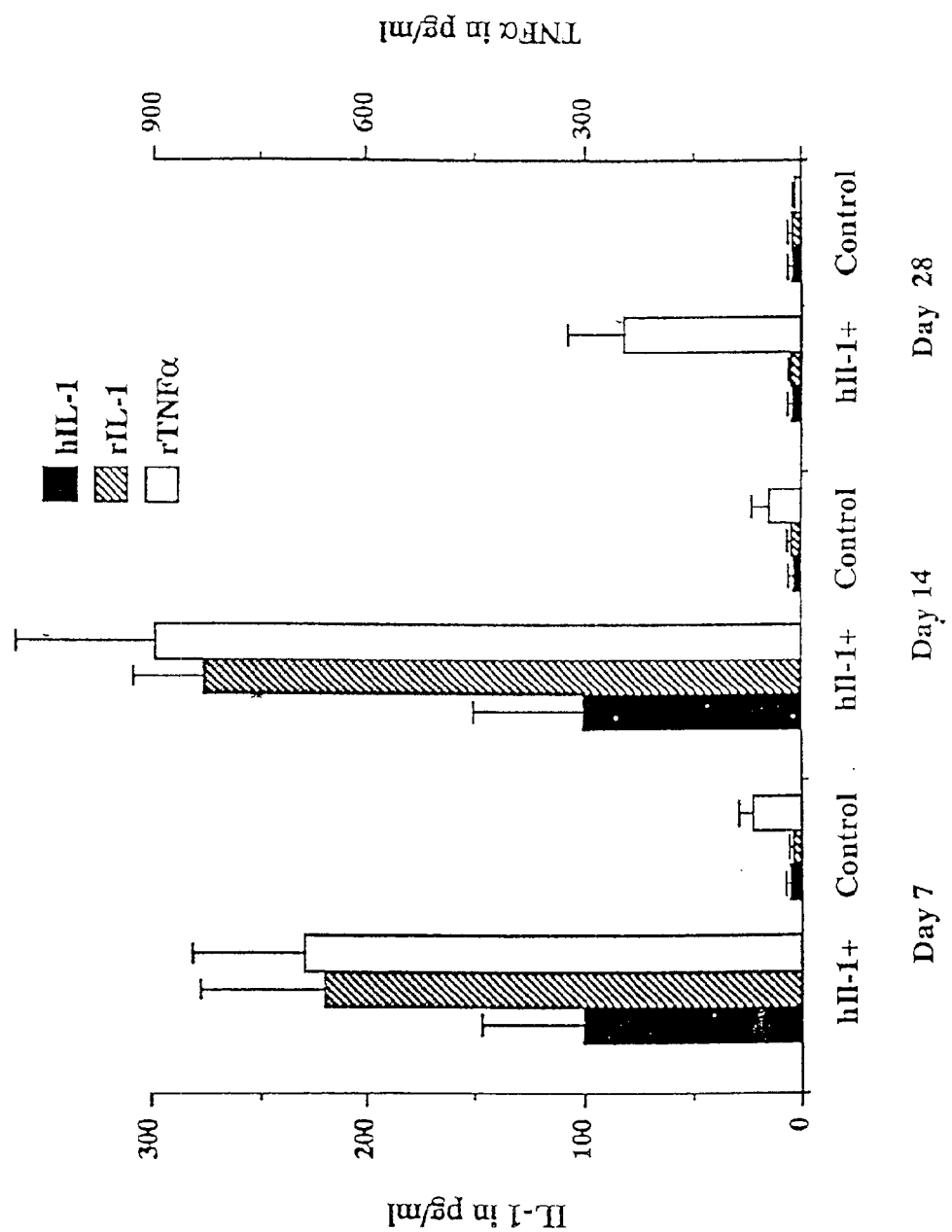

FIG. 20 shows levels of human (h), rabbit (r) IL-1β and rabbit (r) TNF-α recovered in lavage fluids determined according to the methods of Example XVI. All values are expressed as the mean±S.E.M.

FIGS. 21A–D shows detection of hIL-1β expression in vivo and its gross to pathology determined according to the methods of Example XVI.

FIGS. 22A–F shows local and systemic effects following intraarticular transplantation of autologous hIL-1β+ synoviocytes determined according to the methods of Example XVI. $2.5 \times 10^6$ naive synoviocytes (Control) or hIL-1β+synoviocytes (hIL-1) were autografted into the right and left knees, respectively, of twelve rabbits at day 0. Three rabbits were sacrificed at day 7, 4 at day 14, and 5 at day 28. For A, D, E and F each time point reflects measurements taken on remaining rabbits prior to sacrifice; B, and C reflect results obtained from rabbits sacrificed at that time point.

FIGS. 23A–H shows joint histology following expression of hIL-1β determined according to the methods of Example XVI. FIGS. 23 (A)–(F) are synovial sections stained with hematoxylin and eosin; (G) and (H) are sections of femoral condyles stained with toluidine blue.

Figure 24:
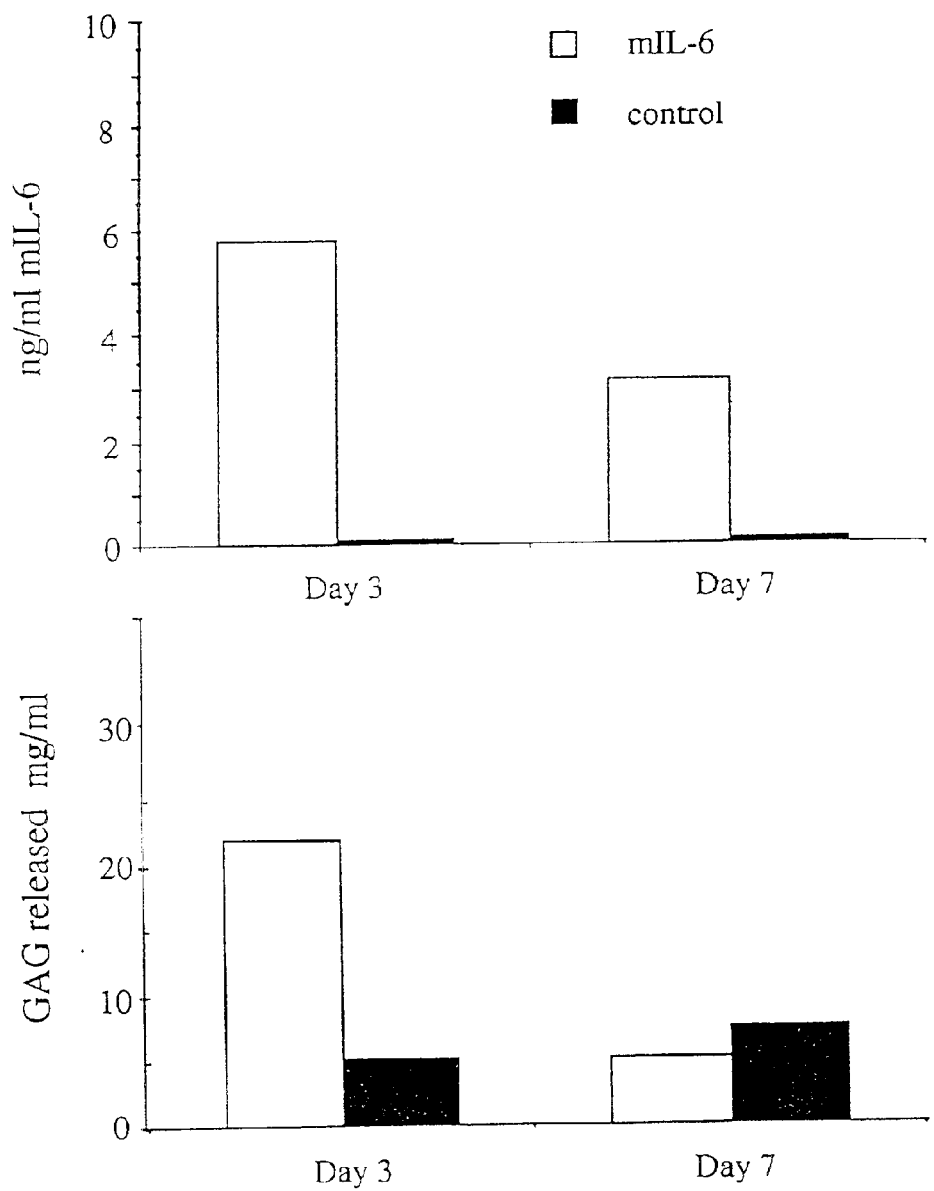

FIG. 24 upper panel shows the intraarticular expression levels of mIL-6 delivered by ex vivo gene transfer and FIG. 24 lower panel shows the effect of mIL-6 on GAG release, determined according to the methods of Example XVIII.

Figure 25:
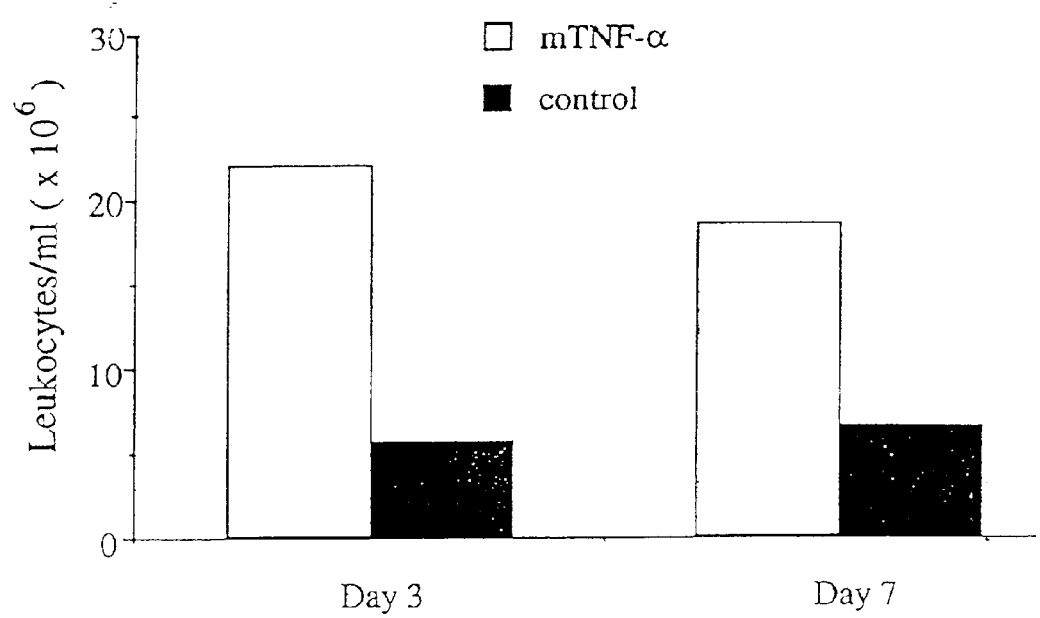
Figure 25:
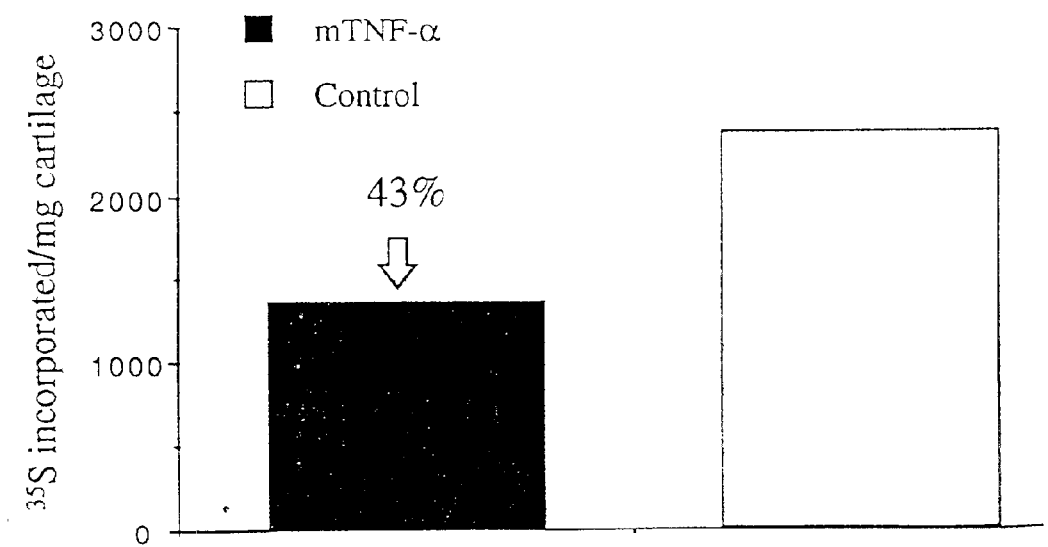

FIG. 25 upper panel shows the intraarticular elevation in leukocyte infiltration and FIG. 25 lower panel shows the depression of GAG synthesis rates due to over expression of mTNF-α by ex vivo delivery determined according to the methods of Example XVIII.

DETAILED DESCRIPTION OF THE INVENTION

As used herein, the term "patient" includes members of the animal kingdom including but not limited to human beings.

As used herein, the term "mammalian host" includes mammalian members of the animal kingdom including but not limited to human beings.

As used herein, the term "target cells" refers to cells that are targeted for transfection with the gene or genes encoding the product(s) of interest. Target cells can be either cells that are removed from a host and cultured with the gene(s) in vitro and returned to a host in an ex vivo methodology, or cells that are in the host and are transduced or transfected in vivo. Generally a target cell when used in reference to ex vivo methods is any cell that, when injected into a joint of a patient, will survive and express the gene. When used in reference to in vivo methods, a target cell is any cell capable of being transduced or transfected with one or more genes of interest and which will subsequently express the gene. Target cells include both connective tissue cells and non-connective tissue cells, as those terms are defined below.

As used herein, the term "connective tissue" includes but is not limited to a ligament, a cartilage, a tendon, a synovium, skin, bone, meniscus and intervertebral disc tissue of a mammalian host.

As used herein, the term "non-connective tissue" includes but is not limited to hematopoietic progenitor cells, stromal cells, bone marrow cells, leukocytes, and lymphoid or myeloid cells of a mammalian host.

As used herein, the terms "gene", "DNA sequence" or "product" "of interest" refer to genes, DNA sequences or the products they encode that are introduced to the host according to any of the methods of the present invention. For methods used in the therapeutic or prophylactic treatment of a host, the products of interest would be those proteins or peptides, or fragments or derivatives thereof, that have therapeutic and/or prophylactic properties. For methods used in the animal model, the products of interest would be those proteins or peptides, or fragments or derivatives thereof, that have a pathologic effect on the host, contributing to one or more of the deleterious effects of connective tissue disorders.

As used herein, the term "therapeutic" refers to the ability of a gene, product, protein, peptide, method and the like to alleviate at least on symptom of a connective tissue disorder, or the benefit realized from such alleviation. The term "prophylactic" refers to the ability of a gene, product, protein, peptide, method and the like to prevent or at least retard the onset of at least one symptom of a connective tissue disorder, or the benefit realized from such action.

As used herein, the term "enhanced therapeutic benefit" refers to the therapeutic benefit realized when more than one gene of interest is introduced to a host at the same time; the enhanced therapeutic benefit is greater than the therapeutic benefit of each of the genes administered separately. The benefit can be either additive or synergistic.

As used herein, the term "DC-chol" means a cationic liposome containing cationic cholesterol derivatives. The "DC-chol" molecule includes a tertiary amino group, a medium length spacer arm (two atoms) and a carbamoyl linker bond as described in *Biochem. Biophys. Res. Commun.*, 179:280–285 (1991), X. Gao and L. Huang.

As used herein, "SF-chol" is defined as a type of cationic liposome.

As used herein, the term "biologically active" used in relation to liposomes denotes the ability to introduce functional DNA and/or proteins into the target cell.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As will be appreciated by those skilled in the art, a fragment or derivative of a nucleic acid sequence or gene that encodes for a protein or peptide can still function in the same manner as the entire wild type gene or sequence. Likewise, forms of nucleic and sequences can have variations as compared with the wild type sequence, while the sequence still encodes a protein or peptide, or fragments thereof, that retain their wild type function despite these variations. Similarly, derivatives of the genes and products of interest used in the present invention will have the same biological effect on the host as the non-derivatized forms. Examples of such derivatives include but are not limited to dimerized or oligomerized forms of the genes or proteins, as wells as the genes or proteins modified by the addition of an immunoglobulin (Ig) group. Proteins, protein fragments or derivatives thereof also can experience deviations from the wild type form while still functioning in the same manner as the wild type form. Biologically active derivatives or fragments, when referring to the genes and/or DNA sequences described herein, are therefore also within the scope of the present invention.

One skilled in the art could test for the biological activity of a derivative or fragment of these genes/sequences/proteins by various methods known to those skilled in the art.

To determine if a fragment or derivative of IRAP is biologically active, a bioassay can be performed; if the compound blocks the ability of interleukin-1 to cause inflammation and cartilage breakdown, the derivative or fragment is a biologically active derivative or fragment of IRAP. Similarly, a bioassay can be performed to determine if a fragment or derivative of soluble interleukin-1 receptor protein is biologically active by determining whether the compound blocks the ability of interleukin-1 to cause inflammation and cartilage breakdown. To determine if a fragment or derivative of sTNF-αR is biologically active, a bioassay can be performed; if the compound prevents cell death in an L929 cell line in response to TNF-α, the fragment or derivative is biologically active. To determine if a fragment or derivative of a proteinase inhibitor is biologically active, a bioassay can be performed to determine whether the action of a proteinase is inhibited, such as by monitoring the rate of breakdown of a proteinaceous substrate. Inhibition of the proteinase would indicate biological activity. For example, the biological activity of a TIMP matrix metalloproteinase inhibitor can be determined by its ability to inhibit the activity of matrix metalloproteinases, as assayed by methods described by Watanabe et al., *Exp. Cell*

*Res.*, 167:218–226 (1986). To determine if a fragment or derivative of a therapeutic cytokine is biologically active, a bioassay can be performed to determine if the cytokine has a therapeutic or prophylactic effect in inhibiting any of the symptoms associated with a connective tissue disorder. For example, the biological activity of IL-6 can be determined by its ability to promote growth of B29 cells, as described by Arden et al., *Eur. J. Immunol.*, 17:1411–1416 (1987). The biological activity of IL-10 or vIL-10 can be determined by the ability of derivatives or fragments of these compounds to inhibit the production of nitric oxide by activated macrophages. To determine if a fragment or derivative of a growth hormone or a growth factor is biologically active, bioassays can be performed as taught by Taskiran et al., *Biochem. Biophys. Res. Commun.*, 200:142–148 (1994); biologically active derivatives or fragments will demonstrate increased proteoglycan synthesis by cartilage. To determine if a fragment or derivative of an anti-adhesion molecule is biologically active, a bioassay can be performed to determine the ability of the derivative or fragment to inhibit adhesion. To determine if a fragment or derivative of a free radical antagonist is biologically active, a bioassay can be performed to determine the ability of the fragment or derivative to inhibit the production of free radicals. To determine if a derivative or fragment of CTLA4 is biologically active, a bioassay can be performed to determine if the compound has the ability to bind to cells expressing B7.1, in which case it would be active. To determine if a derivative or fragment of FasL is biologically active, a bioassay can be performed to determine if the compound has the ability to induce apoptosis of cells that express Fas, in which case it would be biologically active. To determine if a derivative or fragment of iNOS is biologically active, a bioassay can be performed to determine if the compound has the ability to synthesize NO, in which case it would be biologically active. Any other manner for determining biological activity known to those skilled in the art can also be used.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic or prophylactic effect.

Connective tissues are difficult to target therapeutically. Intravenous and oral routes of drug delivery that are known in the art provide poor access to these connective tissues and have the disadvantage of exposing the mammalian host body systemically to the therapeutic agent. More specifically, known intra-articular injection of joints provides direct access to a joint. However, most of the injected drugs have a short intraarticular half-life. The present invention solves these problems by introducing into the mammalian host genes encoding for proteins that may be used to treat the mammalian host. In a preferred embodiment, this invention provides a method for introducing into the connective tissue of a mammalian host genes encoding for proteins with anti-arthritic properties.

The present invention provides a method for introducing at least one gene encoding a product into at least one target cell of a mammalian host for use in treating the mammalian host, which comprises employing recombinant techniques to generate a vector containing one or more DNA sequences encoding one or more products of interest, and infecting the cell of the mammalian host using the recombinant vector. This method preferably includes introducing the gene encoding the product into at least one target cell of the mammalian host for a therapeutic or prophylactic use. Both in vivo and ex vivo methods can be used to introduce the gene of interest to the host.

One ex vivo method for treating a connective tissue disorder according to the present invention comprises generating a recombinant vector containing one or more DNA sequences encoding one or more genes of interest, or biologically active derivatives or fragments thereof; infecting a population of in vitro cultured target cells with the vector, resulting in a population of transduced target cells; and transplanting the transduced cells to the mammalian host, effecting subsequent expression of the protein or protein fragment within the host. Expression of the protein or protein fragment of interest is useful in reducing at least one deleterious joint pathology or indicia of inflammation normally associated with a connective tissue disorder. Expression of the DNA sequence can also have a protective effect. Any means known to those skilled in the art can be used to introduce the transduced target cells to the target joint space. Intraarticular injection is preferred.

Any type of connective tissue cell or non-connective tissue cells, as those terms are described herein, can be used. Preferably, if using connective tissue, synovial cells are used; more preferably, for treating a human patient, the patient's own cells, such as autologous synovial cells, are used. When ligament cells are used, preferably the ligament is the medial collateral ligament (MCL). Use of cells and/or tissue from the patellar tendon and hamstring are also within the scope of the invention. Preferably, if using non-connective tissue, stromal cells are used.

For the ex vivo methods, all of the non-connective tissue cells can be injected back into the bone marrow or bloodstream of the host following transduction. Both connective and non-connective tissue cells can be injected into the joint space, or any other area, of the host following transduction. For the in vivo methods, non-connective tissue cells can be targeted in the bone marrow, bloodstream, joint space, or any other area, of the host and connective tissue cells can be targeted to any area of the host, preferably in the joint space.

Use of numerous genes, and biologically active derivatives and fragments thereof, are within the scope of the invention. Any gene capable of maintenance and expression, and encoding a product having a therapeutic and/or prophylactic effect in the treatment of joint pathology can be used in the methods of treating a host. These genes and biologically active derivatives and fragments include, but are not limited to, DNA sequences encoding for one or more of: interleukin-1 receptor antagonist protein (IRAP); a Lac Z marker gene capable of encoding a beta-galactosidase; a soluble interleukin-1 receptor (sIL-1R); a soluble TNF-α receptor (sTNF-αR); a proteinase inhibitor; a therapeutic cytokine; CTLA4; FasL; an anti-adhesion molecule; and a free radical antagonist. Any other gene having therapeutic properties and DNA capable of maintenance and expression can also be used. These genes can be either commercially obtained through any supplier or can be made by one skilled in the art from cDNA libraries or through the reverse transcriptase polymerase chain reaction (RTPCR) method.

IRAP is a cytokine known to suppress the inflammatory responses caused by interleukin-1 in joint spaces. Introduction of IRAP to these spaces, therefore, causes a reduction in the inflammation associated with joint pathologies characterized as having IL-1 production. It is believed that the IRAP binds with the interleukin-1 receptors, thereby preventing binding of the IL-1 to the receptors and inhibiting the inflammatory effects caused when IL-1 binds to the receptors, although the inventors do not wish to be bound by this mechanism.

Similarly, soluble interleukin-1 receptors (sIL-1R) bind to IL-1 without transmitting a cellular response, thereby preventing IL-1 from binding to the native, cell surface receptors. Any sIL-1 receptor can be used, including but not limited to, Type I and Type II receptors; sIL-1R Type II receptors are preferred because they do not bind to IRAP, while Type I receptors do. The Type I sIL-1R is an 80 Kd glycoprotein that is present on T-lymphocytes, fibroblasts, and chondrocytes. The Type II sIL-1R is 67 Kd in size and is found predominantly on macrophages and pre-B-cells.

Soluble tumor necrosis factor-alpha receptor (sTNF-αR) binds TNF-α and prevents it from having a damaging effect on the connective tissue of a patient. TNF-α is a cytokine which is known to contribute to the pathological effects of connective tissue disorders. The sTNF-αR of the present invention can be of any type, including Type I and Type II. The Type I sTNF-αR is an 55 Kd glycoprotein and Type II sTNFα-R is 75 Kd in size. Both receptors are widely distributed on various cell types. Both the sIL-1R and sTNF-αR have been shown to alleviate at least some of the symptoms associated with connective tissue disorders.

Various proteinase inhibitors are also within the scope of the present invention. Proteinase inhibitors are substances that prevent the enzymatic breakdown of proteins. Both proteinase inhibitors and metalloproteinase inhibitors are within the scope of the invention; preferred proteinase inhibitors are tissue inhibitor of metalloproteinase (TIMP), TIMP-1, TIMP-2, TIMP-3 and TIMP-4, plasminogen activator inhibitors (PAIs) and serpins.

Cytokines are small proteins with the properties of locally acting hormones. They serve to communicate between cells in a paracrine manner, and may also act in an autocrine manner on the same cell that produces the cytokine(s). Certain cytokines are important in driving pathophysiological changes in arthritic joints, while other cytokines offer protective effects against these changes. Cytokines exhibiting a protective effect include various forms of interleukin (IL) including IL-4, IL-10 and IL-13; all of these cytokines act in an anti-inflammatory capacity, as an immunosuppressive agent, or exert an immunostimulatory effect, depending on the target cell. It is also believed that they protect against cartilage breakdown.

Viral IL-10 (vIL-10), another cytokine, is a variant of IL-10 produced by the Epstein Barr virus. This virally encoded gene product is also immuno-suppressive and anti-inflammatory.

Growth factors are types of cytokines that are antiarthritic in that they maintain synthesis of the cartilaginous matrix. Growth factors include, but are not limited to, transforming growth factor (TGF), TGF-β1, TGF-β2 and TGF-β3, fibroblast growth factor (FGF), aFGF and bFGF, insulin-like growth factor (IGF), IGF-1 and IGF-2. While the effect of certain growth factors is not known, IGF's are known to maintain the synthesis of the cartilaginous matrix, and promote cartilage repair.

Growth hormone, and at least some of the bone morphogenetic proteins (BMP) are also cytokines. Growth hormone is believed to act by inducing local synthesis of IGF-1, although the inventors do not wish to be bound by this mechanism. There are at least nine BMP's; the BMP's are members of the TGF-β super family. BMP's induce the formation of both bone and cartilage. BMP-2 and BMP-7 (also known as osteogenic protein-1 (OP-1)) have shown to be particularly promising in the therapeutic treatment of connective tissue disorders, and are therefore the preferred BMP's for use in the methods of the present invention.

As used herein, the term "cytokine" refers to all of the therapeutic cytokines described above.

CTLA4 is a surface molecule found on T-cells, which binds to a counter-ligand known as B7 on the surface of antigen-presenting cells (APC's). In its soluble form, CTLA4 binds to B7 and thereby prevents B7 from interacting with a co-stimulatory molecule known as CD28 on the surface of the T-cell. When B7-CD28 interactions are blocked in this way, T-cell activation and hence the immune response is prevented. There is evidence that this process can induce immune tolerance. CTLA4 is typically used in soluble form.

Fas ligand (FasL) is a cell surface protein that binds to another protein, called Fas, found on the surface of other cells, including lymphocytes. When FasL binds to Fas, the cell expressing Fas undergoes apoptosis. Soluble FasL may also induce apoptosis and may be used to kill lymphocytes, as well as other Fas$^+$ cells in synovium.

Various anti-adhesion molecules are also within the scope of the present invention. These molecules function by inhibiting cell-cell and cell-matrix interactions and have anti-inflammatory properties. Examples of such proteins, including their fragments and derivatives, are soluble ICAM-1 and soluble CD44.

The use of free radical antagonists is also within the scope of the present invention. These antagonists function to prevent the deleterious effects of free radical formation within the afflicted joint. Examples include but are not limited to the superoxide dismutase and proteins or protein fragments which inhibit NO and NO synthase.

Preferred genes for use in the present invention for eliciting a therapeutic and/or prophylactic benefit in a host include IRAP, sIL-1RI, sIL-1RII, sTNF-αRI, sTNF-αRII, TIMP-1, TIMP-2, TIMP-3, TIMP-4, PAIs, serpins, IL-4, IL-10, IL-13, IGF-1, IGF-2, vIL-10, CTLA4, BMP-1, BMP-2, BMP-3, BMP-4, BMP-5, BMP-6, BMP-7, FasL and their derivative forms. Use of other therapeutic genes is also within the scope of the present invention.

The scope of the present invention includes the use of one or more of the above-recited therapeutic genes in the therapeutic or prophylactic treatment of a connective tissue disorder. Genes encoding for more than one protein can be introduced through the same vector, as described below, or can be introduced through the use of different vectors, with each vector containing a different gene of interest. An unexpected discovery of the present invention is that the use of two or more genes together produces an enhanced therapeutic benefit. Particularly preferred for use together are genes encoding for sTNF-αR and sIL-1R. Other gene combinations are within the scope of the present invention as well. When administering two or more different genes through two or more different vectors or other means of delivery, each of the delivery means can be introduced simultaneously or can be introduced in succession. If in succession, introduction of the second, third, or greater genes is preferably done immediately following introduction of the first gene, to ensure that the highest levels of expression of each gene are achieved in the host at the same time.

Numerous methods for introducing one or more of the above-described DNA sequences to the host can be used. For example, both viral and nonviral vectors can be prepared, which contain the DNA sequence(s) of interest. A preferred embodiment of this invention includes employing as the viral vector a retroviral vector. More specifically, this method includes employing as the retroviral vector at least one material selected from the group consisting of MFG and pLJ. An MFG vector is a simplified Moloney murine leukemia virus vector (MoMLV) in which the DNA sequences encoding the pol and env proteins have been deleted so as to render it replication defective. An MFG vector can be prepared that contains one DNA sequence of interest. Two (DFG), three (TFG) or even more DNA sequences of interest can be included in the MoMLV. Thus, DFG and TFG are forms of MFG having multiple genes. For ease of reference, the term MFG, as used herein, includes any singular or multi-gene form of the vector. A pLJ retroviral vector is also a form of the MoMLV and is more fully described by Korman et al., *Proc. Nat'l Acad. Sci.*, 84:2150–2154 (1987), which description is hereby incorporated by reference.

In a preferred embodiment of this invention, a DNA sequence encoding a human interleukin-1 receptor antagonist protein (IRAP) or biologically active derivatives or fragments thereof is introduced to the host. The DNA sequence encoding IRAP or a biologically active derivatives or fragments thereof may be delivered to the connective tissue of a mammalian host by any combination of various vector strategies and transduction techniques disclosed throughout this specification. A preferred method of delivering IRAP to a target joint space involves delivery of the IRAP gene to the synovial lining of a mammalian host through use of the MFG retroviral vector with the ex vivo technique disclosed within this specification. A DNA sequence of interest encoding a functional IRAP protein or protein fragment is subcloned into a retroviral vector of choice, the recombinant vector is then grown to adequate titers and used to infect in vitro cultured synovial cells, and the transduced synovial cells, preferably autografted cells, are transplanted into the joint of interest, preferably by intra-articular injection.

Other preferred embodiments of this invention include employing a retroviral vector selected from the group consisting of MFG and pLJ and a DNA sequence encoding soluble interleukin-1 receptor, a soluble TNF-α receptor and vIL-10.

Any of the DNA sequences and biologically active derivatives or fragments described above can also be introduced to the host by methods other than retroviral vectors. In another embodiment of this invention, a method is provided for introducing at least one gene encoding a product into at least one target cell of a mammalian host for use in treating the mammalian host which comprises employing recombinant techniques to produce a viral vector containing the gene encoding for the product and infecting the target cell of the mammalian host using the viral vector containing the gene coding for the product, wherein the viral vector is at least one vector selected from the group consisting of an adeno-associated virus, an adenovirus, and a herpes virus, such as herpes simplex type-1 or herpes simplex type-2.

Yet another method of introducing at least one gene encoding a product into at least one target cell of a mammalian host for use in treating the mammalian host includes employing non-viral means for introducing the gene encoding for the product into the target cell. This method includes employing non-viral means selected from the group consisting of at least one liposome, $Ca_3(PO_4)_2$, electroporation, and DEAE-dextran. Direct injection of naked DNA can also be used. The liposome can be a material selected from the group consisting of DC-chol, SF-chol and numerous others known to those skilled in the art. It will be understood that these non-viral means for introducing the gene encoding for the product into the connective tissue cell are non-infectious delivery systems. An advantage of the use of a non-infectious delivery system is the elimination of insertional mutagenesis and virally induced disease. It will be appreciated by those skilled in the art that the viral vectors employing a liposome are not limited by cell division as is required for the retroviruses to effect infection and integration of target cells.

Biological means can also be used to deliver DNA sequences to target cells. A virus, preferably a pseudo-type retrovirus, can be altered so that it is capable only of delivery and maintenance within a target cell, but not retaining an ability to replicate within the target cell or tissue. One or more DNA sequences are introduced to the altered viral genome, so as to produce a viral genome that acts like a vector, and can be inserted into a host so that the product of interest will be subsequently expressed.

High levels of collagenase and other tissue metalloproteinases, such as stromelysin and gelatinase can be expressed in the presence of IL-1 within connective tissue. Collagenase, stromelysin, and gelatinase are inhibited by the proteins TIMP-1, -2, -3 and -4 ("Tissue Inhibitor of MetalloProteinases"). Therefore, another preferred embodiment of this invention includes providing the method employing viral or non-viral means which includes employing one or more forms of TIMP as the proteinase inhibitor. A gene encoding a TIMP protein or biologically active derivative or fragment threat could be delivered to the target connective tissue by any combination of means disclosed in this specification.

After effecting the infection of the target cell but before the transplanting of the infected cell into the mammalian host, the transduced target cells can be stored. It will be appreciated by those skilled in the art that the transduced target cells may be stored frozen in 10 percent DMSO in liquid nitrogen.

Another embodiment of this invention includes a method of introducing at least one gene encoding a product into at least one target cell of a mammalian host for use in treating the mammalian host as described above but by effecting the infection of the cell in vivo by introducing the DNA sequence coding for the product directly into the mammalian host. Preferably, this method includes effecting the direct introduction of the DNA sequence into the mammalian host by intraarticular injection. This method includes employing the method to substantially prevent a development of arthritis in a mammalian host having a high susceptibility of developing arthritis. This method also includes employing the method on an arthritic mammalian host for therapeutic use, such as to repair and regenerate connective tissue.

Another preferred method of the present invention involves direct in vivo delivery of the IRAP gene to the synovial lining of a mammalian host through use of either an adenovirus vector, adeno-associated virus (AAV) vector or herpes-simples virus (HSV) vector. A DNA sequence of interest encoding a functional IRAP protein or protein fragment is subcloned into the viral vector, the IRAP containing viral vector is then grown to adequate titers, and directed into the joint space, preferably by intra-articular injection. A retroviral-IRAP construct, such as MFG-IRAP may also be utilized to directly target previously inflamed connective tissue cells within the joint space.

Direct intraarticular injection of a DNA sequence containing the gene of interest into the joint results in transfection of the recipient target cells and hence bypasses the requirement of removal, in vitro culturing, transfection, selection, as well as transplanting the DNA vector containing—target cells to promote stable expression of the heterologous gene of interest. Methods of presenting the DNA molecule to the target cells include, but are not limited to, encapsulation of the DNA molecule into cationic liposomes, subcloning the DNA sequence of interest in a viral vector, such as a retroviral vector, as described throughout this specification, or the direct injection of the DNA molecule itself into the joint. The DNA molecule, regardless of the form of presentation to the knee joint, is preferably presented as a vector molecule, either as recombinant viral DNA vector molecule, a retroviral vector or a recombinant DNA plasmid vector molecule. Expression of the heterologous gene of interest is ensured by inserting a promoter fragment active in eukaryotic cells directly upstream of the coding region of the heterologous gene. One of the ordinary skill in the art may utilize known strategies and techniques of vector construction to ensure appropriate levels of expression subsequent to entry of the DNA molecule into the synovial tissue. In vivo delivery of various viral and non-viral vectors to the rabbit knee joint are described in Example XV.

Both the ex vivo and in vivo methods of the invention can be used in the therapeutic treatment of patients suffering from one or more of the symptoms associated with joint pathologies, and in the repair and/or regeneration of connective tissue effected by such pathologies. Any of the methods of delivery of one or more genes of interest can be used in conjunction with either the in vivo or ex vivo methodologies. All of the methods can also be used prophylactically, to prevent or retard onset of the symptoms of connective tissue disorder in patients susceptible to such disorders.

The methods of the present invention provide a means for introduction of one or more products of interest to the host. These products of interest are generally known in the art as being effective against the symptoms of connective tissue disorders. The amount of each product, in the form of the DNA sequence encoding the product, to introduce will vary from patient to patient depending on such factors as the size of the patient, the joint affected, the severity of the connective tissue disorder, the gene being used and whether the method is being used therapeutically or prophylactically. Therapeutic responses are typically seen based upon delivery of a vector or other delivery vehicle sufficient to give gene expression in the high pico- to low nanogram range. One skilled in the art can determine the amount of vector or other delivery means to administer to a patient to achieve these levels of expression based upon the factors listed above. Introduction of vectors, such as a retroviral vector, in normal titer (about $10^5$ cfu/ml) is typically sufficient but high titer concentrations (equal to or greater than about $10^7$ cfu/ml) are preferred.

A further embodiment of this invention provides for an animal model to study connective tissue pathologies and indices of systemic inflammation. This model utilizes either ex vivo or in vivo delivery of at least one gene or DNA sequence of interest encoding a product into a least one cell of a connective tissue of a mammalian host. Examples of joint pathologies which can be studied in the present invention include, but are not limited to, joint pathologies such as leukocytosis, synovitis, cartilage breakdown, suppression of cartilage matrix synthesis, edema, inflammation of the eyes, arteritis and rheumatoid nodules. Examples of indices of systemic inflammation include, but are not limited to, elevated erythrocyte sedimentation rate, fever, weight loss and increases in blood levels of C-reactive protein and IL-6.

A particular embodiment of the present invention which relates to such an animal model is utilization of the ex vivo based delivery of a DNA sequence encoding human IL-1β gene to the synovial lining of the rabbit knee. In this embodiment, the human IL-1β gene is subcloned into the MFG retroviral vector by known methods, resulting in MFG-IL-1β. This recombinant retroviral construct is used to transduce autologous synovial cells cultured in vitro. These transduced cells are then delivered to the rabbit knees as described throughout this specification. Delivery of the human IL-1β gene to the synovial lining of the rabbit knee in this fashion causes a severe, chronic, monarticular arthritis. Pathologies include leukocytosis, synovitis, cartilage breakdown and suppression of cartilage matrix synthesis. Various systemic indices of inflammation are also effected, including an increased erythrocyte sedimentation rate, fever and weight loss. This procedure can also be carried out using any other retroviral vector, viral vector, or non-viral or biological means.

In another example of this particular embodiment of the present invention, the human IL-1β gene is subcloned into a DNA plasmid vector, downstream of a CMV promoter. This CMV-IL-1β plasmid construct is associated with liposomes and delivered to a target joint space, such as described in Example X. Forty eight hours subsequent to injection 100 pg of hIL-1β was recovered from the knee joint area, demonstrating the efficacy of the present methods in delivering hIL-1β to a joint of interest.

An animal model as described and exemplified in this specification measures the ability of various gene therapy applications disclosed throughout this specification to withstand challenges from known causative agents (such as IL-1β) of joint pathologies and inflammatory side effects.

A method to produce an animal model for the study of connective tissue pathology is also contemplated by the present invention. As will be understood by those skilled in the art, over-expression of interleukin-1 in the joint of a mammalian host is generally responsible for the induction of an arthritic condition. This invention provides a method for producing an animal model using the above described gene transfer technology of this invention. Preferably, the method of this invention provides a method for producing such an animal model for arthritis. For example, constitutive expression of interleukin-1 in the joint of a rabbit following the method of gene transfer provided for by this invention leads to the onset of an arthritic condition. It will be appreciated by those skilled in the art that this rabbit model is suitable for use for the testing of therapeutic agents. This method includes introducing at least one gene encoding a product into at least one target cell of a mammalian host comprising (a) employing recombinant techniques to produce a viral vector which contains the gene encoding for the product and (b) infecting the target cell of the mammalian host using the viral vector containing the gene coding for the product for effecting the animal model.

Any gene known to contribute to one or more of the symptoms of connective tissue disorders can be used in the animal model. As with the therapeutic treatment methodology, more than one gene can be introduced. Genes suitable for use in the animal model methods of the present invention, therefore, include any genes which cause such a symptom, including but not limited to various forms of interleukin such as IL-1α, IL-1β, IL-2, IL-7 IL-8, IL-12, IL-15 and IL-17, TNF-α, TNF-β, iNOS and proteinases including but not limited to aggrecanase, or a matrix metalloproteinase selected from the group consisting of at least one collagenase, gelatinase and stromelysin. Inducible nitric oxide synthase (iNOS or NOSII) is an enzyme found in athritic joints, which catalyzes the formation of the radical nitric oxide (NO).

Any biologically active derivatives or fragments of these genes can also be used. One skilled in the art can test the biological activity of such derivatives or fragments by evaluating their ability to contribute to one or more of the deleterious symptoms associated with connective tissue disorders.

Non-viral means for introducing at least one gene encoding a product into at least one cell of a connective tissue of a mammalian host can also be used in the animal model embodiment. The non-viral means is selected from the group consisting of at least one liposome, $Ca_3(PO_4)_2$, electroporation, DEAE-dextran and injection of naked DNA. The genes described above can be introduced by any of these non-viral means.

Any of the viral or non-viral means described in conjunction with the therapeutic method can be used to effect delivery of the DNA sequence or sequences of interest in the animal model. Also, any of the connective or non-connective tissue cells can be targeted in the animal model, as described above for the therapeutic methods. It will be appreciated by those skilled in the art that introduction of any of the deleterious genes listed above will result in conditions mimicking those seen in an animal suffering from a connective tissue disorder. The afflicted animal can then be used to study potential methods for therapeutically treating such connective tissue disorders experienced by humans. Thus, the animal model of the present invention provides a correlatable means of studying connective tissue disorders.

EXAMPLES

The following examples are intended to illustrate the present invention, and should not be construed as limiting the invention in any way.

Example I

Packaging of AAV

The only cis-acting sequences required for replication and packaging of recombinant adeno-associated virus (AAV) vector are the AAV terminal repeats. Up to 4 kb of DNA can be inserted between the terminal repeats without effecting viral replication or packaging. The virus rep proteins and viral capsid proteins are required in trans for virus replication as is an adeno-associated virus helper. To package a recombinant AAV vector, the plasmid containing the terminal repeats and the therapeutic gene is co-transfected into cells with a plasmid that expresses the rep and capsid proteins. The transfected cells are then infected with adeno-associated virus and virus isolated from the cells about 48–72 hours post-transfection. The supernatants are heated to about 56° Centigrade to inactivate the adeno-associated virus, leaving an active virus stock of recombinant AAV.

Example II

Electroporation

The connective tissue cells to be electroporated are placed into Herpes buffer saline (HBS) at a concentration of about $10^7$ cells per ml. The DNA to be electroporated is added at a concentration of about 5–20 ug/ml of HBS. The mixture is placed into a cuvette and inserted into the cuvette holder that accompanies the Bio-RAD electroporation device (1414 Harbour Way South, Richmond, Calif. 94804). A range between about 250 and 300 volts at a capacitance of about 960 ufarads is required for introduction of DNA into most eukaryotic cell types. Once the DNA and the cells are inserted into the Bio-RAD holder, a button is pushed and the set voltage is delivered to the cell-DNA solution. The cells are removed from the cuvette and replated on plastic dishes.

Example III

Figure 1:
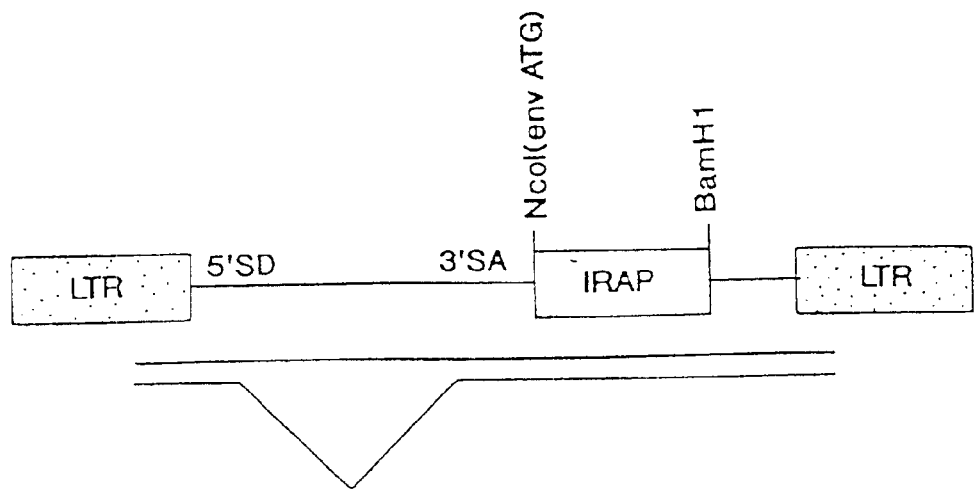
FIG. 1 shows the structure of the cDNA encoding the human interleukin-1 receptor antagonist protein (IRAP) gene inserted into the NcoI and BamHI cloning sites of the retroviral vector MFG.

The cDNA encoding the human interleukin-1 receptor antagonist (IRAP) was inserted into the NcoI and BamHI cloning sites of the retroviral vector MFG as shown in FIG. 1. Specifically, a PstI to BamHI fragment from the IRAP cDNA was linked to a synthetic oligonucleotide adapter from the NcoI site (representing the start site of translation for IRAP) to the PstI site (approximately 12 base pairs downstream from the NcoI site) to the MFG backbone digested at NcoI and BamHI in a three part ligation reaction. This three part ligation involving a synthetic oligo and two DNA fragments is well known by those skilled in the art of cloning. LTR means long terminal repeats, 5'SD means 5' splice donor, 3'SA means 3' splice acceptor. The straight arrow and the crooked arrow in FIG. 1 represent unspliced and spliced messenger RNAs respectively. IRAP is encoded by the spliced message.

Figure 2:
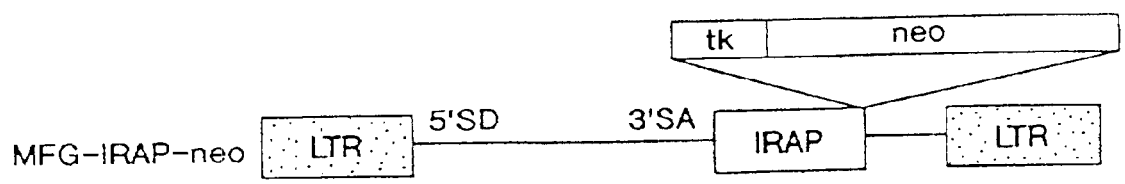
FIG. 2 shows the structure of the cDNA encoding the human interleukin-1 receptor antagonist protein (IRAP) gene with a selectable neo marker inserted into the retroviral vector MFG.
Figure 3:
FIG. 3 shows a micrograph of synovium recovered from the knee of a rabbit approximately one month after intra-articular injection of Lac $Z^+$, $neo^+$ synoviocytes employing the methods of this invention.

FIG. 2 shows the cDNA encoding the human interleukin-1 receptor antagonist protein (IRAP) with a selectable neo gene marker. FIG. 3 shows a low power micrograph of synovium recovered from the knee of a rabbit one month after intra-articular injection of Lac $Z^+$, neo$^+$ synoviocytes. Tissue was stained histochemically for the presence of beta-galactosidase. This micrograph counterstained with eosin revealed an area of intensely stained, transplanted cells demonstrating that these cells have colonized the synovial lining of the recipient joint.

Example IV

Animal Models

The methods of this invention of transferring genes to the synovia of mammalian joints permit the production and analysis of joint pathologies that were not previously possible. This is because the only other way of delivering potentially arthritogenic compounds to the joint is by intra-articular injection. Not only are such compounds quickly cleared from joints, but the effects of bolus injections of these compounds do not accurately mimic physiological conditions where they are constantly produced over a long period of time. In contrast, the gene transfer technologies of this invention permit selected proteins of known or suspected involvement in the arthritic process to be expressed intraarticularly over an extended period of time, such as for example, at least a three month period. The animal models of this invention therefore permit the importance of each gene product to the arthritic process to be evaluated individually. Candidate genes include, but are not restricted to, those coding for cytokines such as interleukin-1 alpha (IL-α), IL-1 beta (IL-1β) and TNF-alpha, (TNF-α) and matrix metalloproteinases such as collagenases, gelatinases and stromelysins.

Additionally, the gene transfer techniques of this invention are suitable for use in the screening of potentially therapeutic proteins. In this use, the animal models of the invention are initiated in joints whose synovia express one or more genes coding for potential anti-arthritic proteins. Candidate proteins include, but are not restricted to, inhibitors of proteinases such as the tissue inhibitor of metalloproteinases, and cytokines such as transforming growth factor-beta (TGF-β).

Example V

Method for Using Synoviocytes as a Delivery System for Gene Therapy

Rabbits are killed by intravenous injection of 4 ml nembutol, and their knees quickly shaved. Synovia are surgically removed from each knee under aseptic conditions, and the cells removed from their surrounding matrix by sequential digestion with trypsin and collagenase (0.2% w/v in Gey's Balanced Salt Solution) for about 30 minutes and about 2 hours, respectively. The cells recovered in this way are seeded into 25 cm² culture flasks with about 4 ml of Ham's $F_{12}$ nutrient medium supplemented with 10% fetal bovine serum, about 100 U/ml penicillin and about 100 µg/ml streptomycin, and incubated at about 37° in an atmosphere of 95% air, 5% $CO_2$. Following about 3–4 days incubation, the cells attain confluence. At this stage, the culture medium is removed and the cell sheet washed twice with approximately 5 mls of Gey's Balanced Salt Solution to remove non-adherent cells such as lymphocytes. The adherent cells are then treated with trypsin (0.25% w/v in balanced salt solution). This treatment detaches the fibroblastic, Type B synoviocytes, but leaves macrophages, polymorphionuclear leukocytes and the Type A synoviocytes attached to the Culture vessel. The detached cells are recovered, re-seeded into 25 cm² culture vessels at a 1:2 split ratio, medium is added and the culture returned to the incubator. At confluence this procedure is repeated.

After the third such passage, the cells are uniformly fibroblastic and comprise a homogeneous population of Type B synoviocytes. At this stage, cells are infected with the retroviral vector.

Following infection, cells are transferred to fresh nutrient medium supplemented with about 1 mg/ml G418 (GIBCO/BRL, P.O. Box 68, Grand Island, N.Y. 14072-0068) and returned to the incubator. Medium is changed every three days as neo cells die and the neo⁺ cells proliferate and attain confluency. When confluent, the cells are trypsinized and subcultured as described above. One flask is set aside for staining with X-gal to confirm that the neo⁺ cells are also Lac $Z^+$. When the subcultures are confluent, the medium is recovered and tested for the presence of IRAP, soluble IL-1R or other appropriate gene products as hereinbefore described. Producing synoviocyte cultures are then ready for transplantation.

The cells are recovered by centrifuging, washed several times by resuspension in Gey's Balanced Salt Solution and finally resuspended at a concentration of about $10^6$–$10^7$ cells/ml in Gey's Solution. Approximately 1 ml of this suspension is then introduced into the knee joint of a recipient rabbit by intra-articular injection. For this purpose a 1 ml syringe with a 25-gauge hypodermic needle is used. Injection is carried out through the patellar tendon. Experiments in which radiopaque dye was injected have confirmed that this method successfully introduces material into all parts of the joint.

Variations on the disclosed harvesting, culture and transplantation conditions in regard to the numerous examples presented within this specification will be evident upon inspection of this specification. Several tangential points may be useful to one practicing the ex vivo based gene therapy portion of the disclosed invention:

(1) If the yield of synoviocytes from the harvested synovial tissue is poor, the surgical technique may be at fault. The synovium has a strong tendency to retract when cut. Therefore, the inner capsule is grasped firmly, and with it the synovium, while excising this tissue. A small (about 2 mm) transverse incision can be made inferiorly, followed by sliding one point of the forceps into the joint space so that the synovium and inner capsule are sandwiched between the points of the forceps. The tissue is then excised without releasing the tissue thus preventing retraction of the synovium.

(2) A two compartment digestion chamber may be used to initially separate the cells from extracellular debris. In lieu of this choice, synovial tissue may be digested in a single chamber vessel and filtered through a nylon monofilament mesh of 45 µm pore size.

(3) When resuspending cells, the smallest amount of medium possible can be used to prevent formation of clumps of cells, which are difficult to separate once formed. EDTA in millimolar amounts can also be used to prevent clumps.

(4) During trypsinization, synoviocytes can lose the fusiform morphology that they possess in adherence, and assume a rounded shape. The cells initially will detach in clumps of rounded cells; one may allow the majority of cells to separate from each other before stopping trypsinization.

(5) Synoviocytes may be transduced with multiple transgenes by use of retroviral vectors containing multiple transgenes or by sequential transduction by multiple retroviral vectors. In sequential transduction, the second transduction should be made following selection, when applicable, and passage after the first transduction.

(6) As the synovium is a well-innervated structure, intra-articular injection can be painful, especially if done rapidly. Intra-articular injection of a 1 ml volume should take 10 to 15 seconds.

(7) In the animal model, the depth of the needle stick should not exceed 1 cm during intraarticular injection, and depression of the syringe plunger should meet with little to no resistance. Resistance to advancement of the syringe plunger indicates that the tip of the needle is not in the joint space.

(8) In the animal model, to retrieve a useful volume of the injected Gey's solution during joint lavage, the needle should not be inserted too deeply, otherwise it may penetrate the posterior capsule and may lacerate the popliteal artery. Firm massage of the suprapatellar, infrapatellar, and lateral aspects of the knee during aspiration helps to increase the amount of fluid recovered; in general, it should be possible to recover $\geq 0.5$ ml of fluid. When knees are badly inflamed, lavage is often difficult because of the presence of large numbers of leukocytes, fibrin, and other debris in the joint. The animal can be anesthetized or sacrificed and the Gey's solution recorded surgically.

Example VI

The method of Example V for producing generally uniformly fibroblastic cells of a homogeneous population of Type B synoviocytes was followed to effect growing cultures of lapine synovial fibroblasts. These growing cultures of lapine synovial fibroblasts were subsequently infected with an amphotropic retroviral vector carrying marker genes coding for beta-galactosidase (Lac Z) and resistance to the neomycin analogue G418 (neo⁺). Following infection and growth in selective medium containing about 1 mg/ml G418, all cells stained positively in a histochemical stain for beta-galactosidase.

Neo selected cells carrying the Lac Z marker gene were transplanted back into the knees of recipient rabbits to examine the persistence and expression of these genes in vivo. Two weeks following transplantation, islands of Lac $Z^+$ cells within the synovium of recipient knees were observed. This confirmed the ability of the method of this invention to introduce marker genes into rabbit synovia and to express them in situ.

Example VII

Neo-selected, Lac $Z^+$ synoviocytes were recovered from cell culture, suspended in Gey's Balanced Salt Solution and injected intra-articularly into the knee joints of recipient rabbits (about $10^5$–$10^7$ cells per knee). Contralateral control knees received only a carrier solution. At intervals up to 3 months following transplant, the rabbits were killed and their synovia and surrounding capsule recovered. Each sample may be analyzed in three ways. A third of the synovium was stained histochemically en masse for the presence of beta-galactosidase. A second portion may be used for immunocytochemistry using antibodies specific for bacterial beta-galactosidase. The final portion may be digested with trypsin and collagenase, and the cells thus recovered cultured in the presence of G418.

Staining of the bulk synovial tissue revealed extensive areas of Lac $Z^+$ cells, visible to the naked eye. Control synovia remained colorless. Histochemical examination of synovia revealed the presence of islands of cells staining intensely positive for beta-galactosidase. These cells were present on the superficial layer of the synovial lining, and were absent from control synovia. From such tissue it was possible to grow Lac $Z^+$, $neo^+$ cells. Cells recovered from control tissue were Lac $Z^-$ and died when G418 was added to the culture. This indicates that the transplanted, transduced synovial fibroblasts have successfully recolonized the synovia of recipient joints, and continue to express the two marker genes, Lac Z and neo. Maintaining intra-articular Lac Z and neo expression in transplanted synoviocytes has been effected for about 6 weeks using primary cells and about 2 weeks using the HIG-82 cell line.

Example VIII

Based upon the methods of the hereinbefore presented examples, and employing standard recombinant techniques well known by those skilled in the art, the human IRAP gene was incorporated into an MFG vector as shown in FIG. 1. Following the infection of synoviocyte cultures of rabbit origin with this viral vector, IRAP was secreted into the culture medium.

Figure 4:
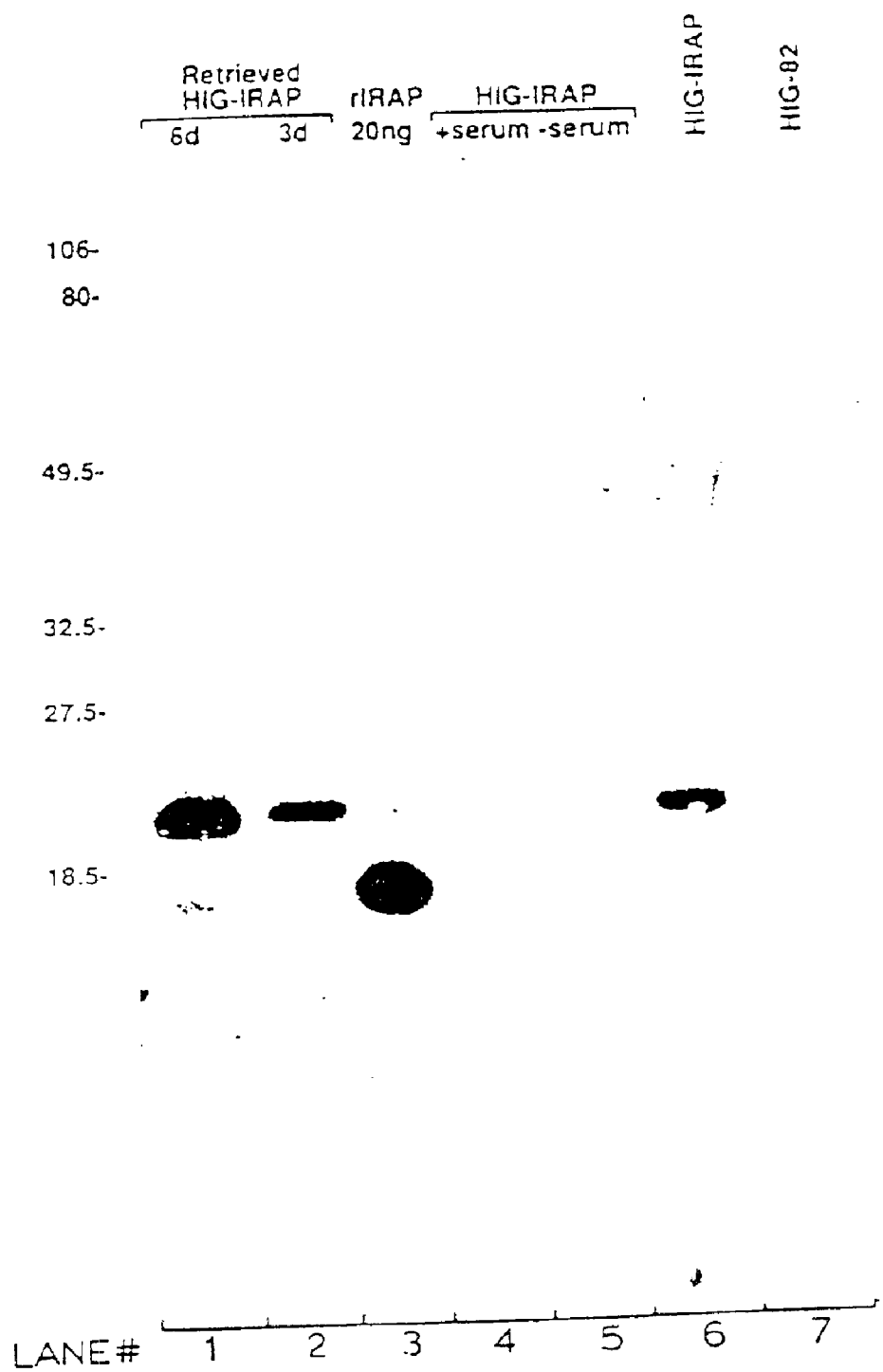
FIG. 4 shows a Western blot demonstrating the production of interleukin-1 receptor antagonist protein by four cultures of HIG-82 cells (Georgescu, et al., 1988, In Vitro 24: 1015–1022) infected using the method of this invention employing the MFG-IRAP viral vector.

Western blotting, well known by those skilled in the art, was carried out using an IRAP-specific rabbit polyclonal antibody that does not recognize human or rabbit IL-1 alpha or IL-1 beta, or rabbit IRAP. FIG. 4 shows a Western blot which sets forth the production of IRAP by four cultures of HIG-82 cells infected with MFG-IRAP. Three forms of the IRAP are present: a non-glycosylated form which runs with recombinant standards, and two larger glycosylated forms. The results of the Western blotting shown in FIG. 4 demonstrated that IRAP was produced by HIG-82 synoviocyte cell line (Georgescu, 1988, In Vitro 24: 1015–1022) following infection with the MFG-IRAP vector of this invention. The Western blotting of FIG. 4 shows the IRAP concentration of the conditioned medium is as high as 50 ng/ml. This is approximately equal to 500 ng IRAP/$10^6$ cells/day. Lane 1 and Lane 2 of FIG. 4 show that the recipient synovia tissue secrete substantial amounts of HIG-IRAP at 3 days (Lane 2) and 6 days (Lane 1). Lane 3 shows human recombinant IRAP. Lane 6 indicates that rabbit synovial cells produce a larger glycosylated version of this molecule after infection with MFG-IRAP. Lane 7 indicates that native rabbit synovial cells do not produce this glycosylated form.

Figure 5:
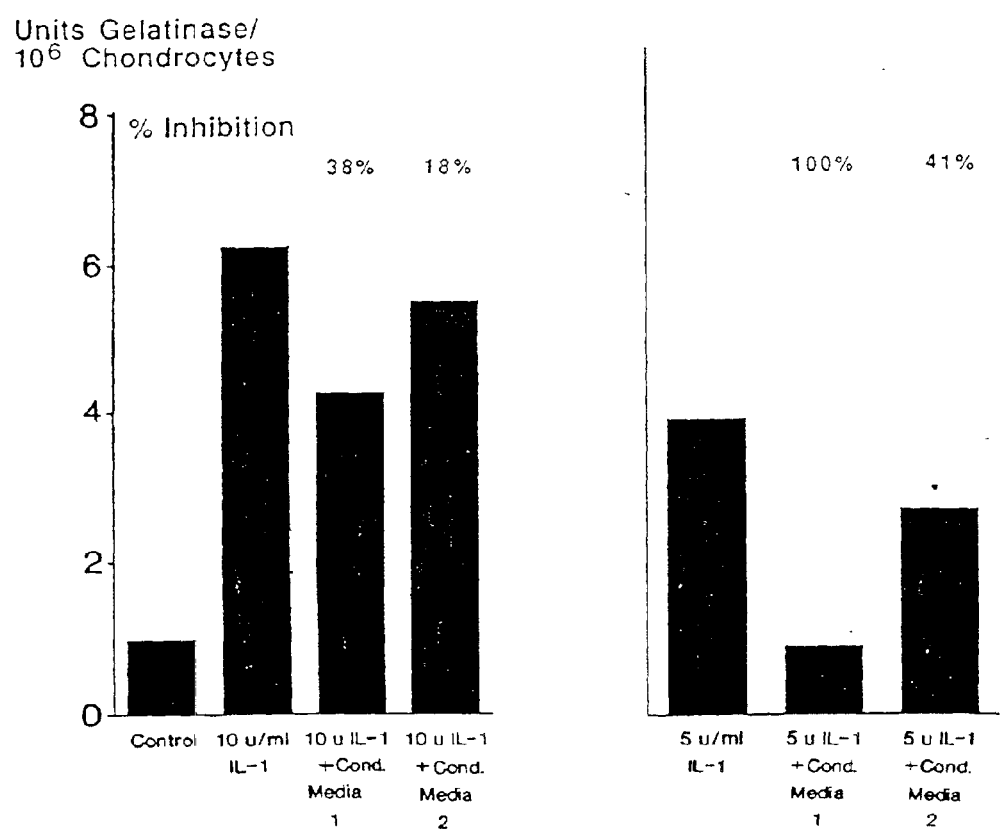
FIG. 5 shows data demonstrating the inhibition of gelatinase production by chondrocytes by the addition of medium conditioned by MFG-IRAP infected HIG-82 cells.

FIG. 5 shows that medium conditioned by IRAP$^+$ synoviocytes blocks the induction of matrix metalloproteinases in articular chondrocytes exposed to recombinant human IL-1 beta. Chondrocytes normally secrete 1 U/$10^6$ cells, or less, gelatinase into their culture media. FIG. 5 shows that when to about 5 U/ml or 10 U/ml IL-1 are added, gelatinase production increases to over 4 U and 6 U/$10^8$ cells, respectively. Addition of medium conditioned by MFG-IRAP-infected HIG-82 cells employed by the method of this invention suppressed gelatinase production by IL-1 treated chondrocytes. With 5 U/ml IL-1 (FIG. 5, right panel) inhibition was 100% for one culture and 41% for the other. With 10 U/ml IL-1, inhibition was reduced to 38% and 18% (FIG. 5, left panel) as is expected of a competitive inhibitor. These data demonstrate that the IRAP produced by HIG-82 cells infected with MFG-IRAP is biologically active.

Example IX

This example demonstrates the uptake and expression of Lac Z gene by synoviocytes using infection by a liposome (lipofection). A six well plate containing synoviocyte cultures were transduced with the Lac Z gene by lipofection. The content of each well is as follows:

| | |
|---|---|
| Well 1 | Control cells, treated with liposomes alone |
| Well 2 | Control cells, treated with DNA alone |
| Well 3 | DNA + 150 nmole liposomes |
| Well 4 | DNA + 240 nmole liposomes |
| Well 5 | DNA + 300 nmole liposomes |
| Well 6 | DNA + 600 nmole liposomes |

Figure 6:
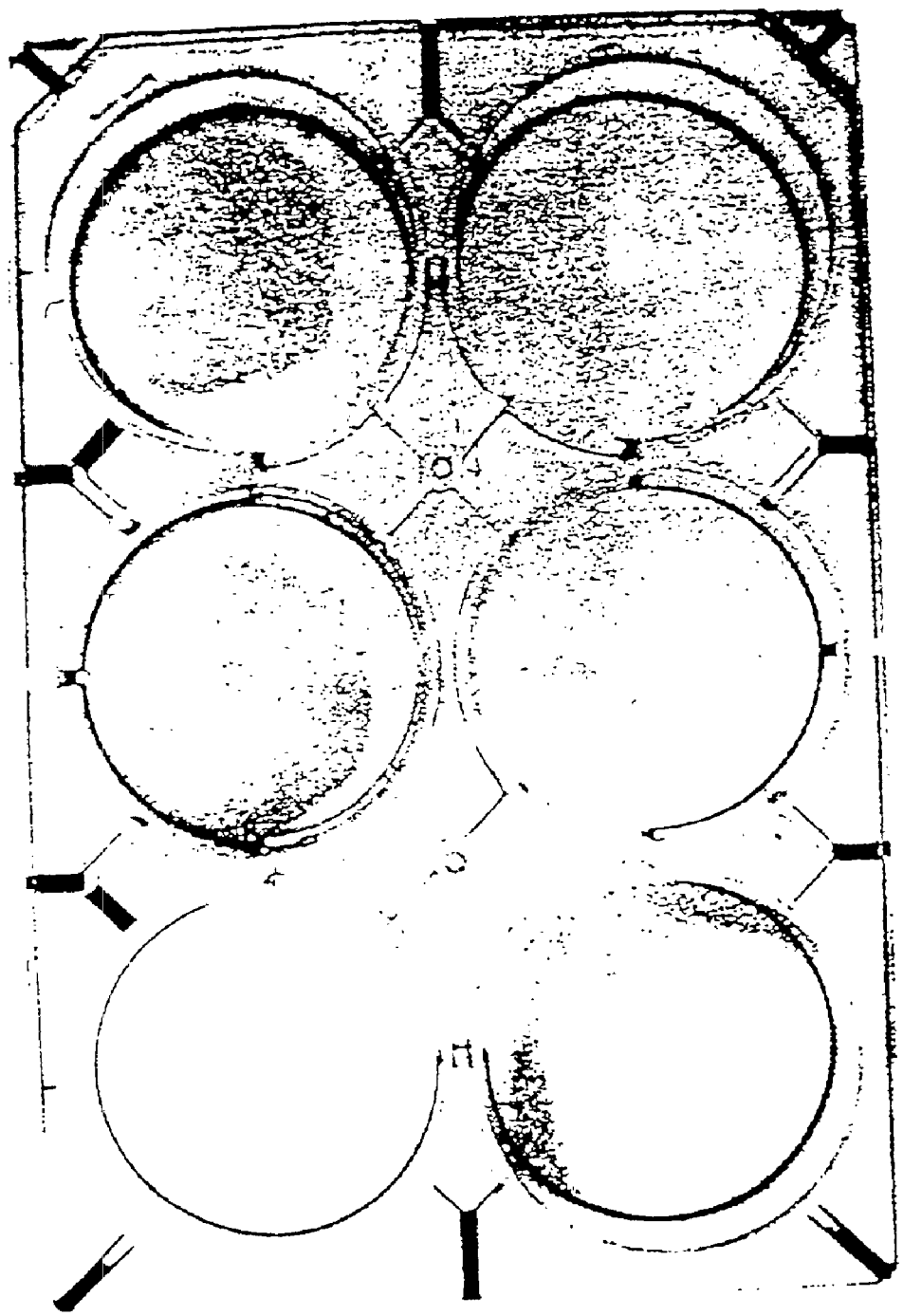
FIG. 6 shows the uptake and expression of the Lac Z gene by synoviocytes using lipofection. Well 1—Control cells, treated with liposomes alone; Well 2—Control cells, treated with DNA alone; Well 3—DNA+150 nmole liposomes; Well 4—DNA+240 nmole liposomes; Well 5—DNA+300 nmole liposomes; Well 6—DNA+600 nmole liposomes.

Wells 3–6 containing sub-confluent cultures of synovial fibroblasts were transfected with 6 ug of DNA complexed with 150–600 nmoles/well of "DC-chol" liposome or in the alternative, with "SF-chol". Three days later, cells were stained histochemically for expression of beta-galactosidase (FIG. 6).

Table 1 shows the results of using the liposomes "DC-chol" and "SF-chol" in converting synoviocyte cultures to the Lac $Z^+$ phenotype without selection. Table 1 sets forth that the "DC-chol" liposome in a concentration of about 300 nmole/well converted generally 30% of the synovial cells in synoviocyte cultures to the Lac $Z^+$ phenotype without selection. Reduced expression was shown in Well 6 for "DC-chol" due to the toxic effect of the high liposome concentration.

TABLE 1

| Liposome, nmole/well | % Lac $Z^+$ Cells | |
|---|---|---|
| | DC-chol | SF-chol |
| 150 | 10 | 0.5 |
| 240 | 22 | 1.0 |
| 300 | 30 | 2.8 |
| 600 | NA | 3.5 |

In another embodiment of this invention, a gene and method of using this gene provides for the neutralization of interleukin-1. Interleukin-1 is a key mediator of cartilage destruction in arthritis. Interleukin-1 also causes inflammation and is a very powerful inducer of bone resorption. Many of these effects result from the ability of interleukin-1 to increase enormously the cellular synthesis of prostaglandins, and a various proteinases including collagenase, gelatinase, and stromelysin, a plasmiinogen activator and aggrecanase. The catabolic effects of interleukin-1 upon cartilage are exacerbated by its ability to suppress the synthesis of the cartilaginous matrix by chondrocytes. Interleukin-1 is present at high concentrations in synovial fluids aspirated from arthritic joints and it has been demonstrated that intra-articular injection of recombinant interleukin-1 in animals causes cartilage breakdown and inflammation.

Figure 7:
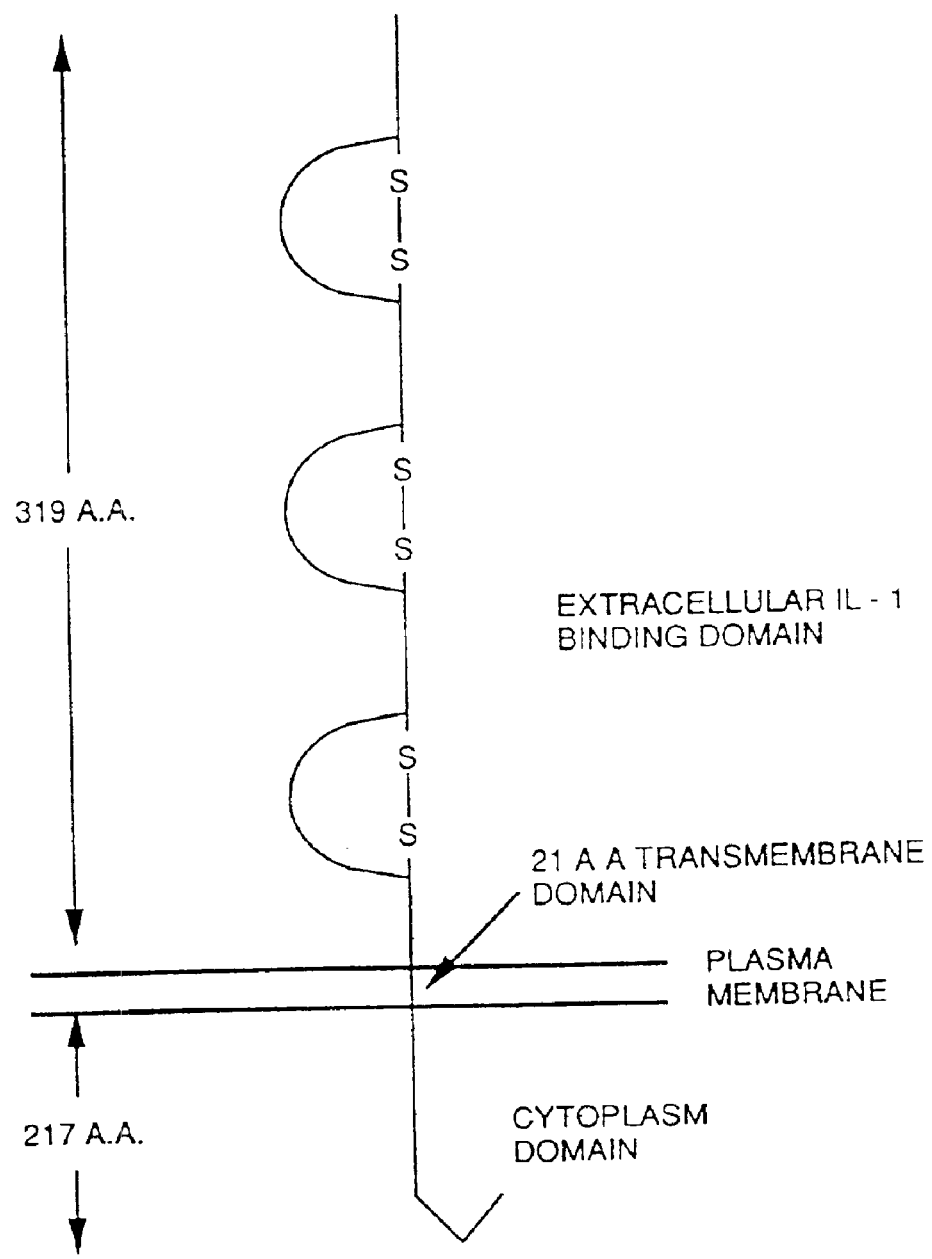
FIG. 7 shows the interleukin-1 binding domain amino acid arrangement.
Figure 8A:
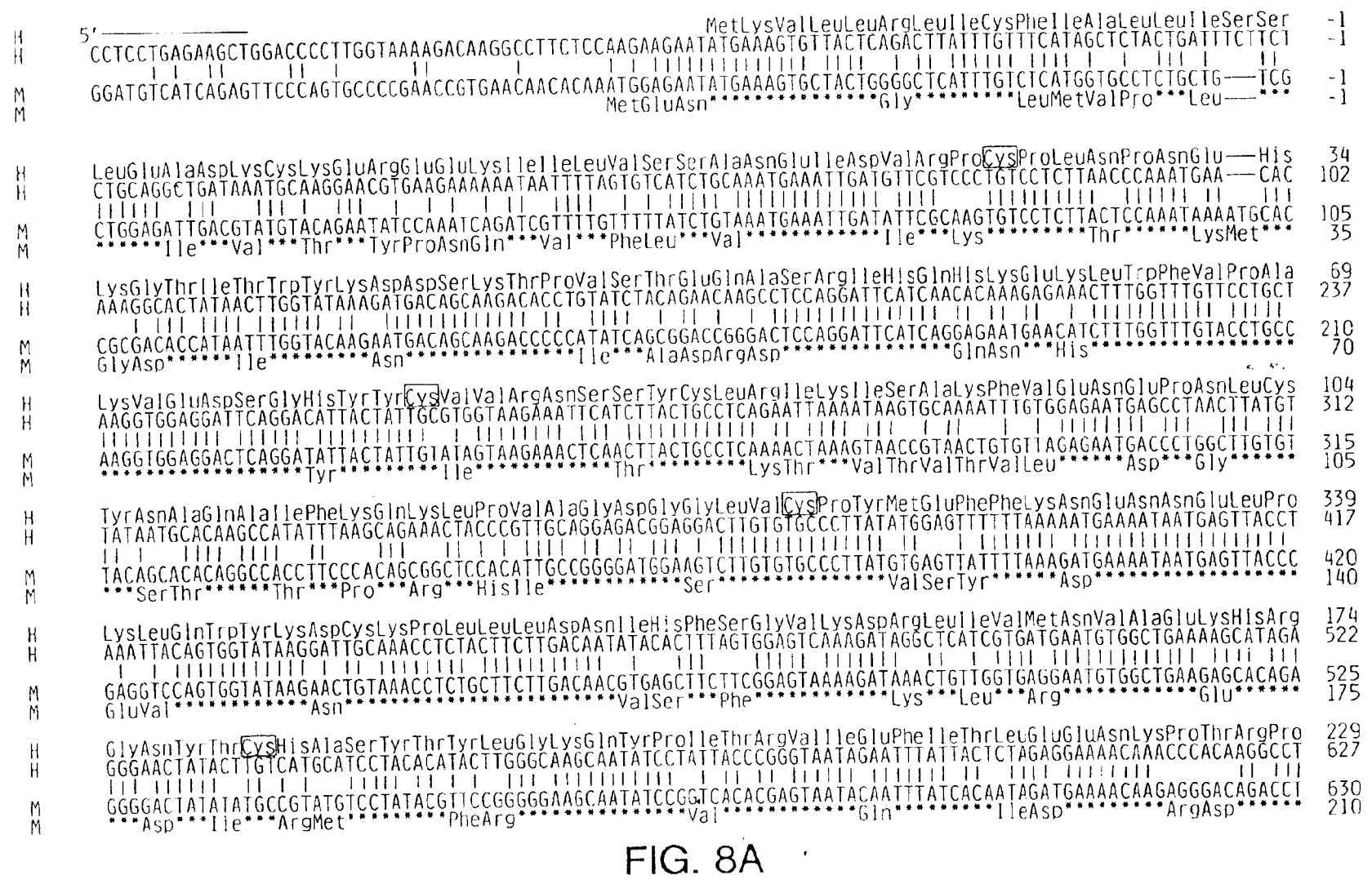
Figure 8B:
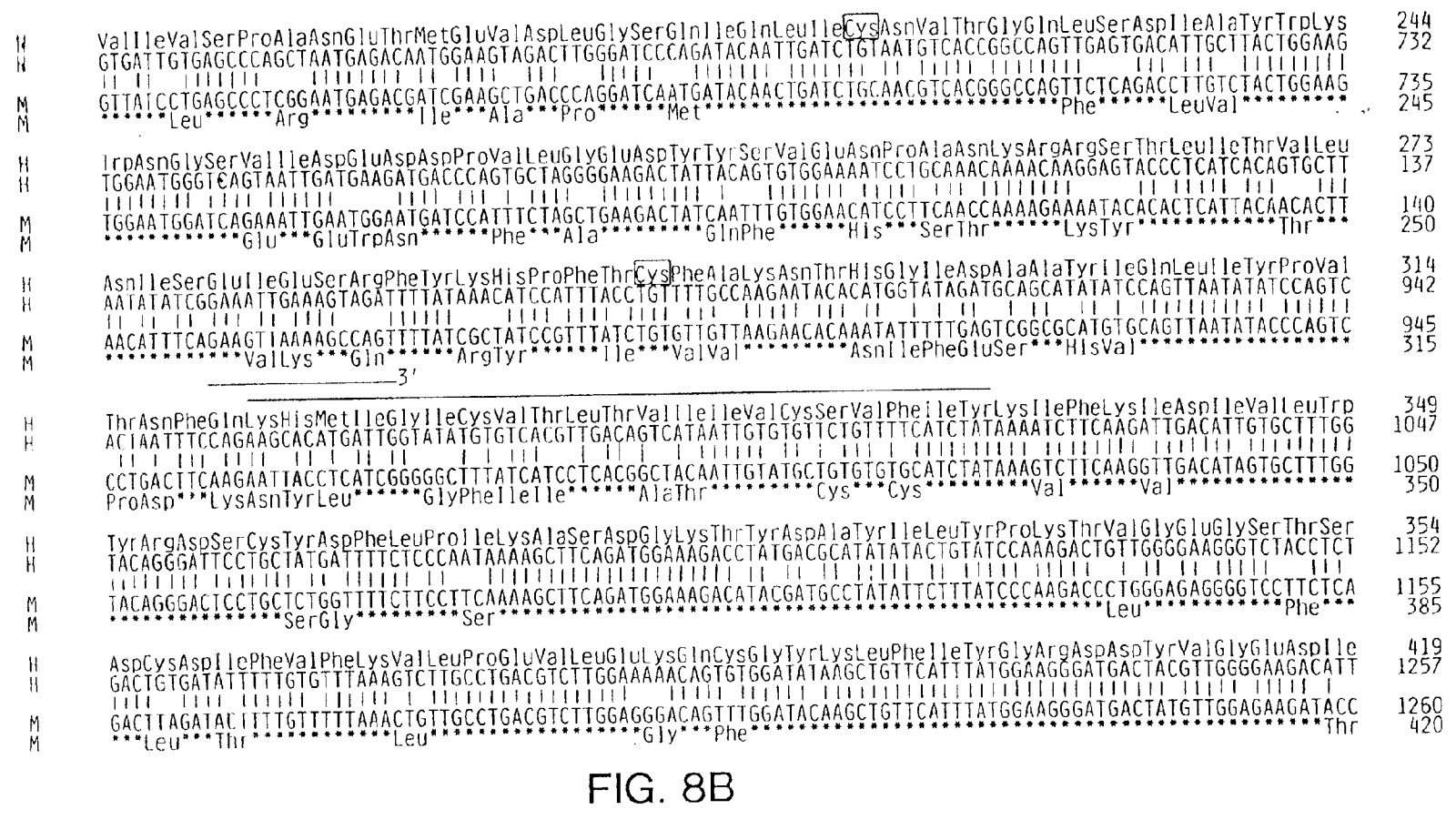
Figure 8C:
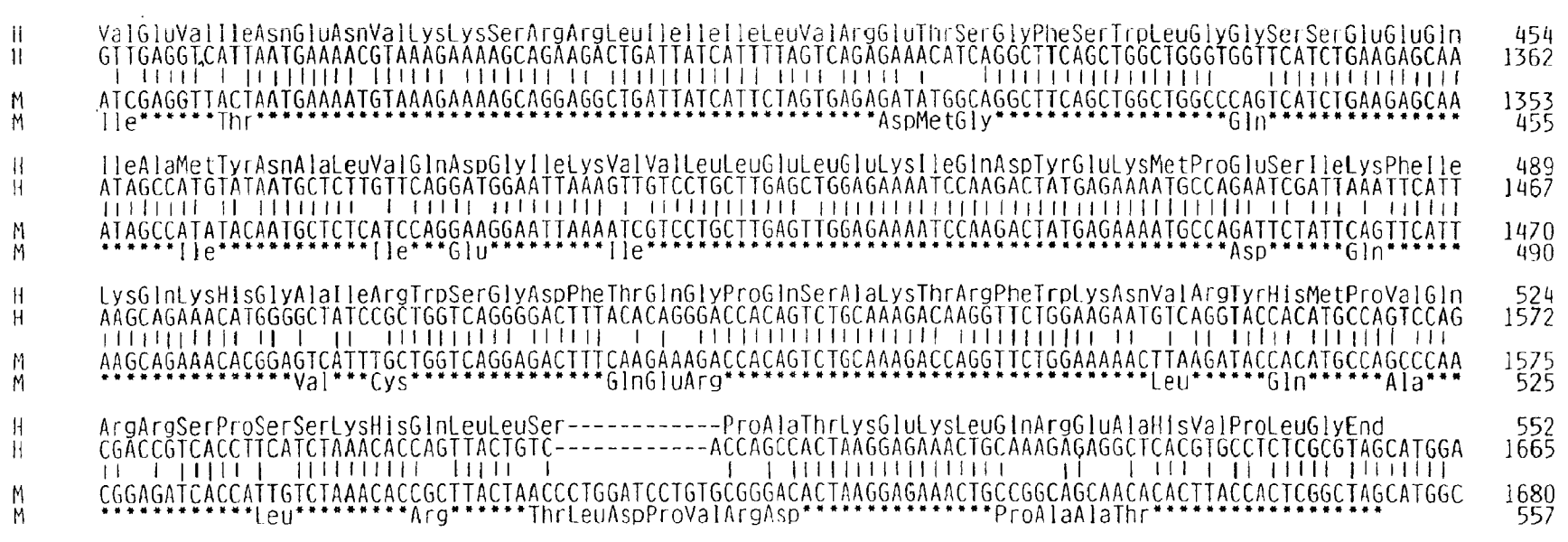
Figure 9:
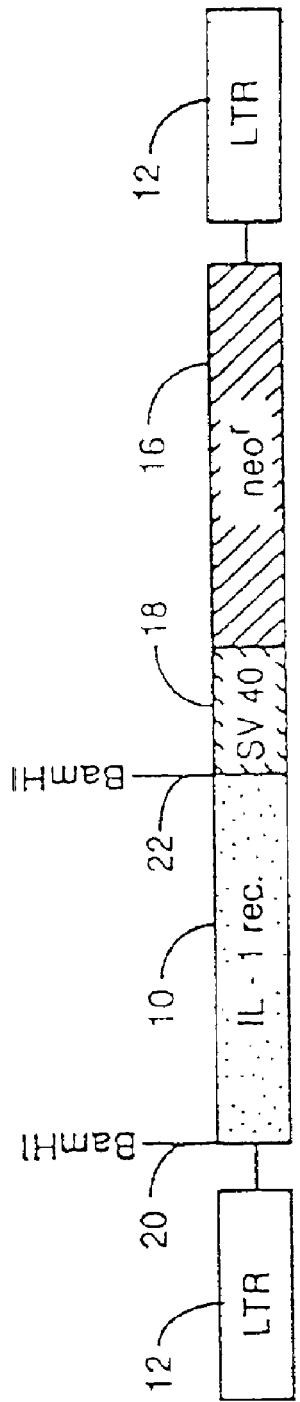
FIG. 9 shows gene encoding a soluble interleukin-1 receptor inserted into a retroviral vector.

Interleukin-1 exists as several species, such as unglycosylated polypeptide of 17,000 Daltons. Two species have previously been cloned, interleukin-1 alpha and interleukin-1 beta. The alpha form has a pI of approximately 5, and the beta form has a pI around 7. Despite the existence of these isoforms, interleukin-1 alpha and interleukin-1 beta have substantially identical biological properties and share common cell surface receptors. The type I interleukin-1 receptor is a 80 kDa (kilodalton) glycoprotein and contains an extracellular, interleukin-1 binding portion of 319 amino acids which are arranged in three immunoglobulin-like domains held together by disulfide bridges as shown in FIG. 7. A 21 amino acid trans-membrane domain joins the extracellular portion to the 217 amino acid cytoplasmic domain. FIGS. 8A–8C show the amino acid and nucleotide sequence of the human and mouse interleukin-1 receptors. In FIG. 8B, the 21 amino acid trans-membrane region of the interleukin-1 receptor is marked by the thicker solid line. In FIGS. 8A and 8B, the position of the 5' and 3' oligonucleotides for PCR are marked by thinner short lines, respectively. The lysine amino acid just 5' to the trans-membrane domain to be mutated to a stop codon is marked by a solid circle in FIG. 8B.

Synovium is by far the major, and perhaps the only, intraarticular source of interleukin-1 in the arthritic joint. Synovia recovered from arthritic joints secrete high levels of interleukin-1. Both the resident synoviocytes and infiltrating blood mononuclear cells within the synovial lining produce interleukin-1.

The present invention provides a method of using in vivo a gene coding for a truncated form of the interleukin-1 receptor which retains its ability to bind interleukin-1 with high affinity but which is released extracellularly and therefore inactive in signal transduction. The binding of this truncated and modified receptor to interleukin-1 inhibits the intraarticular activity of interleukin-1.

This method of using a gene encoding the extracellular interleukin-1 binding domain of an interleukin-1 receptor that is capable of binding to and neutralizing interleukin-1 includes employing a retroviral vector carrying a truncated interleukin-1 receptor gene which encodes a truncated and soluble active form of the receptor. The expression of the novel interleukin-1 receptor gene is controlled by regulatory sequences contained within the vector that are active in eukaryotic cells. This recombinant viral vector is transfected into cell lines stably expressing the viral proteins in trans required for production of infectious virus particles carrying the recombinant vector. These viral particles are used to deliver the recombinant interleukin-1 receptor to the recipient synovial cells by direct virus infection in vivo.

The soluble human interleukin-1 receptor to be inserted into the retroviral vector may be generated by a polymerase chain reaction (PCR). An oligonucleotide complementary to the 5' leader sequence of the human interleukin-1 receptor (GCGGATCCCCTCCTGAGAAGCT; SEQ ID NO: 5) and an oligonucleotide complementary to a region just upstream from the transmembrane domain of the interleukin-1 receptor (GCGGATCCCATGTGCTACTGG; SEQ ID NO: 6) are used as primers for PCR. The primer for the region of the interleukin-1 receptor adjacent to the trans-membrane domain contains a single base change so that the lys codon at amino acid 336 (AAG) is changed to a stop codon (TAG). By inserting a translation stop codon just upstream from the transmembrane domain, a truncated form of interleukin-1 receptor that is secreted by the cell is generated. A BamHI recognition sequence (GGATCC) is added to the 5' end of the PCR primers, and following amplification, the resulting interleukin-1 receptor fragment is cloned into a BamHI site. A cDNA library from human T-cells is used as a source for the interleukin-1 receptor cDNA. To amplify the appropriate region of the interleukin-1 receptor from the cDNA library, the complementary primers are added to the DNA and 50 cycles of annealing primer extension and denaturation are performed using a thermocycler and standard PCR reaction conditions well known by those persons skilled in the art. Following amplification of the interleukin-1 soluble receptor using the PCR process, the resulting fragment is digested with BamHI and inserted into the pLJ retroviral vector. The pLJ retroviral vector is available from A. J. Korman and R. C. Mulligan. See also *Proc. Nat'l. Acad. Sci.,* 84:2150–2154 (April 1987) co-authored by Alan J. Korman, J. Daniel Frantz, Jack L. Strominger and Richard C. Mulligan. Restriction analysis was performed to determine the correct orientation of the insert. It could also be cloned into MFG.

The retrovirus vector carrying the truncated interleukin-1 receptor is transferred into the CRIP (*Proc. Nat'l. Acad. Sci.* Vol. 85, pp. 6460–6464 (1988), O. Danos and R. C. Mulligan) packaging cell line using a standard $Ca_3(PO_4)_2$ transfection procedure and cells wherein the viral vector is stably integrated and is selected on the basis of resistance to the antibiotic G418. The viral vector containing the neomycin resistant (neo-r) gene is capable of imparting resistance of the cell line to G418. The CRIP cell line expresses the three viral proteins required for packaging the vector viral RNAs into infectious particles. Moreover, the viral particles produced by the CRIP cell line are able to efficiently infect a wide variety of mammalian cell types including human cells. All retroviral particles produced by this cell line are defective for replication but retain the ability to stably integrate into synovial cells thereby becoming an heritable trait of these cells. Virus stocks produced by this method are substantially free of contaminating helper-virus particles and are also non-pathogenic.

More specifically, the truncated interleukin-1 gene can be inserted into a retroviral vector under the regulation of a suitable eukaryotic promoter such as the retroviral promoter already contained within the gene transfer vector, such as for example, the pLJ vector shown in FIG. 9. FIG. 9 shows the structure of the pLJ interleukin receptor retroviral vector and partial restriction endonuclease map. Reference numeral 10 shows the interleukin-1 receptor inserted into a retroviral vector. Reference numeral 12 indicates long terminal repeats (LTR's) at each end of the structure of the pLJ interleukin receptor retroviral vector shown in FIG. 8. These LTR's regulate the viral transcription and expression of the interleukin-1 receptor. Bacterial gene encoding resistance to the antibiotic neomycin (neo-r) is shown at reference numeral 16. The Simian Virus 40 enhancer promoter (SV 40) is indicated at reference numeral 18, and regulates the expression of the neo-r gene. Reference numbers 20 and 22, respectively, show the sites wherein the resulting interleukin receptor fragment is cloned. It will be understood by those persons skilled in the art that other vectors containing different eukaryotic promoters may also be utilized to obtain a generally maximal level of interleukin-1 receptor expression. The vectors containing the truncated, and modified interleukin-1 receptor will be introduced into a retroviral packaging cell line (CRIP) by transfection and stable transformants isolated by selection for the expression of the neomycin resistance gene also carried by the pLJ vector. The CRIP cell line expresses all the proteins required for packaging of the exogenous retroviral RNA. Viral particles produced by the G418-selected CRIP cell lines will carry a recombinant retrovirus able to infect mammalian cells and stably express the interleukin-1 truncated receptor. The viral particles can be used to infect synovial cells directly in vivo by injecting the virus into the joint space or alternatively in vitro as part of ex vivo transplant methods.

Another embodiment of this invention provides a method for using the hereinbefore described viral particles to infect in culture synovial cells obtained from the lining of the joint of a mammalian host. The advantage of the infection of synovial cells in culture is that infected cells harboring the interleukin-1 receptor retroviral construct can be selected using G418 for expression of the neomycin resistance gene. The infected synovial cells expressing the interleukin-1 receptor can then be transplanted back into the joint by intra-articular injection. The transplanted cells will express high levels of soluble interleukin-1 receptor in the joint space thereby binding to and neutralizing substantially all isoforms of interleukin-1, including interleukin-1 alpha and interleukin-1 beta.

The method used for transplantation of the synovial cells within the joint is a routine and relatively minor procedure used in the treatment of chronic inflammatory joint disease. Although synovium can be recovered from the joint during open surgery, it is now common to perform synovectomies, especially of the knee, through the arthroscope. The arthroscope is a small, hollow rod inserted into the knee via a small puncture wound. In addition to permitting the intraarticular insertion of a fibre-option system, the arthroscope allows access to surgical instruments, such that synovial tissue can be removed arthroscopically. Such procedures can be carried out Linder "spinal" anesthetic and the patient allowed home the same day. In this manner sufficient synovium can be obtained from patients who will receive this gene therapy.

The synovial cells (synoviocytes) contained within the excised tissue may be aseptically recovered by enzymic digestion of the connective tissue matrix. Generally, the synovium is cut into pieces of approximately 1 millimeter diameter and digested sequentially with trypsin (0.2% w/v in Gey's Balanced Salt Solution) for 30 minutes at 37° Centigrade, and collagenase (0.2% w/v in Gey's Balanced Salt Solution) for 2 hours at 37° Centigrade. Cells recovered from this digestion are seeded into plastic culture dishes at a concentration of $10^4$–$10^5$ cells per square centimeter with Ham's $F_{12}$ medium supplemented with 10% fetal bovine serum and antibiotics. After 3–7 days, the culture medium is withdrawn. Non-adherent cells such as lymphocytes are removed by washing with Gey's Balanced Salt Solution and fresh medium added. The adherent cells can now be used as they are, allowed to grow to confluency or taken through one or more subcultures. Subcultivating expands the cell number and removes non-dividing cells such as macrophages.

Following genetic manipulation of the cells thus recovered, they can be removed from the culture dish by trypsinizing, scraping or other means, and made into a standard suspension. Gey's Balanced Salt Solution or other isotonic salt solutions of suitable composition, or saline solution are suitable carriers. A suspension of cells can then be injected into the recipient mammalian joint. Intra-articular injections of this type are routine and easily carried out in the doctor's office. No surgery is necessary. Very large numbers of cells can be introduced in this way and repeat injections carried out as needed.

Another embodiment of this invention is the gene produced by the hereinbefore described method of preparation. This gene carried by the retrovirus may be incorporated in a suitable pharmaceutical carrier, such as for example, buffered physiologic saline, for parenteral administration. This gene may be administered to a patient in a therapeutically effective dose. More specifically, this gene may be incorporated in a suitable pharmaceutical carrier at a therapeutically effective dose and administered by intra-articular injection. Therefore, the preferred mode regarding the ex vivo method of delivery is the removal of the patients connective tissue (e.g., synovia), in vitro culture of this connective tissue, transduction of the DNA sequence of interest, followed by the above-mentioned manipulation prior to delivery to the afflicted joint of the patient.

In another embodiment of this invention, this gene may be administered to patients as a prophylactic measure to prevent the development of arthritis in those patients determined to be highly susceptible of developing this disease. More specifically, this gene carried by the retrovirus may be incorporated in a suitable pharmaceutical carrier at a prophylactically effective dose and administered by parenteral injection, including intraarticular injection.

Example X

Fifty micrograms of a DNA plasmid vector molecule containing the interleukin-1 beta coding sequence ligated downstream of the CMV promoter was encapsulated within cationic liposomes, mixed with Gey's biological buffer and injected intraarticularly into the knee joints of a rabbit. Forty eight hours subsequent to injection one nanogram of interleukin-1 beta was recovered from the knee joint area. Therefore, injection of the DNA containing liposome solution within the region of the synovial tissue prompted fusion of the liposomes to the synovial cells, transfer of the DNA plasmid vector into synovial cells and subsequent expression of the IL-1 beta gene. Additionally, it is possible to inject non-encapsulated (i.e., naked) DNA into the joint area and monitor transfection of the DNA vector into the synovial cells as determined by subsequent expression of the IL-1 beta gene in synovial cells. Therefore; either method may be utilized as a plausible alternative to the in vitro manipulation of synovia also exemplified in the present invention.

Example XI

Figure 10:
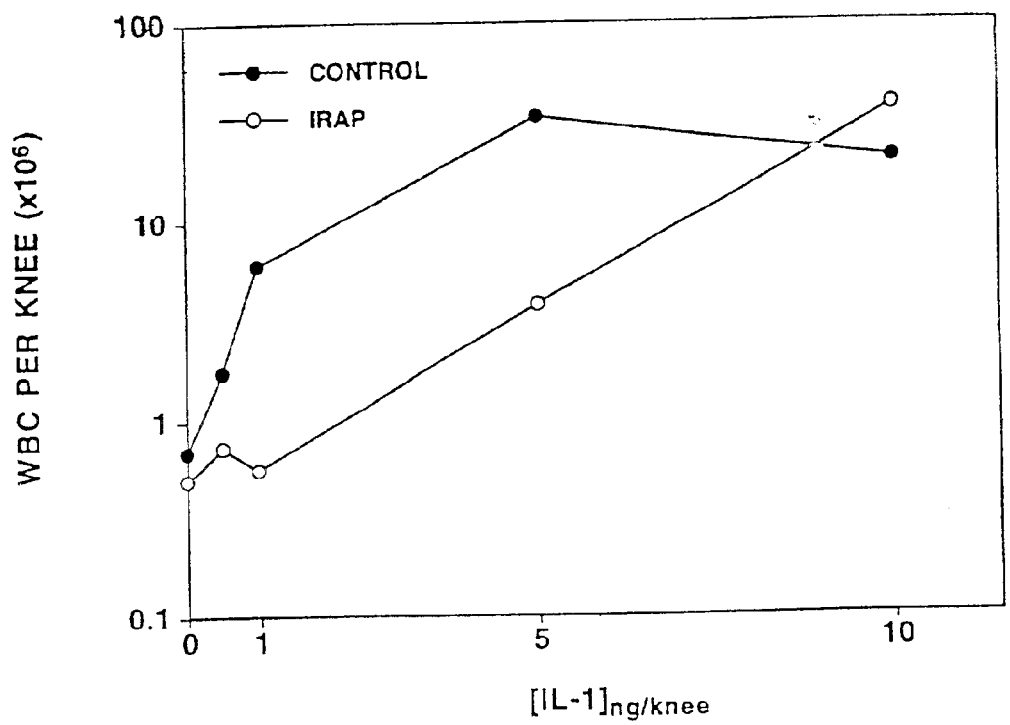
FIG. 10 shows anti-inflammatory properties of the MFG-IRAP transgene. MFG-IRAP/HIG-82 cells ($10^7$) or untransduced HIG-82 cells ($10^7$) were transplanted to the knee joints of rabbits 3 days before intraarticular challenge with the indicated amounts of recombinant human interleukin-1 beta (rhIL-1β). Lavage of joints occurred 18 hours later, after which infiltrating leukocytes were counted.

The in vivo biological activity of the MFG-IRAP construct was tested as the ability to suppress the effects of IL-1β. Rabbit knees were injected with recombinant human IL-1β, known to cause an increased concentration of leukocytes within the afflicted joint space. Introduction of MFG-IRAP/HIG-82 cells into rabbit knees strongly suppresses IL-1β production of leukocytes to the afflicted joint space. In contrast, control HIG-82 cells do not suppress the leukocyte infiltration to the joint space challenged with IL-1β (see FIG. 10). Inhibition is greatest at the lowest doses of human recombinant IL-1β (hrIL-1β), as expected by the competitive mechanism through which IRAP antagonizes IL-1. Therefore, this rabbit model confirms that in vivo, intra-articular expression of IRAP is biologically active and can protect the joint from inflammation provoked by IL-1.

Example XII

This example further evaluates ex vivo delivery into rabbit knee joints of the MFG-IRAP construct. As known, IRAP is an acidic glycoprotein of approximately 25 kDa that functions as a natural antagonist of the biological actions of interleukin-1 (IL-1) by binding to IL-1 receptors. Unlike IL-1 IRAP has no agonist activity, instead acting as a competitive inhibitor of the binding of IL-1.

This example shows that in Vivo expression of IRAP by genetically modified synovial cells inhibits IL-1β-induced leukocyte infiltration into the joint space, synovial thickening and hypercellularity, and loss of proteoglycans from articular cartilage.

As mentioned within this specification, the preferred lode of treating a patient through the ex vivo route will be by transplanting genetically modified autologous synovial cells by intra-articular injection. However, HIG-82 cells, easily maintained in culture, were used for these experiments to show that intra-articularly expressed IRAP is effective in inhibiting the physiological sequelae of intra-articularly injected IL-1.

MFG-IRAP/HIG-82 cells or control (uninfected HIG-82) cells, were transplanted into rabbit knees by intra-articular injection by the methods disclosed within this specification. Briefly, cultures of these cells were infected with MFG-IRAP. Media conditioned for 3 days by infected MFG-IRAP/HIG 82 cells were assayed for human IRAP by ELISA assay using a commercial kit (R&D Systems, Minneapolis, Minn., USA) and found to contain approximately 500 ng IRAP/$10^6$ cells. Western blotting confirmed the presence of human IRAP of size 22–25 kDa. HIG-IRAP cells were trypsinized, suspended in Gey's balanced salt solution and 1 ml of suspension, containing $10^7$ cells, was injected intra-articularly into the left knee joints of New Zealand White rabbits (2.5 kg). The contralateral control knees received a similar injection of untransducecd HIG-82 cells.

Three days following transplantation of the cells, knee joints were challenged by various doses of a single intra-articular injection of human recombinant IL-1β dissolved in 0.5 ml Gey's solution. Control knees were injected with 0.5 ml of Gey's solution.

Eighteen hours after injection of hrIL-1β, rabbits were killed and the knee joints evaluated histopathologically and for expression of IRAP. Each joint was first lavaged with 1 ml Gey's solution containing 10 mM EDTA. Cal counts in these washings were performed with a hemocytometer. An aliquot was removed for cytospinning and staining with 'DiffQuick' (Baxter Scientific Products) before examination under light microscopy. Washings were then centrifuged. Supernatants were removed for IRAP ELISA and for the determination of glycosaminoglycan (GAG) concentrations as an index of cartilage breakdown. GAG determinations were carried out with the dimethylmethylene blue assay (Farndale, et al., *Biochim. Biophys. Acta.* 883: 173–177 (1986)).

Synovia were dissected from the knee joints, fixed in 70% ethanol, dehydrated, embedded in paraffin, sectioned at 5 μm and stained with hematoxylin and eosin.

Figure 11:
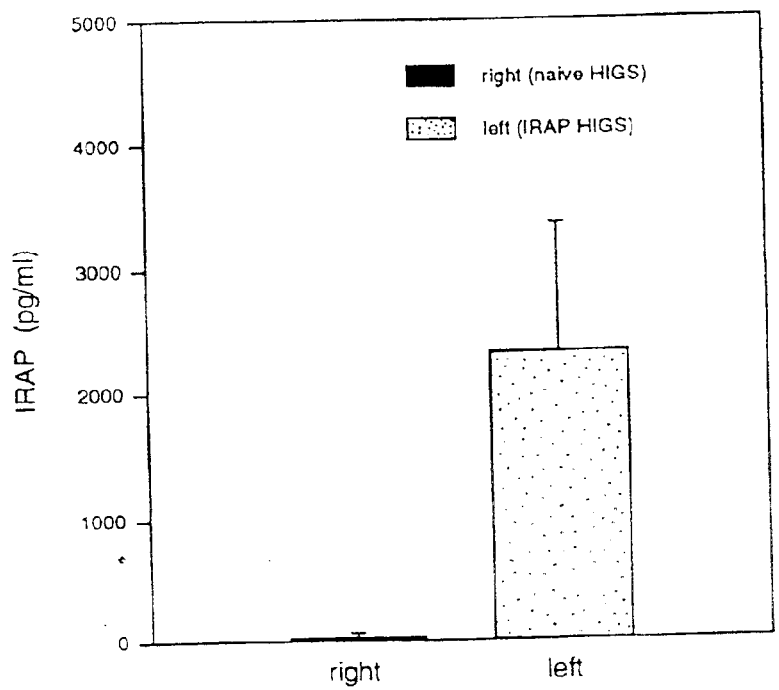
FIG. 11 shows levels of human IRAP in rabbit knees four days following transplant of synoviocytes. Either untransduced (naive) HIG-82 cells or cells carrying a human IRAP gene (MGF-IRAP/HIG-82) were injected intraarticularly in the knee joints or rabbits ($10^7$ cells/knee). Four days later, knees were lavaged and the concentration of human IRAP determined by ELISA. Values given are means±S.D. (n=15).
Figure 12A:
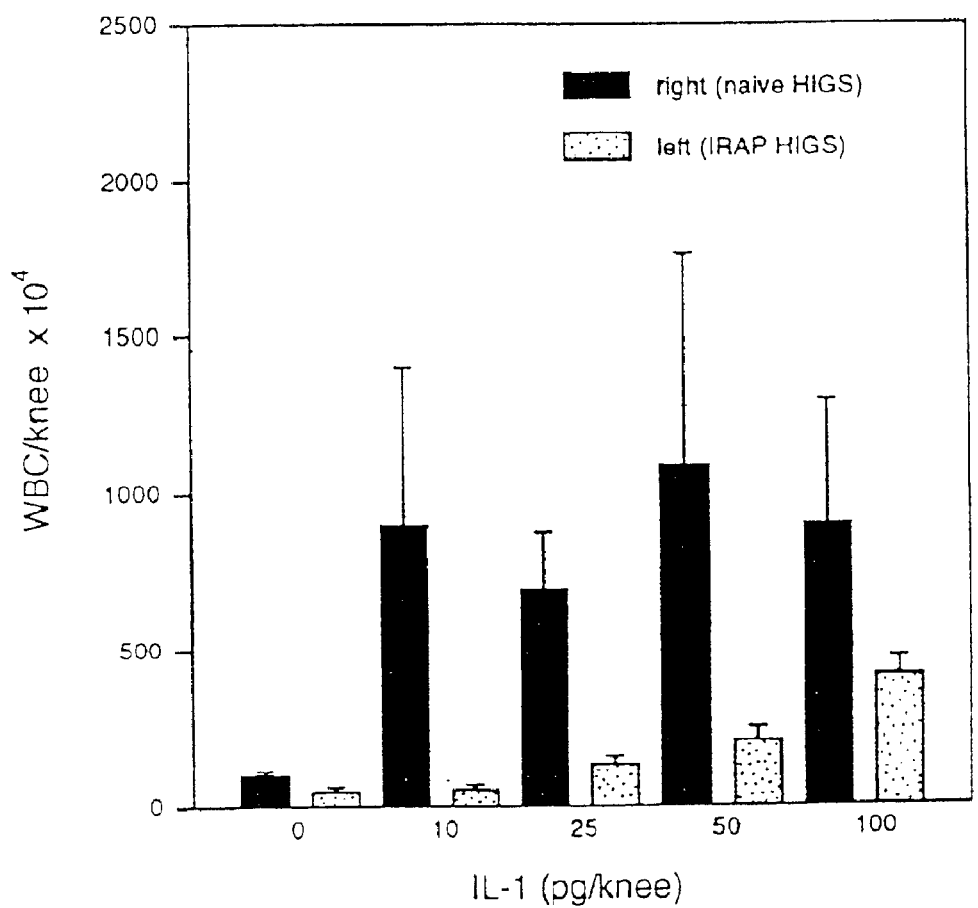
FIGS. 12 A–C shows inhibition of IL-1 induced leukocyte infiltration in knees expressing IRAP gene. Either naive or IRAP-transduced HIG-82 cells were transplanted into rabbit knee joints, as indicated Three days later 0–100 pg/knee hIL-1β was intraarticularly injected at the indicated doses. The following day, knee joints were lavaged and the leukocytic infiltrate analyzed by counting with a hemocytometer and by cytospinning. Means±S.E. (n=3). (A) White blood cells (WBC) per knee. (B) Stained cytospin preparation of lavages from control knee injected with IL-1. Preparation was diluted 1:10 prior to cytospinning. (C) Stained cytospin preparation of lavages from IRAP-secreting knee injected with IL-1. The preparation was not diluted.

An average of 2.5 ng human IRAP per knee was measured in joint lavages 4 days following transplant of MFG-IRAP/HIG 82 cells. Contralateral, control knees receiving naive HIG-82 cells had no detectable human IRAP (FIG. 11). To determine whether the observed level of IRAP expression was sufficient to inhibit the effects of IL-1 in vivo, increasing concentrations of IL-1β (0–100 pg) were injected into both the control and IRAP knees. As is shown in FIG. 12a, injection of hrIL-1β into control knees provoked a marked leukocytosis which was strongly suppressed in the genetically modified knees. There was also a statistically significant reduction in the white blood cell count in knees containing MFG-IRAP/HIG 82 cells which had not been injected with IL-1. This may reflect the influence of IRAP upon the slight inflammatory effect of injecting cells into joints. The degree of suppression by IRAP decreased as the amount of injected hrIL-1β increased, in keeping with the competitive mode of inhibition existing between IRAP and IL-1. No dose-response for hrIL-1β alone is evident in these particular experiments because this specific batch of IL-1 was especially effective in eliciting maximal response even at the lowest dose used.

Figure 12B:
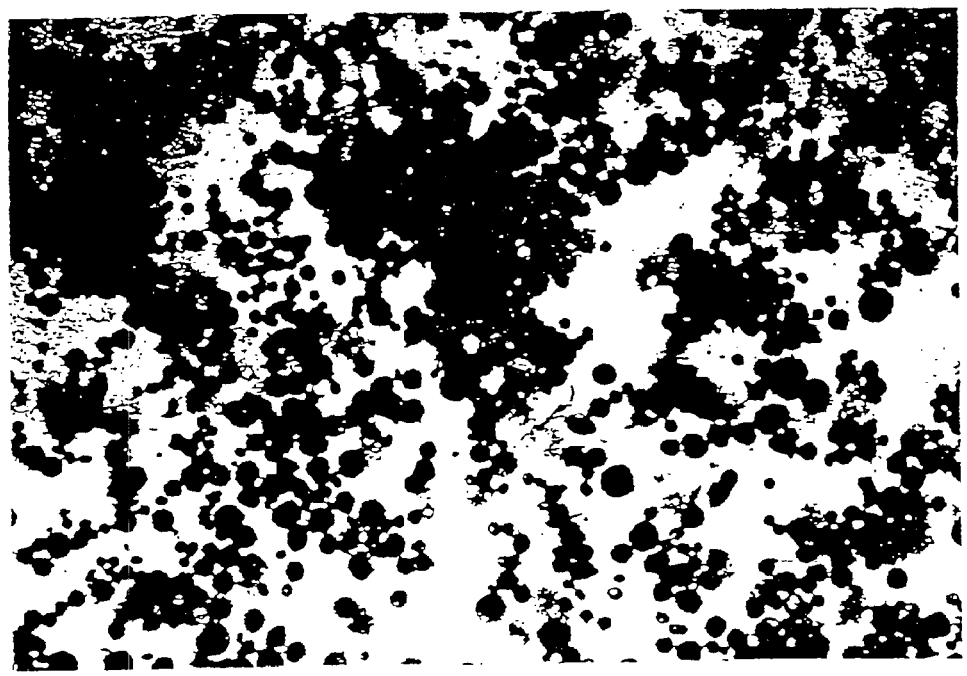
Figure 12C:
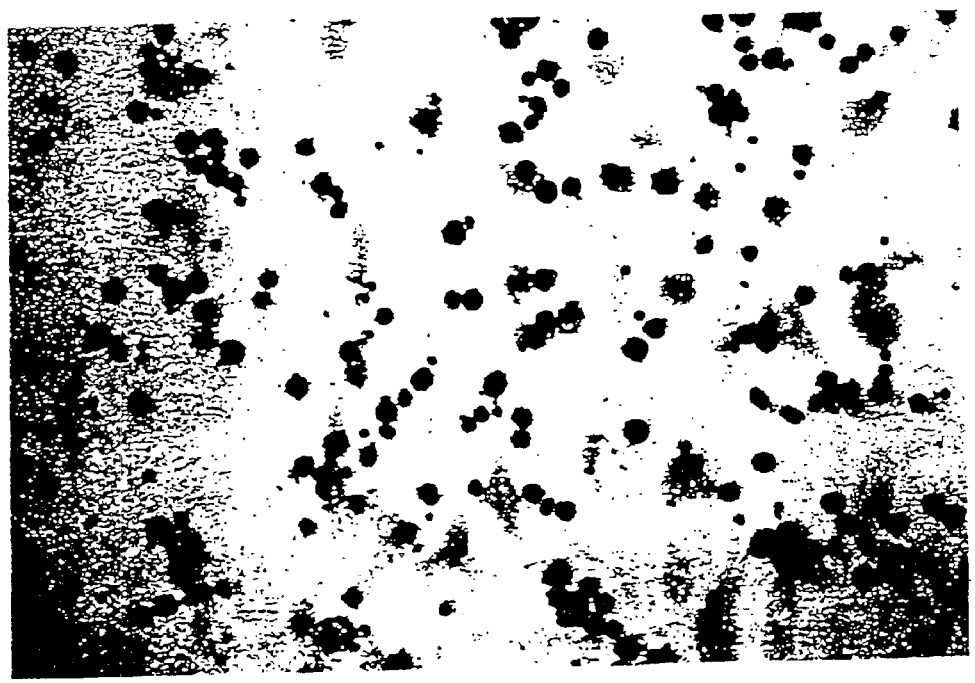

Examination of cytospins (FIGS. 12b, 12c) revealed that most of the infiltrating leukocytes were neutrophils and monocytes. These preparations also serve to illustrate the efficiency with which leukocytosis was suppressed by the IRAP gene. Ten times the volume of lavage fluid is represented on the cytospin obtained from the IRAP-producing knees (FIG. 12c) compared to the non-IRAP knee (FIG. 12b).

Figure 13:
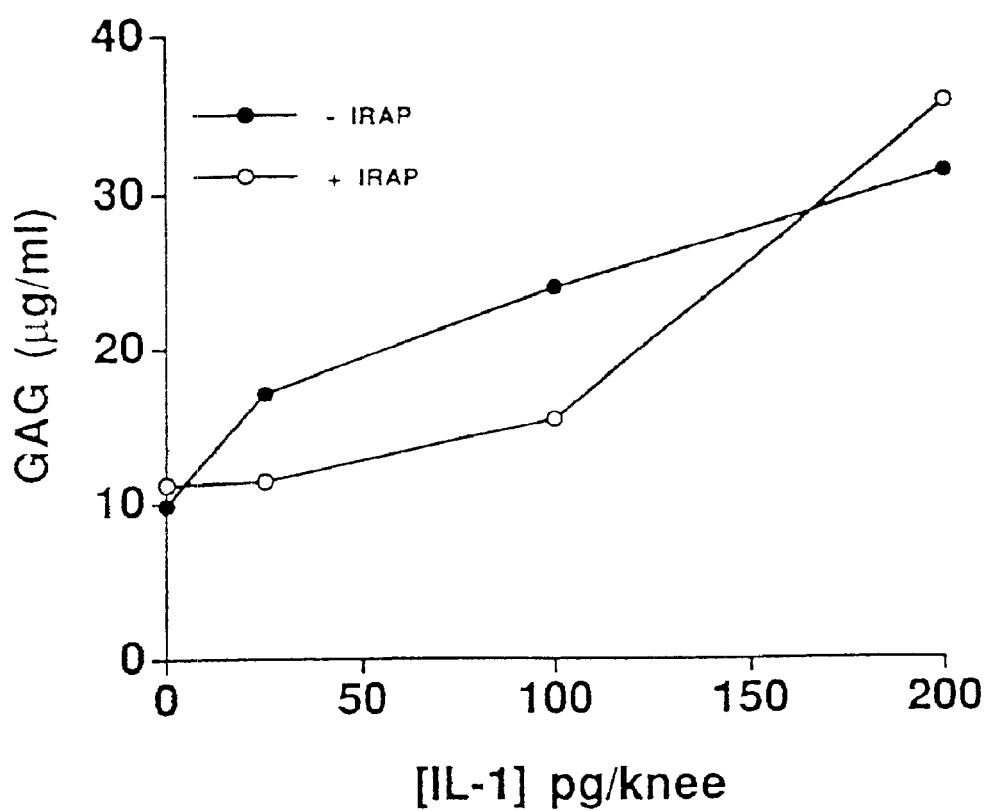
FIG. 13 shows suppression of IL-1 induced loss of proteoglycans from articular cartilage. Either naive or IRAP-transduced HIG-82 cells were transplanted into rabbits knee joints. Three days later, 0–200 pg/knee hrIL-1 was intraarticularly injected at the indicated doses. The following day, knee joints were lavaged and the level of glycosaminoglycans (GAG) as an index of cartilage breakdown was determined.

To determine if intra-articularly expressed IRAP was able to block cartilage breakdown, the concentration of glycosaminoglycans (GAG) in joint lavages was determined. GAG analyses of the washings from the control and IRAP expressing knees (FIG. 13) confirmed that transfer of the IRAP gene partially inhibited breakdown of the cartilaginous matrix in response to IL-1. Again, inhibition was strongest at the lowest concentrations of IL-1 and was abolished at the highest dose of IL-1 (FIG. 13).

Figure 14A:
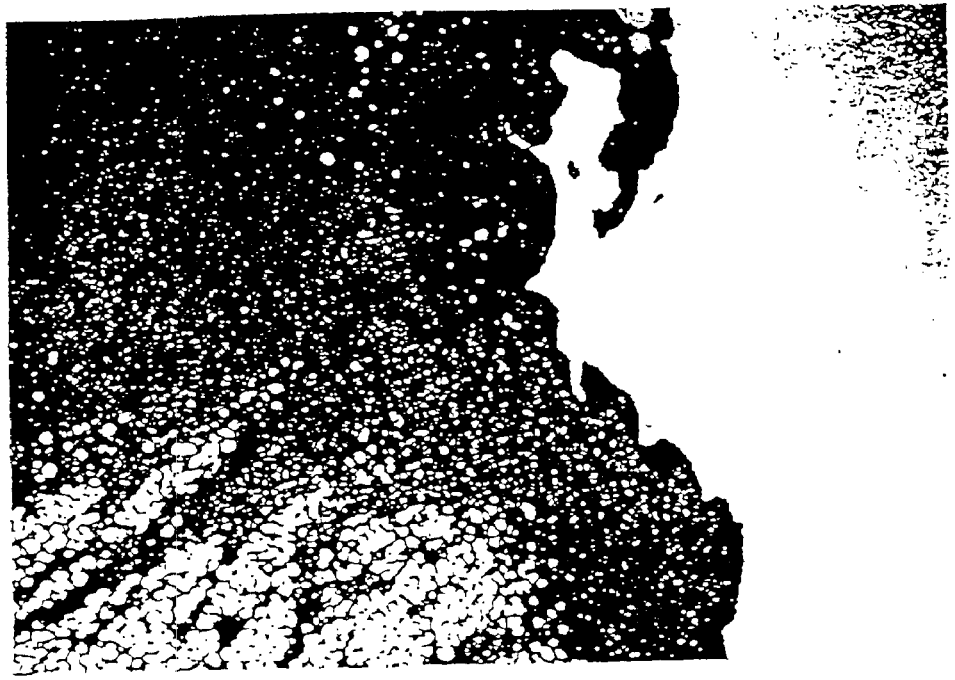
FIGS. 14A–D shows suppression of IL-1 mediated synovial changes in knees expressing IRAP. Ten pg hrIL-1B was injected intraarticularly in each case. Synovia were harvested 18 hours after injection of IL-1β, i.e. 4 days after transplantation of naive or IRAP-secreting HIG-82 cells. (A) Control synovium following injection of IL-1, magnification×10. (B) IRAP-secreting synovium following injection of IL-1, magnification×10. (C) Control synovium following injection of IL-1, magnification×160. (D) IRAP-secreting synovium magnification×160.
Figure 14B:
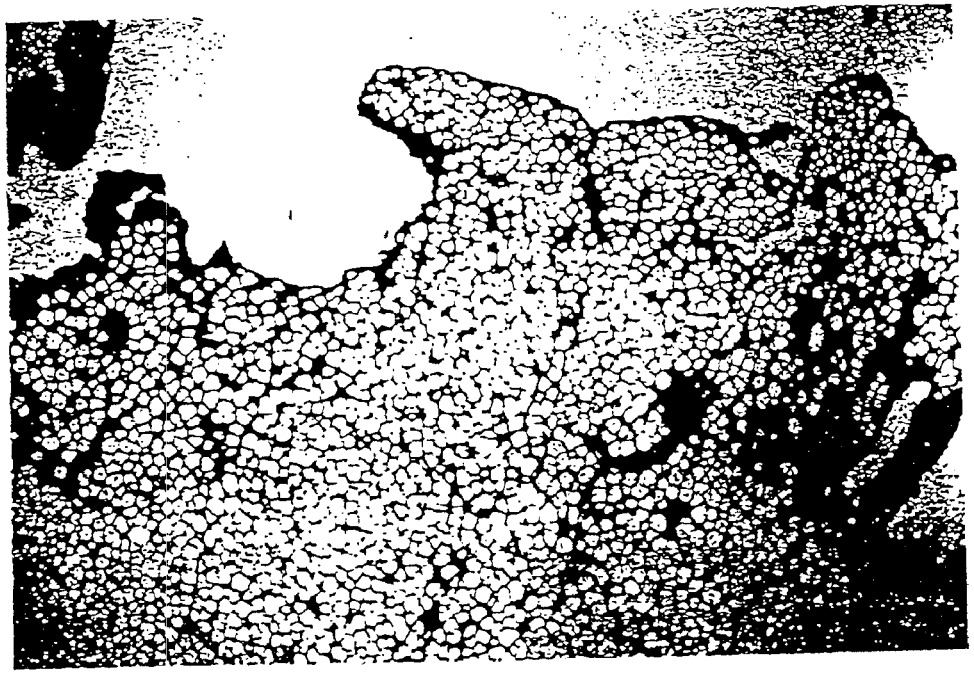
Figure 14C:
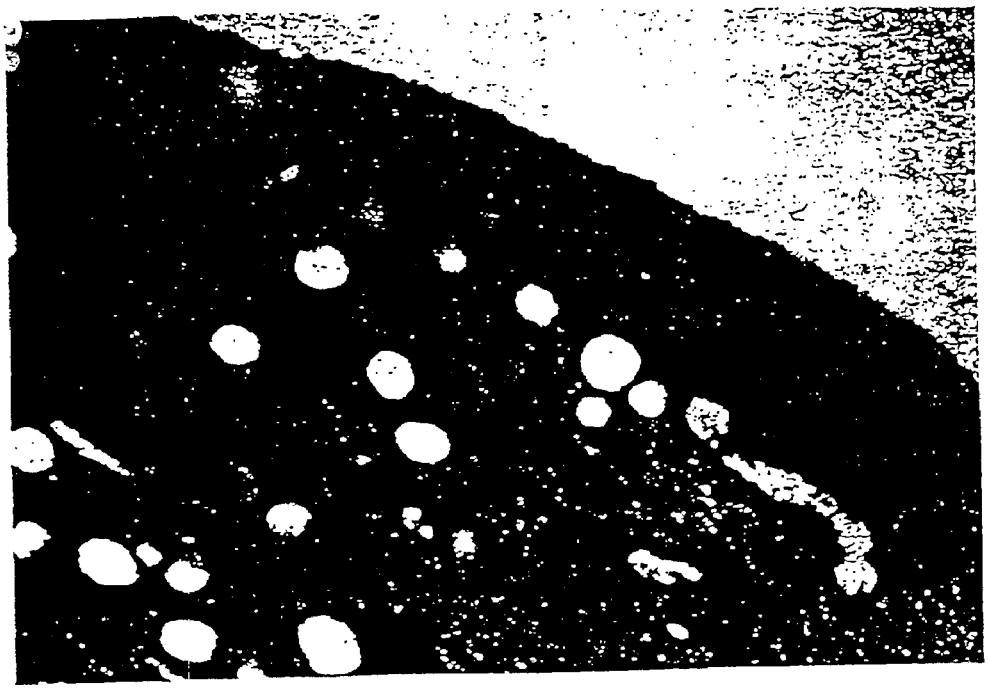
Figure 14D:
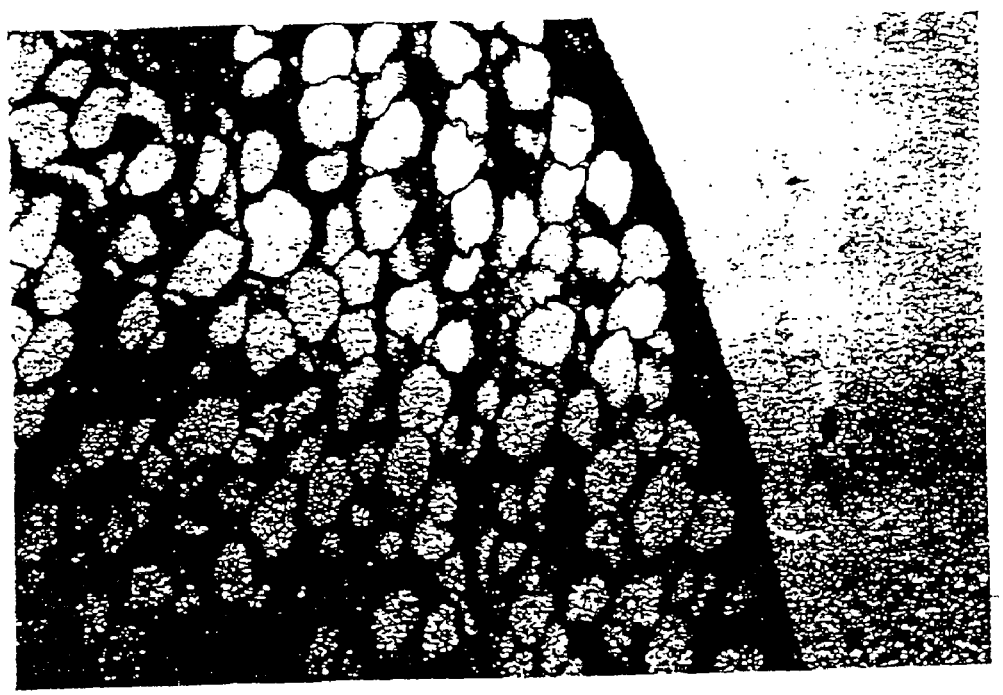

In response to 10 pg of injected hrIL-1β, control synovia became hypertrophic (FIG. 14a) and hypercellular (FIG. 14c). The increased cellularity of the synovia appeared to involve both increased numbers of synoviocytes and infiltration by leukocytes. In knees where MFG-IRAP/HIG 82 cells were present, these changes were completely suppressed and the synovia were nearly indistinguishable from control synovia (FIGS. 14b, 14d).

The ex vivo transfer of the human IRAP gene to the synovial lining of rabbit knees clearly protects these joints from the pathophysiological sequelae of subsequent intra-articular challenge by hrIL-1β.

Measurements of the amounts of IL-1 present in human, recombinant synovial fluids provide values in the range of 0–500 pg/ml (Westacott, et al., 1990, Ann Rheum Dis. 49: 676–681; Malvak, et al., 1993, Arthritis Rheum 36: 781–789). Thus the amounts of IRAP expressed intra-articularly during the present, short-term experiments should be sufficient to block the biological activities of IL-1 at the concentrations present in human arthritic joints.

Example XIII

This example shows that the level of intraarticular IRAP expressed subsequent to ex vivo transplantation of synoviocytes transduced with MFG-IRAP is sufficient to inhibit several pathophysiological changes associated with antigen-induced arthritis of the rabbit knee. Intraarticularly expressed IRAP has both a chondroprotective and anti-inflammatory effect during the acute phase of this disease. Data disclosed in Example XII support the contention that the invention as disclosed and claimed is a marked improvement for treating connective tissue disorders such as arthritis in comparison to delivery of proteins to the afflicted joint. Example XII shows that ex vivo transfer of MFG-IRAP to the rabbit knee as disclosed throughout this specification results in the intraarticular accumulation of nanogram quantities of glycosylated, biologically active IRAP. This present example shows that this same gene therapy based product inhibits joint pathologies in a rabbit model of human rheumatoid arthritis.

Young adult rabbits were subjected to a surgical, partial synovectomy of the left knee joint to provide autologous cells. These autologous cells were used to produce cultures of rabbit synovial fibroblasts (type B synoviocytes) from these biopsies as described in Example V and Example IX. Subconfluent cultures were then transduced by infection with MFG-IRAP. Expression of the transene was confirmed by measuring the concentrations of human IRAP in the conditioned media; values typically range from 100–500 ng IRAP/$10^6$ cells/3 days. Sister cultures of synoviocytes from the same animal were infected with a BAG virus encoding the lac Z and $neo^r$ marker genes, and then selected for growth in the presence of G418 (1 mg/ml) to serve as controls. Untransduced synoviocytes were also used as additional controls.

During the period that the cells were being grown and transduced, the donor rabbits were sensitized to ovalbumin by a series of two intradermal injections of 5 mg ovalbumin emulsified in adjuvant, given two weeks apart. Two weeks after the second injection, an acute monarticular arthritis was initiated by the injection of 5 mg ovalbumin dissolved in 1 ml saline into the right knee joints. By this time the left, donor knees had regenerated their synovia, and were each injected with 1 ml saline as controls.

One day after the onset of arthritis, $10^7$ autologous cells, transduced with either the IRAP gene, or lac Z and neo genes, were injected into each arthritic knee, and each contralateral, non-arthritic knee. In other control experiments, knees were injected with untransduced, autologous cells. Groups of rabbits were killed 3 and 7 days later, corresponding to the middle and end of the acute phase of this arthropathy. Knees were lavaged with 1 ml of saline, prior to the removal of synovial tissue and articular cartilage for analysis.

Intraarticular expression of the MFG-IRAP transgene was evaluated by ELISA measurements of human IRAP in the lavage fluids. IRAP concentrations in the control, non-arthritic knees is shown in FIG. 15. IRAP concentrations in the arthritic knees were always several-fold higher than in normal knees at both time points (FIG. 15). In both non-arthritic and arthritic knees transduced with MFG-IRAP, there was a slight decrease in IRAP expression with time. No human IRAP could be detected in sera obtained from normal or arthritic rabbits.

During the course of these experiments, the intraarticular concentration of rabbit IL-1 in arthritic knees was in the range of 100–200 pg/knee (FIG. 16). No IL-1α could be detected by RIA of the lavage fluids. Thus the concentration of IRAP within these knees exceeded the concentration of IL-1 by factors of approximately 10–50. Concentrations of IL-1 were lower in day 7 arthritic knees receiving the IRAP gene (FIG. 16), suggesting that IRAP had inhibited an autocrine amplification loop.

Two major pathologies predominate in the rheumatoid joint: loss of articular cartilage and inflammation. The former occurs through a combination of reduced synthesis and synergistic degradation of the cartilaginous matrix. Whereas inflammation is manifest as a synovitis accompanied by influx of leukocytes into the joint space.

The onset of antigen-induced arthritis in this Example was accompanied by cartilage destruction, as reflected in the increased glycosaminoglycan (GAG) content of the lavage fluids (FIG. 17*a*), and reduced synthesis of cartilage proteoglycans, as reflected by lower uptake of $^{35}SO_4^{2-}$ (FIG. 17*b*). Knees expressing the MFG-IRAP transgene, but not control knees, were substantially protected from these changes. GAG release (FIG. 17*a*) was inhibited 55% on day 4 and 32% on day 7. Suppression of GAG synthesis (FIG. 17*b*) was inhibited by 68% on day 4 and 100% on day 7. The MFG-IRAP transgene also strongly reduced the influx of leukocytes into the joint space (FIG. 18), an effect that was stronger at day 4 (65% inhibition) than at day 7 (38% inhibition); indeed, the difference at day 7 failed to reach statistical significance.

The MFG-IRAP construct is utilized to exemplify the presently claimed invention. In addition to this construct, the ex vivo based teachings of this specification have been utilized to transfer to synovial cells and express in vivo DNA sequences encoding human IL-1α, human TNF-α soluble receptor Types I and II, vIL-10, growth hormone, IL-6, Lac Z and $neo^r$.

Example XIV

The methods disclosed throughout this specification were utilized to express MFG-human IL-1 soluble receptor type I and type II constructs (with $neo^r$) within in vitro cultured synoviocytes. These transfected synoviocytes produce 1–2 ng/$10^6$ cells of IL-1 soluble receptor types I and II, following neo-selection. The additional methods disclosed throughout this specification may be utilized to procure in vivo expression data regarding these MFG-human IL-1 soluble receptor type I and type II constructs.

Example XV

Rabbits were injected intraarticularly in one knee joint with a specific viral or non-viral vector disclosed in Table 2. Contralateral knees were injected with a control, usually with the identical viral or non-viral vector with a different passenger gene. At intervals from 2 days to 2 weeks following intraarticular injection, rabbits were sacrificed and the knee joints harvested and stained with X-Gal to assay for LacZ expression. The results are depicted in Table 2. The recombinant adenovirus vector comprising a CMV-LacZ fusion and the recombinant HSV vector comprising a CMV-LacZ fusion generated the highest expression level subsequent to intraarticular injection. The recombinant retroviral vector, MFG-LacZ, was not expressed in vivo, lending credence to the concept that retroviral vectors require actively dividing cells during the infection process and the concomitant low mitotic activity of synoviocytes in the joint lining.

However, an intra-articular injection of MFG-IRAP to synovial cells of an inflamed joint space supported retroviral transduction. Injection of MFG-IRAP into an inflamed rabbit knee lead to the intraarticular accumulation of about 0.5 ng/knee at 7 days post injection. The contralateral knee did not express human IRAP. The example shows a MoMLV based retrovirus can be used for in vivo gene delivery to inflamed joints.

TABLE 2

| | | EXPRESSION | | |
|---|---|---|---|---|
| VECTOR | PROMOTER | In Vitro LAC Z cells (%) | In Vivo LEVEL | In Vivo DURATION (Days) |
| Retrovirus (MFG) | LTR | 20–30 | 0 | 0 |
| HSV | CMV | 1 (toxic) | +++ | 5–7 |
| Adenovirus | CMV | 100 | +++ | ≧14 |
| Liposome (DC-chol) | CMV | 20–30 | + | 1–2 |
| None (naked DNA) | CMV | 0 | ± | 1–2 |

Level of in vivo expression was evaluated subjectively on a scale of 0–+++, based upon the degree of staining with X-Gal.
LTR = viral long terminal repeat
CMV = cytomegalovirus Example XVI Vector Construction and Virus Production To facilitate efficient secretion of human interleukin-1β (hIL-1β), a DNA fragment encoding mature hIL-Lβ, amino acids 117–269 of the unprocessed protein was linked to sequences encoding the prepro leader peptide (amino acids 1–31) of human parathyroid hormone (hPTH). To remove the potential for N-linked glycosylation, amino acids 7 through 9 of mature hIL-1β were changed from the glycosylation consensus sequence, Asn-Cys-Ser, to Gln-Ala-Ser. The preproIL-1β coding region was PCR amplified and inserted into the Nco I and BamH I restriction sites of the MEG retroviral vector according to the methods of Dranoff, *Proc. Nat. Acad. Sci. U.S.A.* 90: 3539–3543 (1993) and Robbins et al., *Annals of the New York Academy of Sciences* 716: 72–89 (1993). The upstream primer (gcca ccATGgTACCTGCA; SEQ ID NO:7) contained nucleotides 1–12 of the 5' end of the hPTH leader sequence (shown in caps.), with the fourth residue changed from an A to a G and an additional 6 nucleotides to accommodate the recognition sequence for Neo I (underlined). The downstream primer (AGCACAGGATCCTCTGGGTAC; SEQ ID NO:8) corresponded to sequences in the pCDNAI vector adjacent to the 3' end of the hIL-1β coding region which were modified to contain a BamH I recognition sequence (underlined). To allow positive selection of retrovirally transduced cells, a DNA fragment containing an internal ribosome entry site, as described by Ghattas et al., *Mol Cell. Biol.* 11: 5848–5849 (1991). (IRES) 5' to the cDNA encoding neomycin phosphotransferase (neo) was inserted into the BamH I site of the MFG-hIL-1β plasmid, immediately downstream of the hIL-1β coding region. The resulting plasmid construct (pDFG-hIL-1β-neo) allows for expression of both the hIL-1β and neo$^r$ gene products from a single polycistronic transcript initiated from the upstream retroviral long terminal repeat as shown by Robbins et al., 715: 72–89 (1993), Tahara et al., *J. Immunol.* 154: 6466–6477 (1994) and Zitvogel et al., *Hum Gene Ther.* 5:1493–1506 (1994).

A 293-based retroviral packaging cell line, BING, was utilized for production of recombinant amphotropic retrovirus, as described by Pear et al., *Proc. Natl. Acad. Sci. U.S.A.* 90: 8392–8396 (1993).

Transduction of Synoviocytes

Synovial cells were grown to ~75% confluence in a 25 cm$^2$ flask containing 4 ml of Ham's F12 medium with 10% FCS and 1% P/S. The cells were retrovirally infected as previously described by Bandara et al., *Proc. Natl. Acad. Sci. U.S.A.* 90: 10764–10768 (1993). Infected cells were then selected in medium containing G418 at 0.5 mg/ml.

Synovial Cell Harvest and Transplantation

Partial surgical synovectomies were performed on anesthetized rabbits by sharp dissection via the medial parapatellar approach described by Kang et al., *Methods in Molecular Biology: Gene Therapy Protocols*, Totowa, N.J., Paul Robbins editor, pp. 357–368 (1996). The harvested tissue was digested in 0.2% clostridial collagenase for 2 hrs at 37° C., and the synoviocytes pelleted by centrifugation. The recovered cells were resuspended and cultured in Ham's F12 medium with 10% FCS and 1% P/S. In other experiments, an established line of rabbit synovial fibroblasts, HIG-82, was used. HIG-82 is described in Georgescu et al., In vitro 24: 1015–1022 (1988).

For intraarticular transplantation, cells were treated with trypsin, washed, and resuspended in Gey's balanced salt solution (GBSS) to a final concentration of between 10$^6$ to 10$^7$ cells per ml. A 1 ml sample of cell suspension was injected through the patellar tendon into the knee joints of recipient rabbits.

Biological Analyses

To lavage rabbit knee joints, 1 ml of GBSS plus 10 mM EDTA was injected into the joint space through the patellar tendon. After manipulation of the joint, the needle was reinserted and the fluid aspirated. Leukocytes in recovered lavage fluids were counted using a hemocytometer. The white blood cell types were analyzed by light microscopy of Diff-Quick-stained (Baxter Scientific Products) cytospins. Human IL-1β concentrations in conditioned media, lavage fluids and blood sera were measured as directed using ELISA kits from R & D Systems. Rabbit IL-1β levels were determined using an RIA kit (Cytokine Sciences Inc.).

To measure rabbit TNFα, 96-well plates were coated overnight at 4° C. with goat anti-rabbit TNFα polyclonal antibody (Pharmingen) at a concentration of 8 ug/ml in 0.1 M NaHCO$_3$, pH 8.2. The plates were then washed twice with PBS containing 0.05% Tween® 20, and then blocked by incubating overnight at 4° C. with PBS plus 10% FCS. After washing twice with PBS/Tween® 20 solution, standards and samples were added and incubated overnight at 4° C. The plates were then washed four times with PBS/Tween® 20. Detection of the captured antigen was facilitated by the addition of biotinylated goat anti-rabbit TNFα polyclonal antibody (Pharmingen) at 4 ug/mi in PBS with 10% FCS and incubation 45 min at room temperature. Plates were then washed six times followed by the addition of 100 µl/well of avidin-peroxidase (Intergen) diluted 1:400 in PBS/Tween® 20, for 30 min at room temperature. After washing 8 times with PBS/Tween® 20, 100 µl/well of TMBlue substrate solution (Intergen) was added and incubated for 20 min at room temperature. Color development was stopped by the addition of 50 µl/well 1N H$_2$SO$_4$, and plates were read at 450 nm.

To quantitate glycosaminoglycans (GAGs) released into the joint space as a result of cartilage proteoglycan degradation, lavage fluids were first digested overnight with papain at 60° C. and hyaluronidase for 2 hrs at 37° C. GAG concentrations were measured by the 1,9 dimethylmethylene blue method of Farndale et al., *Biochim. Biophys. Acta.* 883: 173–177 (1986).

To measure proteoglycan synthesis rates, articular cartilage was first shaved from the femoral condyles and weighed. Approximately 30 mg of cartilage was then incubated in 500 µl of Neuman Tytell serumless medium with 40 µCi of $^{35}SO_4^{-2}$ for 24 hrs at 37° C. Afterward, the media were recovered and stored at −20° C. Proteoglycans were extracted from the cartilage shavings by incubation for 24 hrs in 0.5 ml of 0.5 M NaOH at 4° C. with gentle shaking. Following chromatographic separation of unincorporated $^{35}SO_4^{-2}$ using PD-10 columns (Pharmacia), radiolabeled GAGs released into the culture media or recovered by alkaline extraction were quantitated using scintillation counting.

For histological analyses, tissues harvested from dissected knees were first fixed in 10% formalin for 24 hrs. Tissues containing bone and cartilage were subsequently decalcified by incubation in EDTA. The fixed tissues were imbedded in paraffin, sectioned at 5 µm and stained with either hematoxylin and eosin or toluidine blue.

Immunohistochemical Staining

To identify transduced synoviocytes following transplantation, cultures were fluorescently labeled by incubation for 5 min in 0.1% PKH2 (Sigma) in GBSS. Following inactivation of the PKH2 by mixing with 10 mls 100% FCS, the labeled cells were washed three times in Ham's F12 medium with 10% FCS and resuspended in 1 ml of GBSS for subsequent intraarticular injection. This procedure resulted in detectable fluorescence in about 70–80% of the synoviocytes. To identify cells in the synovium expressing hIL-1β, synovial tissue was first harvested and fixed in 2% paraformaldehyde for 1 hr followed by 30% sucrose for 12 hrs, and frozen sectioned at 5 µm. The sections were then blocked with normal horse 1 g in BSA (0.5% bovine serum albumin, 0.15% glycine in phosphate buffered saline [PBS]) for 45 min, rinsed 3× with BSA and incubated for 1 hr with polyclonal goat IgG anti human IL-1β (R & D Systems) in BSA. The sections were rinsed 3× with BSA and incubated with biotinylated donkey anti-goat 1 g for 1 hr in BSA. The sections were then incubated with streptavadin Cy3.18 (Amersham) in BSA, washed 3× with BSA, 3× with PBS and analyzed by fluorescence microscopy.

Ex Vivo hIL-1β Gene Transfer Using HIG-82 Cells

To permit rapid evaluation of the effects of constitutively elevated expression of hIL-1β in the rabbit knee joint, the lapine synovial cell line, HIG-82, was initially used for ex vivo gene delivery. The allogeneic HIG-82 line has been shown previously to only give short term transgene expression following transplant. (See, for example, Bandara et al., Proc. Nat'l Acad. Sci. USA 90: 10764–10768 (1993)). For these experiments, HIG-82 cells were infected in vitro with the retroviral vector DFG-hIL-1-neo which contains the cDNAs for hIL-1β and neomycin phosphotransferase (neo$^r$). Transduced cells were then positively selected by culture in media containing G418. ELISA measurements of media conditioned by resistant cultures showed the production of greater than 150 ng hIL-1β per $10^6$ cells per 48 hours. Approximately $10^7$ of the HIG-82, hIL-1β+, neo+ cells were then transplanted into one knee joint of nine NZW rabbits by a single intraarticular injection through the patellar tendon. As a negative control, $10^7$ HIG-82 cells transduced with the BAG retrovirus, which carries the coding regions for β-galactosidase (lacZ) and neo', were injected into the contralateral knee joints of each rabbit. The methods of Price, et al. describe how to make and use the BAG virus. "Lineage Analysis in the vertebrate nervous system by retrovirus-mediated gene transfer" Proc. Nat'l. Acad. Sci. U.S.A., 84:156–160 (1987). To monitor the intraarticular accumulation of hIL-1β in the synovial fluids as well as other physiological parameters of arthritis, knee joints were lavaged at 3 and 7 days post transplantation. The animals were sacrificed at 7 days post-transplant to permit internal examination of the knee joints.

Figure 19:
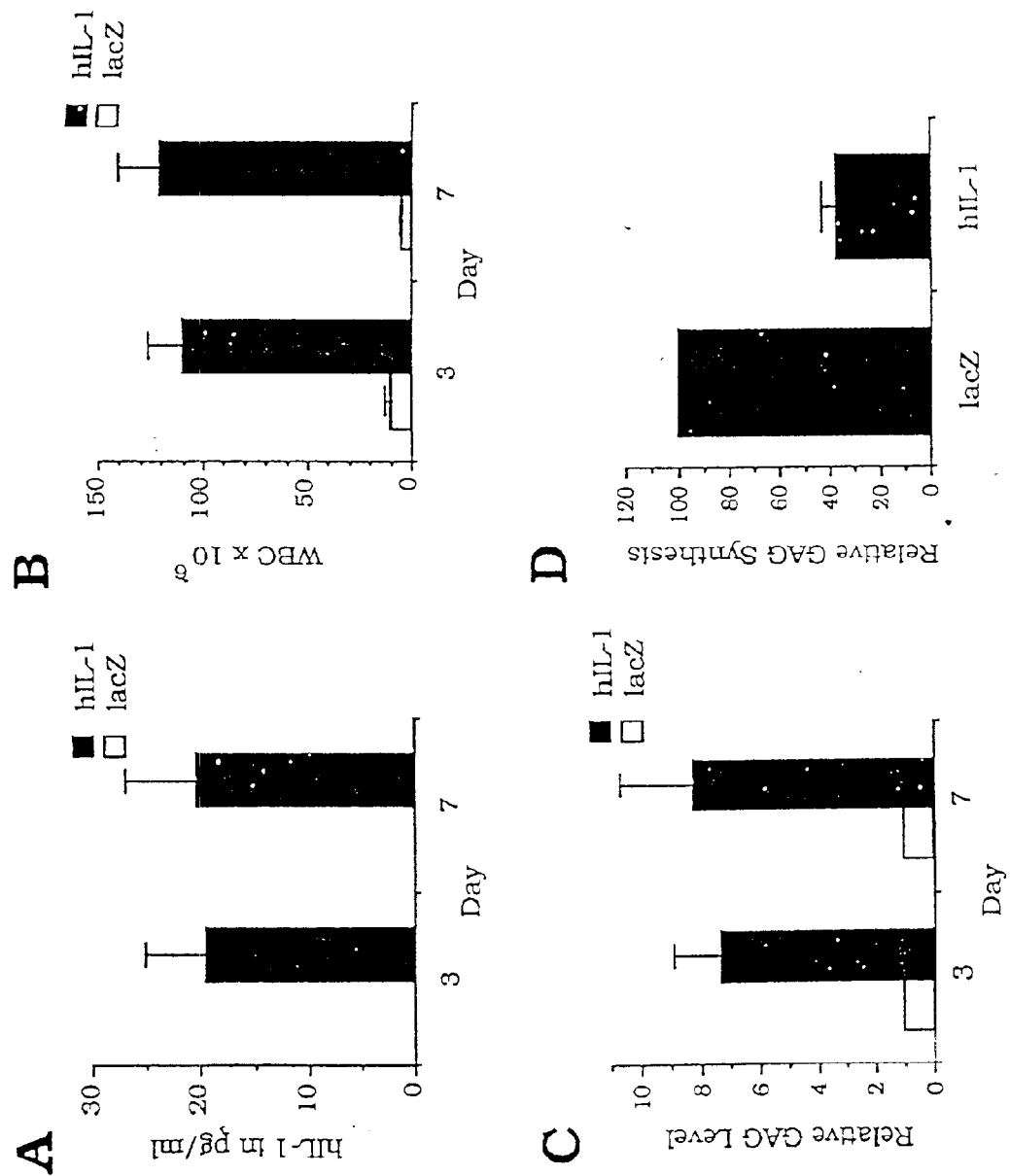

Relative to the lacZ+ controls, knees receiving hIL-1β+ cells became swollen within 24 hrs and developed a severe inflammatory arthritis which persisted until the animals were sacrificed. ELISA measurements of lavage fluids recovered from each of the rabbits demonstrated mean levels of ~20 pg/ml of hIL-β in knees receiving IL-1β+ cells at both 3 and 7 days post transplantation (FIG. 19a), while no measurable hIL-1β was observed in any control knees. Consistent with elevated levels of IL-1β, leukocytic infiltration into the joint space was increased by 20 and 60 fold on days 3 and 7, respectively (FIG. 19b), with mean white blood cell (WBC) counts for the hIL-1β+ knees exceeding $1.0×10^8$ per ml of lavage fluid on both days. Following dissection of the knee joints at day 7, all the hIL-1β+ knees were found to contain extensive nodular synovial hypertrophy accompanied by purulent synovial fluid, while each of the control knees appeared normal. Over expression of hIL-1β was also noted to have a significant impact on cartilage matrix proteoglycans, with a greater than 7 fold increase in glycosaminoglycans (GAGs) released into synovial fluids in hIL-1β knees relative to controls (assigned a value of 1) at both day 3 and day 7 (FIG. 19c). Additionally, proteoglycan synthesis in articular cartilage in hIL-1β+knees was inhibited by nearly 60% relative to controls (FIG. 19d).

Relative GAG synthesis by articular cartilage shavings recovered from knees following dissection at 7 days post-transplant are shown in FIG. 19d. Synthesis rates for hIL-1β+ knee are expressed relative to the contralateral lacZ controls which were assigned a value of 100. All values are expressed as the mean±S.E.M.

Histological examination of the synovial and subsynovial tissues from hIL-1β+knees showed that the synovium was substantially thickened, with villous projections at the surface. The hypertrophied synovium was fibrous and contained an expanded population of synovial fibroblasts and a profuse infiltration of neutrophils. Scattered lymphocytes were also observed near the subsynovial layer. In many of the rabbits, attachment of the expanded synovium to the femoral cartilage and bone was seen, suggestive of early pannus formation.

Inflammation, polymorphonuclear leukocytosis, synovial hypertrophy and hyperplasia, as well as proteoglycan degradation and synthesis inhibition are effects that have been previously attributed to the presence of elevated IL-1β levels. The occurrence of these pathophysiological responses only in joints receiving IL-1β+ clearly indicates that the hIL-1β coding region was successfully transferred to the rabbit knees and expressed in a biologically active form.

Ex Vivo hIL-1β Gene Transfer Using Autologous Synoviocytes

To facilitate longer intraarticular expression of hIL-1β, autologous synoviocytes rather than HIG-82 cells were used for gene delivery. Synovium was surgically harvested from the right knee joints of 15 rabbits, and the synoviocytes of each rabbit were cultured individually. A portion of the synoviocytes from each donor was then infected with the DFG-hIL-1β-neo retrovirus and selected in media containing G418. The level of hIL-1β from the infected cell cultures from each rabbit ranged from 100 to 200 ng per $10^6$ cells per 48 hrs.

In preliminary experiments, $10^7$ hIL-1β+synovial cells were autografted into the left knees of the respective donor rabbits, and as control a similar number of autologous naive cells were injected into the right knees. Of three rabbits initially tested, however, one died after 6 days and a second had to be sacrificed for heath concerns after 12 days. All of the rabbits had diarrhea, were febrile, listless, and had undergone considerable weight loss. In addition to a severe arthritic condition in the knees receiving hIL-1β+cells, post-mortem examination showed the presence of intestinal wall thinning, suggestive of toxic shock. Therefore, for subsequent experiments only $2.5×10^6$ transduced or naive synoviocytes were introduced into test and control knees. Groups of rabbits were sacrificed at 7, 14 and 28 days post-transplantation and analyzed for hIL-1β expression and its physiological effects on the joint.

Gene Expression In Vivo Using Autologous Cells

Autologous transplantation of transduced synoviocytes resulted in substantially higher levels of intraarticular hIL-1β expression than those achieved by the use of allogeneic HIG-82 cells. As shown in FIG. 20, ELISA measurements detected a mean level of approximately 100 pg of hIL-1β per ml of lavage fluid in animals sacrificed at both 7 and 14 days post-transplant. Between week 2 and 4 however, hIL-1β expression appears to have been abruptly lost, since no measurable hIL-β was found in knee lavages of any of the rabbits sacrificed at day 28. Rabbit IL-1β (rIL-1β) production was observed to parallel closely that of hIL-1β transgene expression. Lavage fluids recovered from knees receiving hIL-1β+cells contained over 200 pg/ml of rIL-1β at both day 7 and 14. By day 28, however, rabbit IL-1β had returned to background levels. No detectable human or rabbit IL-1β was measured in any of the control knees or in blood sera.

Figure 21:
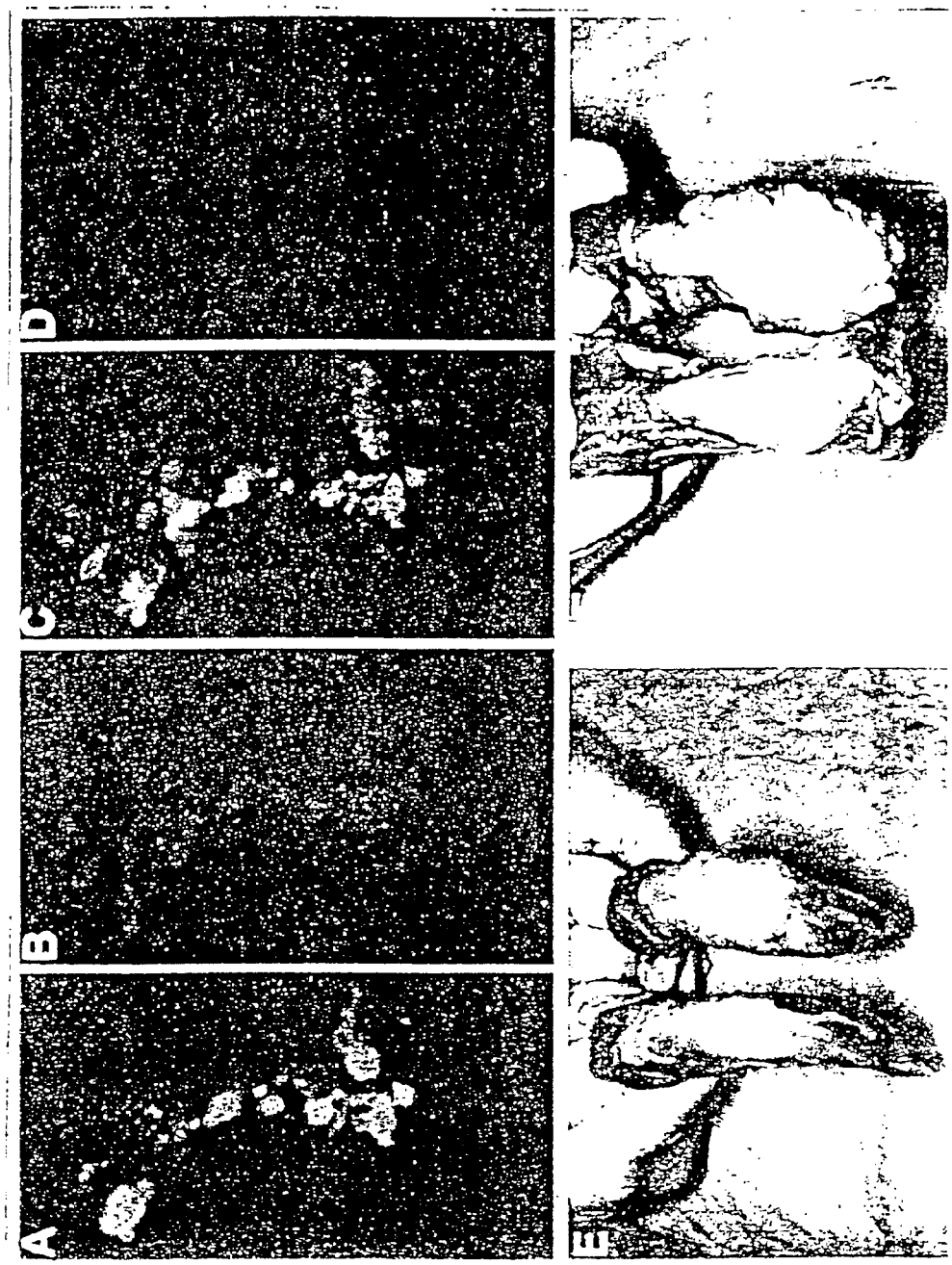

To observe the expression of the hIL-1β transgene in vivo, transduced synoviocyte cultures were fluorescently labeled in vitro with PKDH 2 and autografted into rabbit knee joints; following sacrifice at three day post-transplant, synovial sections were immunohistochemically stained for hIL-1β. As shown in FIGS. 21a–c the regions of the synovium which stain positively for hIL-1β correspond closely with those containing fluorescent cells, demonstrating that the transduced cells have indeed engrafted into the synovial lining and continue to express hIL-1β. Regions which stain for hIL-1β without fluorescence likely represent transplanted synoviocytes unlabeled by the PKH2 in vitro. More specifically FIG. 21a shows fluorescent microscopy of sectioned synovium dissected from a rabbit knee at 3 days post-transplant of PKH2 labeled hIL-1β+, neo+ synoviocytes. Labeled engrafted cells fluoresce green. FIG. 21b shows microscopy of the same section shown in FIG. 21a following immunohistochemical staining for hIL-1β. Regions staining positive for hIL-1β fluoresce red. FIG. 21c presents an overlay of the images of FIG. 21a and 21b; this shows that regions staining positive for hIL-1β closely correspond with regions of PKH2 labeled cells.

Local and Systemic Effects of hIL-1β Expression

Within 24 hrs of transplantation, all knees receiving hIL-1β+cells became noticeably swollen and by 48 hrs displayed a greater than 30% increase in size relative to contralateral control knees that persisted for approximately 18 to 20 days (FIG. 21d). Internally, the pathology of the knee joints front rabbits sacrificed at 7 and 14 days was akin to that seen with the HIG-82 cells, but noticeably worse (FIG. 21e). The synovial fluid was thick and suppurative, and the synovium was massively thickened and lobular. In the 14 day rabbits, numerous attachments could be seen by gross inspection to penetrate the cartilage and bone on the sides of the femoral condyles. Furthermore, in nearly all of the 7 and 14 day rabbits the anterior compartment of the lower leg was filled with a cream colored, caseinous exudate. The muscle tissue surrounding the exudate was often bleached of color, suggestive of local necrosis. Histological examination showed that the substance war comprised primarily of densely packed neutrophils within a loose fibrinous matrix. From further dissection of the leg and knee joint, it appeared that the exudate was an accumulation; of the leukocytic infiltrate from the joint space which penetrated the anterior compartment following partial rupture of the joint capsule.

Although all the animals receiving the hIL-1β+ cells developed a severe arthritis and were symptomatically identical during the first two weeks following transplantation, these changes resolved rapidly following the loss of hIL-1β expression at between days 14 and 28. In three of the five rabbits sacrificed on day 28 the joint capsules appeared relatively normal by gross examination. The remaining two rabbits also showed improvement, but still exhibited synovial hypertrophy and had remnants of an exudate in the anterior compartment.

The nature of the white blood cell infiltration into the joint space of the hIL-1β+ knees varied considerably among the groups of rabbits. An extraordinarily high number of infiltrating leukocytes were observed in recovered knee washings from rabbits sacrificed within the first two weeks (FIG. 22a), with mean levels of $2.6 \times 10^8$ per ml on day 7 and $5.2 \times 10^8$ per ml on day 14, an approximately 400 and 2600 fold increase, respectively, over control knees. Leukocytes in synovial fluids at these time points were predominantly polymorphonuclear. By day 28, the leukocytosis in the joint space of the hIL-1+ knees had abated considerably, but still remained ~10 fold higher than controls and was comprised primarily of mononuclear cells.

Analysis of the effect of hIL-1β over expression on cartilage proteoglycans showed that during the approximately two week period of expression of the hIL-β transgene mean levels of GAGs released into the synovial fluids were greater than 15 fold higher in hIL-1β+ knees over controls (assigned a value of 1) (FIG. 22b). By day 28, GAG release in the IL-1 knees had returned to that of the controls. Similarly, GAG synthesis rates were sharply inhibited in the first two weeks, reaching 80% repression at day 14 as based on the relative GAG synthesis levels measured from articular cartilage shavings (FIG. 22c). Synthesis rates for hIL-1 knees are expressed relative to contralateral controls which were assigned a value of 100. By day 28 significant recovery of the synthesis was observed.

Figure 22:
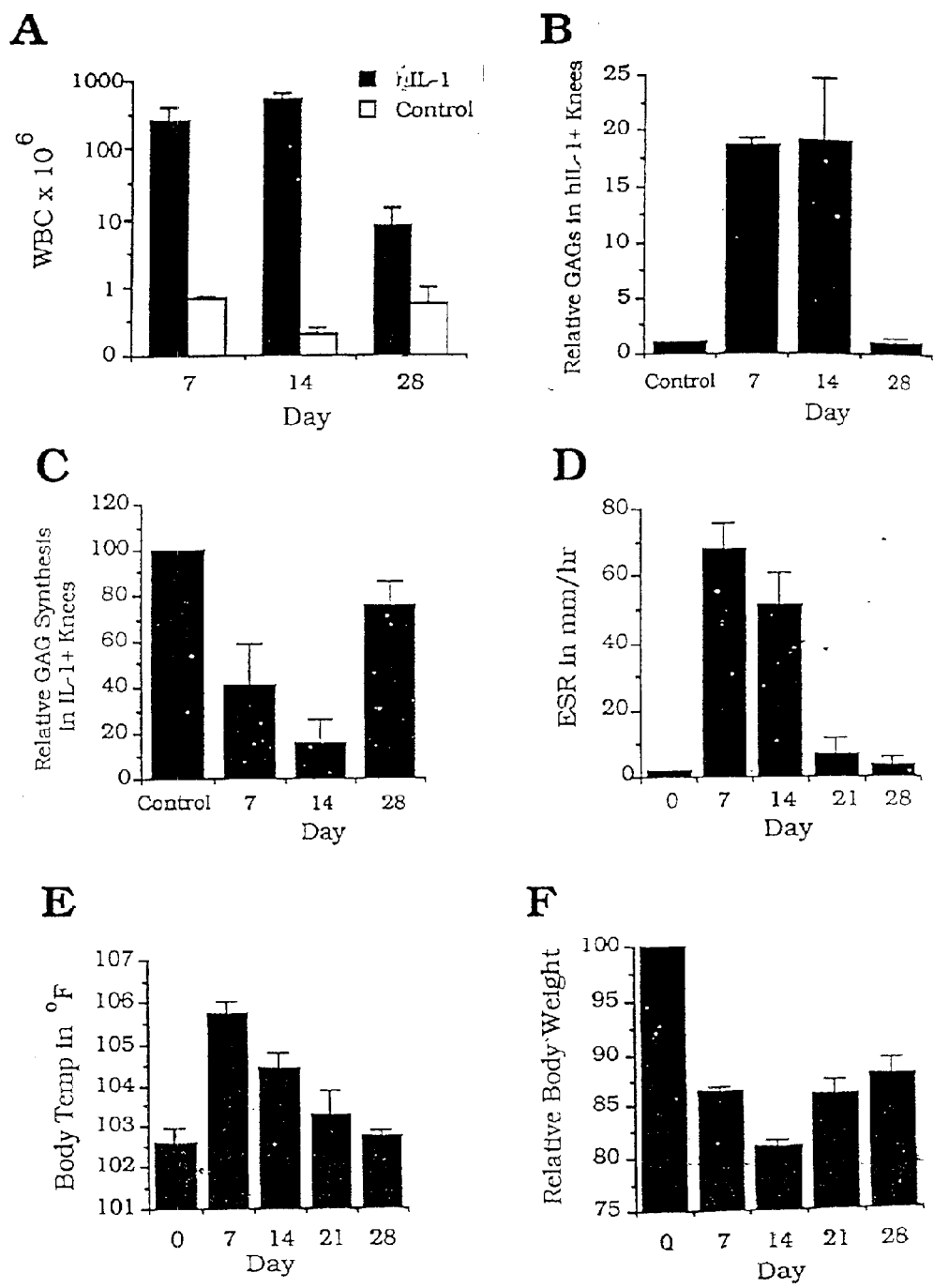
Figure 23:
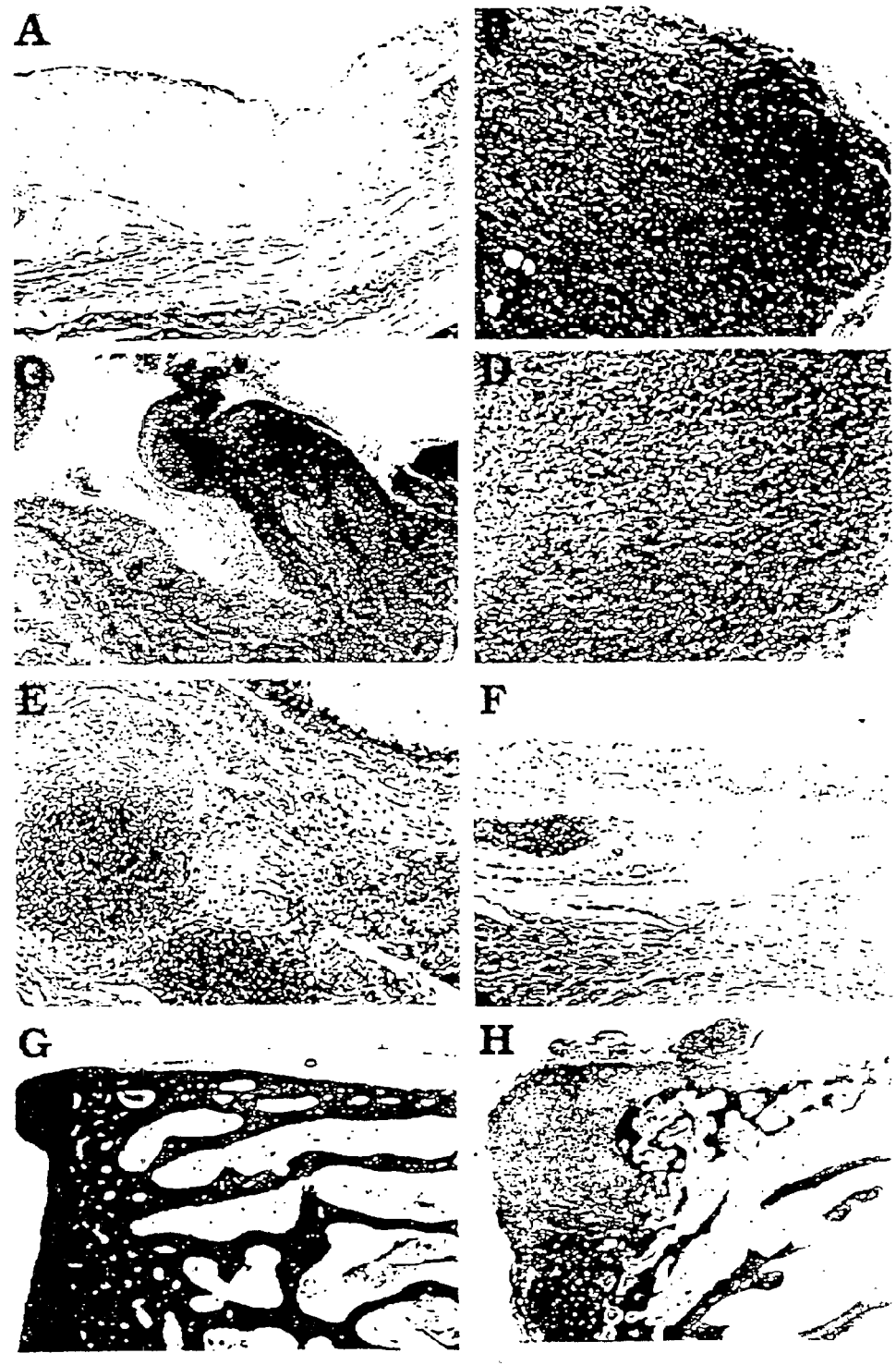

Consistent with the presence of a systems, inflammatory response, mean elevated erythrocyte sedimentation rates were increased greater than 25 fold at both 7 and 14 days (FIG. 22), but by day 21 had returned to near normal levels. The rabbits also developed fevers which peaked on or before day 7 and gradually subsided by day 28 (FIG. 22e). Additionally, the rabbits experienced a mean 15% loss in body weight by day 12 relative to day 0 (FIG. 22f) which increased slightly thereafter.

Histological Analysis

FIG. 23a illustrates normal synovium, against which others are compared, at 7 days post transplantation of naive synoviocytes.

Histological examination revealed a number of discrete changes in the synovium and the composition of the inflammatory cells infiltrating the tissue of the joint capsule during the four weeks following transplantation of the hIL-1β+ cells. Similar to the one week HIG-82-IL-1β knees, the synovium from autografted rabbits sacrificed at one week was fibrous and severely hypertrophied, expanded by synovial cell hyperplasia and large numbers of infiltrating neutrophils (FIG. 23b). Scattered lymphocytes and other mononuclear cells were also observed. In rabbits sacrificed at week two, the thickened synovium showed signs of neo-vascularization and lobular thickening of the synovium. A large population of infiltrating neutrophils was still present, but appeared somewhat concentrated toward the outer edges of the expanded synovium. Toward the subsynovium, diffuse populations of lymphocytes were observed along with the formation of lymphoid foci (FIG. 23c and d; FIG. 23d shows a higher magnification of FIG. 23c, showing lymphoid (bottom) and neutrophilic infiltration (top), and synovial hypertrophy and hyperplasia). A highly aggressive pannus was also seen in all the rabbits, which had attached to and eroded all periarticular bone surfaces on the femoral condyles as well as regions of cartilage. Typically, the most invasive pannus formation occurred laterally and medially near the edge of the articulating surface. At these regions, severe degradation of cartilage could be seen as well as penetration of the pannus through the bone and into the marrow (FIG. 23g and h). FIG. 23(g) shows a section of femoral condyle from knee at 14 days post-transplant of naive synoviocytes. Cartilage (left) was shaved for GAG synthesis assays. FIG. 23(h) shows a section of femoral condyle from hIL-1β+ knee at 14 days post-transplant. Highly aggressive pannus is shown eroding cartilage and subchondral bone. Although articular cartilage showed substantial loss of metachromasia following toluidine-blue staining, cartilage without attached pannus formation showed little apparent structural damage (data not shown).

Considerable histological variability was observed among the 28 day rabbits. In the two rabbits, which by gross examination appeared arthritic, the synovial tissue in general remained somewhat thickened and vascularized, and contained both peri- and subsynovial lymphoid follicles (FIG. 23e). The infiltrating neutrophil population, however, had diminished significantly. Within the subsynovium, concentrations of macrophages were observed whose cytoplasm was greatly enlarged and appeared to contain numerous lipid-filled vesicles, perhaps suggestive of tissue remodeling. A thin lining of normal synovial cells appeared to have reformed over much of the thickened synovial mass. In a few isolated pockets, the synovial layer contained high local concentrations of neutrophils, suggesting that a few of the transplanted synoviocytes continued to express hIL-1β. Pannus invasion and bone erosion were still evident in cross sections of the femoral condyles of these rabbits. Although cartilage sections from the tibial plateau and femoral condyles showed a loss of metachromasia following toluidine-blue staining, regions without attached pannus appeared, at least structurally, intact and unaffected.

In the remaining three 28 day rabbits, a clear reduction in the severity of synovitis was evident (FIG. 23f). A normal lining of synovial cells had reformed over the synovial layer. The synovial layer itself was still somewhat thickened and fibrous; however, the expanded synovial cell and infiltrating neutrophil and macrophage populations were noticeably absent. Lymphoid follicles were still present, but their number and size were significantly reduced. Bone and cartilage erosions were still present, as well as a moderate loss of toluidine-blue staining in articular cartilage.

This example demonstrates that sustained, interarticular, synovial expression of IL-1β can produce all the major pathologies associated with human RA. Intraarticularly manifestations included intense inflammation, breakdown of the cartilaginous matrix, inhibition of matrix synthesis, leukocytosis of the joint space and synovium, synovial hyperplasia, hypertrophy, neo-vascularization and fibrosis, and the formation of lymphoid follicles and highly aggressive pannus formation with erosion of the articular cartilage and periarticular bone. Extraarticular and systemic pathologies include periarticular loss of bone, elevated temperature and elevated erythrocyte sedimentation rate, loss of weight, diarrhea and fever.

From this data, it is clear that the production of hIL-1β from the transgene stimulated local synthesis and secretion of rabbit IL-1β in a paracrine fashion, making the total IL-1β content of the affected joints between 300 to 400 pg/ml. This compares to values of 0.5 to 5 ng/ml reported for human rheumatoid synovial fluid Hopkins, et al. "Cytokines in Synovial Fluid I. The Presence of Biologically Active and Immunoreactive IL-1, *Clin. Exp. Immunol.* 72:422 (1988). Furthermore, the IL-1 induced rTNFα levels exceeded 600 pg/ml, compared to the 0 to 7 ng/ml range reported in RA by Saxne, et al. "Detection of Tumor Necrosis Factor a but not Tumor Necrosis Factor b in Rheumatoid Arthritis Synovial Fluid and Serum," *Arthritis Rheum.* 31:1041 (1988). Thus, the intraarticular concentration of IL-1 and TNFα in human RA and our model appear roughly equivalent. These findings indicate that this hIL-1β gene transfer model not only reflects the potential for IL-1β to contribute to RA pathogenesis, but also provides a close approximation of the RA cytokine milieu and, thus, a novel vehicle to assess the efficacy of RA therapeutics.

Since TNFα has been shown to be a potent stimulator of IL-1 and GM-CSF production in cultured RA synovial fibroblasts, it has been put forth that TNFα is at the top of the inflammatory cytokine cascade that mediates the pathology of RA (See, for example, Brennan, et al. "Inhibitory effects of TNFα antibodies on synovial cell interleukin-1 production in rheumatoid arthritis" *Lancet* 2:244 (1989); Haworth, et al. "Expression of granulocyte-macrophage colony-stimulating factor in rheumatoid arthritis: regulation by tumor necrosis factor-α," *Eur. J. Immunol.* 21:2575 (1991); and Maini, et al. "Beneficial effects of tumor necrosis factor-alpha (TNF-α) blockade in rheumatoid arthritis (RA)," *Clin. Exp. Immunol.* 101:207 (1995). The results of experiments described here, however, demonstrate that elevated intraarticular levels of IL-1 can stimulate both IL-1 and TNFα production and that upon removal of IL-1, inflammatory sequelae lessen in severity even in the presence of elevated TNFα. This shows that in the hierarchy of inflammatory cytokines, IL-1 is most likely the principal mediator of RA-like pathology in the rabbit knee.

The very marked systemic changes, which in the early experiments included serious illness and death of one animal, were quite striking. Intravenous injection of IL-1β is known to induce both fever and cachexia, suggesting that IL-1β was not totally contained within the joint capsule of the rabbits. However, extraarticular human or rabbit IL-1β or rTNFα was not detected in the sera of any of the animals. Therefore, these effects most likely arise either from the chronic presence of very low levels (<3.0 pg/ml) of these cytokines in the bloodstream or elevated levels of another effector molecule such as IL-6. IL-1 is a potent inducer of IL-6, which is the most abundant cytokine in human rheumatoid synovial fluids. IL-6 is an important mediator of the acute phase response, which accounts for the elevated ESR, and has also been implicated as an inducer of fever and cachexia in some animal systems Hirano, et al. "Biological and clinical aspects of interleukin-6," *Immunol Today* 11:443 (1990).

The results presented in this example clearly illustrate the capacity of IL-1β to serve as an effector molecule in RA and suggest that agents which block the interarticular activity of IL-1β will be therapeutic. These results also serve to validate the use of gene transfer as a means to study the in vivo action of gene products associated with the pathogenesis of arthritis, and the rabbit model of the present invention.

Example XVII

The procedures of Example III were repeated substituting cDNA encoding the following genes instead of IRAP: sIL-IR Type I; sIL-IR Type II; sTNF-αR Type II; vIL-10; TIMP-2; CTLA4; FasL; and iNOS. Briefly, an MFG retroviral vector was constructed containing cDNA encoding the gene of interest selected from the list above. The MFG constructs were then used to infect synovial cells recovered from rabbit knees. Various methods were used to determine whether the gene expression occurred in the cells. Immunohistochemistry, bioassay and western analysis were used in some cases; a determination was made as to whether the gene was expressed. ELISA and NO production were used in some cases; a quantitative determination of the level of gene expression was made. Results are presented in Table 3 below.

TABLE 3

Gene Expression in Synovial Cells Following Retroviral Gene Transfer

| Gene | Method of detection | Presence/amount of product of interest |
|---|---|---|
| sTNF-alpha receptor type I | ELISA | 50 ng per $10^6$ cells |
| sTNF-alpha receptor type II | ELISA | 30 ng per $10^6$ cells |
| sIL-1 receptor type I | ELISA | 5 ng per $10^6$ cells |
| sIL-1 receptor type II | ELISA | 5 ng per $10^6$ cells |
| vIL-l0 | ELISA | 50 ng per $10^6$ cells |
| TIMP-2 | Bioassay | Positive |
| CTLA4-Ig | Western | Positive |
| FasL | Immunohisto. | Positive |

TABLE 3-continued

Gene Expression in Synovial Cells
Following Retroviral Gene Transfer

| Gene | Method of detection | Presence/amount of product of interest |
|---|---|---|
| iNOS | Western | Positive |
| iNOS | NO production | 20 μm per $10^6$ cells |

Example XVIII

The animal model procedures of Examples XI and XVI were repeated using IL-6 and TNF-α.

FIG. 24a shows the expression of murine IL-6 (mIL-6) in knees injected with mIL-6 versus control knees. Several ng of mIL-6 were found in the injected knees, while mIL-6 in control knees was below the limit of detection. Thus, mIL-6 was being expressed in the injected knees. FIG. 24b shows that the amount of GAG released was much greater in the mIL-6 knee after 3 days, but was equal to the control knees after 7 days.

FIG. 25a shows the leukocyte infiltration of knees injected with murine TNF-α (mTNF-α) versus control knees. The leukocyte infiltration in the mTNF-α knees was about four to five times that of control knees after both 3 and 7 days, indicating that the TNF-α was being expressed in a biologically active form and causing inflammation. FIG. 25b shows inhibition of cartilage proteoglycan synthesis in the knees receiving the mTNF-α.

These data demonstrate that the gene therapy methods disclosed and claimed in the present invention can be used to modulate the disease process in an animal model of arthritis. In turn, these Examples enable the claimed gene therapy based treatment of connective tissue pathologies and systemic indices of inflammation within the afflicted joint(s). It will be appreciated by those skilled in the art that this invention provides a method of introducing into a target cell of a mammalian host in vitro, or in the alternative in vivo, at least one gene which codes for proteins and/or RNA with therapeutic properties. This method includes employing genes having DNA that is capable of maintenance and expression.

It will be appreciated by those skilled in the art that this invention provides a method of introducing at least one gene encoding a product into at least one target cell of a mammalian host for treating a connective tissue condition of the mammalian host.

It will be understood by those skilled in the art that this invention provides a method to repair and regenerate the connective tissue of a mammalian host.

It will be further understood that the present invention discloses ex vivo and in vivo techniques for delivery of a DNA sequence of interest to the target cells of the mammalian host. The ex vivo technique involves prior removal and culture of target autologous cells, in vitro infection of the DNA sequence, DNA vector or other delivery vehicle of interest into the target cells, followed by transplantation to the modified target cells to the target joint of the mammalian host, so as to effect in vivo expression of the gene product of interest. The in vivo technique bypasses the requirement for in vitro culture of target cells, instead relying on direct transplantation of the DNA sequence, DNA vector or other delivery vehicle to the target in vivo cells, thus effecting expression of the gene product of interest.

It will be further understood that this invention provides a method to produce an animal model for the study of connective tissue pathology.

It will be appreciated by those persons skilled in the art that this invention provides a method of using and a method of preparing numerous genes including a gene encoding soluble interleukin-1 receptor that is capable of binding to and neutralizing substantially all isoforms of interleukin-1, and thus substantially protect cartilage of a mammalian host from pathological degradation. In addition, it will be understood by those persons skilled in the art that the method of using the gene of this invention will reduce inflammation, protect soft tissues of the joint and suppress the loss of bone that occurs in patients suffering with arthritis.

It will be appreciated by those persons skilled in the art that the viral vectors employed in the present invention may be employed to transfect synovial cells in vivo or in culture, such as by direct intraarticular injection or transplantation of autologous synovial cells from the patient transduced with one or more vectors carrying one or more genes.

It will also be understood that a class of DNA sequences, as described throughout this specification, including but not limited to IRAP, may use the claimed methods to effect reduction of inflammation, protect soft tissues of the joint and suppress the loss of bone that occurs in patients suffering with arthritis.

The present invention provides a method of preparing various vectors, both viral and non viral, that contain DNA sequences encoding for numerous genes of interest. These genes are known by those skilled in the art to be useful in the therapeutic treatment of various connective tissue disorders. The present invention demonstrates that infection of target cells with these vectors results in expression of the genes in vivo when target cells are returned to the host. Alleviation of symptoms common to numerous connective tissue disorders is then observed. Thus, the methods of the present invention provide a method of treating a host through the use of target cells transfected with a vector coding for various therapeutic genes.

The present invention also provides a method for establishing an animal model for the study of connective tissue disorders. This model also provides for the preparation of viral or non-viral vectors here containing DNA sequences encoding for numerous genes known to cause symptoms representative of those associated with connective tissue disorders. Injection of these vectors into an animal result in the expression of the gene and the onset of the symptoms. Injection can be accomplished by in vivo means, by directly injecting the vector into the host, or by ex vivo means, by transfecting target cells, such as synoviocytes with the vectors and injecting the transfected cells into the host.

Whereas particular embodiments of this invention have been described above for purposes of illustration, it will be evident to those persons skilled in the art that numerous variations of the details of the present invention may be made without departing from the invention as defined in the appended claims.

What is claimed is:

1. A method for treating arthritis in a mammalian host, comprising:

generating a recombinant viral vector comprising a DNA sequence encoding soluble IL-1 receptor operatively linked to a promoter;

infecting in vitro population of autologous synovial cells with said recombinant viral vector resulting in a population of transduced synovial cells; and transplanting said transduced synovial cells by intraarticular injection to an arthritic joint space of a mammalian host, such that expression of said DNA sequence in said joint space results in reduction of cartilage destruction or reduction in synovitis.

2. The method of claim 1, wherein said soluble IL-1 receptor is selected from the group consisting of soluble IL-1 receptor Type 1 and soluble IL-1 receptor Type II.

3. The method of claim 1, wherein said recombinant viral vector is an adenovirus.

4. The method of claim 1, wherein transplantation of the transduced cells is by intraarticular injection.

5. The method of claim 1, further including the step of storing said population of transduced cells prior to transplantation.

6. The method of claim 5, wherein said population of transduced cells are stored in 10% DMSO under liquid nitrogen prior to transplantation.

7. The method according to claim 1, wherein the viral vector is a retroviral vector.

8. The method according to claim 1, wherein the viral vector is an adeno-associated viral vector.

9. The method according to claim 1, wherein the viral vector is a herpes simplex viral vector.

10. A method for treating-arthritis in a mammalian host, comprising:

generating a recombinant plasmid vector comprising a DNA sequence encoding soluble IL-1 receptor operatively linked to a promoter;

transforming in vitro population of synovial cells with said recombinant plasmid vector resulting in a population of transformed synovial cells; and transplanting said transformed synovial cells by intraarticular injection to an arthritic joint space of a mammalian host, such that expression of said DNA sequence in said joint space results in reduction of cartilage destruction or reduction in synovitis.

11. The method of claim 10, further including the step of storing said population of transformed cells prior to transplantation.

12. The method of claim 11, wherein said population of transformed cells are stored in 10% DMSO under liquid nitrogen prior to transplantation.

* * * * *